(12) United States Patent
Moriarty et al.

(10) Patent No.: US 8,765,754 B2
(45) Date of Patent: Jul. 1, 2014

(54) PYRROLOTRIAZINE COMPOUNDS

(75) Inventors: Kevin J. Moriarty, East Norriton, PA (US); Dora Do-York Wong, legal representative, East Norriton, PA (US); Zenon Konteatis, Chatham Township, NJ (US); Kristofer Moffett, Middletown, CT (US); Younghee Lee, Blue Bell, PA (US); Wenchun Chao, Portage, MI (US)

(73) Assignee: Locus Pharmaceuticals, Inc., West Conshohocken, PA (US)

( * ) Notice: Subject to any disclaimer, the term of this patent is extended or adjusted under 35 U.S.C. 154(b) by 227 days.

(21) Appl. No.: 13/266,921

(22) PCT Filed: Apr. 28, 2010

(86) PCT No.: PCT/US2010/032698
§ 371 (c)(1),
(2), (4) Date: Apr. 23, 2012

(87) PCT Pub. No.: WO2010/126960
PCT Pub. Date: Nov. 4, 2010

(65) Prior Publication Data
US 2012/0232054 A1    Sep. 13, 2012

Related U.S. Application Data

(60) Provisional application No. 61/173,869, filed on Apr. 29, 2009.

(51) Int. Cl.
*A01N 43/64* (2006.01)
*A61K 31/53* (2006.01)
*C07D 487/00* (2006.01)

(52) U.S. Cl.
USPC .......................................... 514/243; 544/183

(58) Field of Classification Search
None
See application file for complete search history.

(56) References Cited

FOREIGN PATENT DOCUMENTS

| WO | 00/17203 A1 | 3/2000 |
|---|---|---|
| WO | 00/71129 A1 | 11/2000 |
| WO | 03/016338 A1 | 2/2003 |
| WO | 2005/014599 A1 | 2/2005 |
| WO | 2005/037836 A2 | 4/2005 |
| WO | 2005/047290 A2 | 5/2005 |
| WO | 2006/099075 A2 | 9/2006 |
| WO | 2007/056170 A2 | 5/2007 |
| WO | 2008/039218 A2 | 4/2008 |
| WO | 2008/121742 A2 | 10/2008 |
| WO | 2010/009342 A2 | 1/2010 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
International Search Report for PCT/US2010/032698 dated Jul. 12, 2010 [PCT/ISA/210].
Communication from the European Patent Office issued Sep. 14, 2012 in counterpart European Application No. 10770238.3.

* cited by examiner

*Primary Examiner* — Jeffrey H Murray
(74) *Attorney, Agent, or Firm* — Sughrue Mion, PLLC

(57) ABSTRACT

A compound of formula (I):

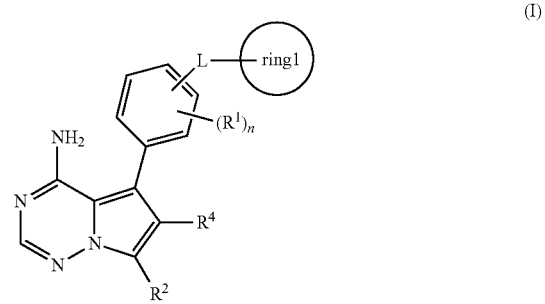

wherein all symbols have the same meanings as defined in the specification; a salt thereof, a solvate thereof, an N-oxide thereof, or a prodrug thereof, has a Btk inhibitory activity, and is useful as a method for preventing and/or treating a rheumatoid arthritis, an autoimmune disease, a B cell lymphoma of cancer, and the like.

9 Claims, No Drawings

PYRROLOTRIAZINE COMPOUNDS

CROSS-REFERENCE TO RELATED APPLICATION

This application claims the benefit of U.S. Provisional Application No. 61/173,869, filed Apr. 29, 2009 in the United States Patent and Trademark Office, the disclosure of which is incorporated by reference in its entirety.

FIELD OF THE INVENTION

The present invention relates to pyrrolotriazine compounds useful as tyrosine kinase inhibitors, particularly Bruton's tyrosine kinase (Btk) inhibitors. For more detail, the present invention relates to a novel compound represented by formula (I)

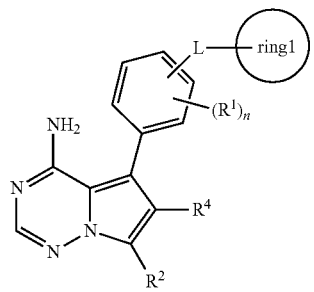

(I)

a salt thereof, a solvate thereof, an N-oxide thereof or a prodrug thereof.

BACKGROUND OF THE INVENTION

Bruton's tyrosine kinase (abbreviated as Btk hereinafter) belongs to the Tee family of non-receptor tyrosine kinases that is expressed in B cells and other hematopoietic cell types (such as monocyte, mast cell). Btk plays an essential and important role in the B-cell signaling pathways and is an essential factor of B-cell survival, differentiation, proliferation and activation. B-cell signaling through the B-cell antigen receptor (BCR) leads to a wide range of biological outputs. If BCR-mediated signaling is aberrant, it causes deregulated B-cell activation and/or the formation of pathogenic auto-antibodies. Mutations in the gene encoding human Btk results in X-linked agammaglobulinemia (XLA). It is known that this disease is caused by abnormal production of immunoglobulin based on the impaired maturation of B-cells (see Nature 361, 226-233, (1993)). The clinical signs of this disease exemplify the marked decrease of B-cells in peripheral blood and the increased susceptibility to bacterial infection or the like. In addition, Btk is also known to be involved in mast cell activation or platelet physiology.

Therefore, inhibitors of Btk could be useful for treatment of an allergic disease, an autoimmune disease, an inflammatory disease, a thromboembolic disease, cancer or the like.

It has been disclosed that a pyrrolotriazine compound represented by formula (A)

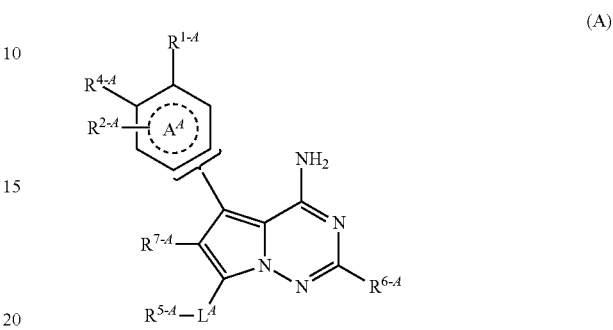

(A)

wherein ring $A^A$ is aromatic; $R^{1-A}$ represents H or halogen; $R^{2-A}$ represents H or halogen; $R^{4-A}$ represents —$OR^{10-A}$ wherein $R^{10-A}$ represents H, ($C_1$-$C_3$)alkyl, optionally substituted phenyl, or optionally substituted benzyl; $L^A$ represents a bond, a divalent phenyl; $R^{5-A}$ represents $NR^{18-A}R^{19-A}$ wherein $R^{18-A}$ represents H or ($C_1$-$C_3$)alkyl, $R^{19-A}$ represents H, ($C_1$-$C_3$)alkyl, $SO_2R^{25-A}$ wherein $R^{25-A}$ represents ($C_1$-$C_3$)alkyl; $R^{6-A}$ represents H or ($C_1$-$C_3$)alkyl; and $R^{7-A}$ represents H, CN, or ($C_1$-$C_3$)alkyl (the definition of each group in the above described formula is excerpted), is useful for IGF-1R kinase inhibitor (From WO 2007/056170).

Furthermore, it has been described that a pyrrolotriazine compound represented by formula (B)

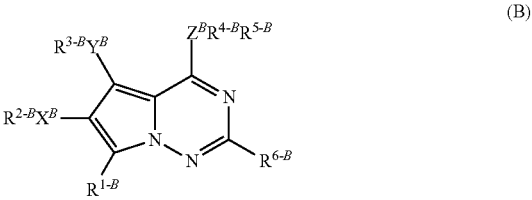

(B)

wherein $X^B$ and $Y^B$ independently selected from O, OCO, S, $SO_2$, CO, $CO_2$, halogen, nitro, cyano, or $X^B$ or $Y^B$ are absent; $Z^B$ is selected from O, S or N; $R^{1-B}$ is hydrogen, $CH_3$, OH, $OCH_3$, SH, $SCH_3$, halogen, nitro, or cyano; $R^{2-B}$ and $R^{3-B}$ are independently hydrogen, alkyl, substituted alkyl, aryl, substituted aryl, heterocyclo, substituted heterocyclo; $R^{4-B}$ and $R^{5-B}$ are independently hydrogen, alkyl, substituted alkyl, aryl, substituted aryl, heterocyclo, substituted heterocyclo, except that when $Z^B$ is O or S, $R^{5-B}$ is absent, or when $Z^B$ is nitrogen, $R^{4-B}$ and $R^{5-B}$ are not both hydrogen; $R^{6-B}$ is hydrogen, alkyl, substituted alkyl, aryl, substituted aryl, heterocyclo, substituted heterocyclo or halogen (the definition of each group in the above described formula is excerpted), is useful for VEGF kinase inhibitor (From WO 2000/71129).

In addition, it has been disclosed that a imidazopyrimidine compound represented by formula (C)

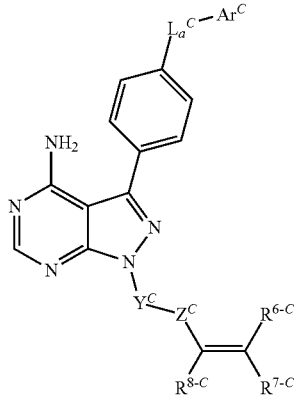

wherein $L_a^C$ is $CH_2$, O, NH or S; $Ar^C$ is a substituted or unsubstituted aryl, or a substituted or unsubstituted heteroaryl; $Y^C$ is an optionally substituted group selected from among alkyl, heteroalkyl, cycloalkyl, heterocycloalkyl, aryl and heteroaryl; $Z^C$ is CO, OCO, NHCO, CS; $R^{7-C}$ and $R^{8-C}$ are independently selected from among H, unsubstituted $C_1$-$C_4$alkyl, substituted $C_1$-$C_4$alkyl, unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R^{7-C}$ and $R^{8-C}$ taken together from a bond; $R^{6-C}$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl (with the proviso that the definition of each group in the above described formula is excerpted), is useful for inhibitor of Btk (From WO2008/039218, WO 2008/121742 and WO 2010/009342).

Meanwhile, there are some protein kinases, such as Lck, Lyn, Fyn that are closely related to Btk. In particular, it is known that retinal abnormalities are observed in Lck (the Src family of non receptor-type kinases) deficient mice (See oncogene, 16, 2351-2356, (1998)).

DISCLOSURE OF THE INVENTION

It is desired to develop a Btk inhibitor as a therapeutic agent for an allergic disease, an autoimmune disease, an inflammatory disease, a thromboembolic disease, cancer or the like.

The compounds of the present invention represented by formula (I) inhibit Btk activity and many selectively inhibit Btk activity, particularly against Lck and comprise the present invention. Additionally, the compounds of the present invention have superior pharmacokinetic features.

Namely, the present invention relates to
[1] A compound represented by formula (I)

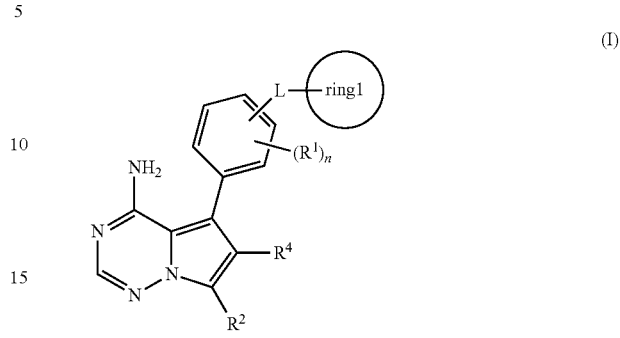

wherein ring1 represents (1) a C5-7 carbocyclic ring or (2) a 5-10 membered heterocyclic ring, any of which is optionally substituted with 1-5 substituent(s) selected from the group consisting of halogen, a C1-4 alkyl, $CF_3$, nitrile, $CONH_2$, and a C1-4 alkoxy;

$R^1$ represents halogen, a C1-4 alkyl, or $OR^{5-103}$;

L represents —O—, —S—, —SO—, —$SO_2$—, —NH—, or —C(O)—;

$R^2$ represents (1) a C1-4 alkyl substituted with $OR^{5-103}$, (2) C2-4 alkenyl, or (3) ring2 optionally substituted with one or more —K—$R^3$;

ring2 represents (1) a C4-7 carbocyclic ring or (2) a 4-7 membered heterocyclic ring, any atom of which is optionally substituted with one or more oxo group;

K represents bond, a C1-4 alkylene, —C(O)$CH_2$—, —C(O)$CH_2CH_2$—, —C(O)O—, —$CH_2$C(O)—, —$CH_2$C(O)O—, —C(O)—, —$CH_2$O—, —$CH_2CH_2$O—, —O—, —$OCH_2$—, —$OCH_2$C(O)— or —$SO_2$—, wherein the left bond binds to ring2;

$R^3$ represents (1) hydrogen, (2) $NR^{3-101}R^{3-102}$, (3) a C1-4 alkyl optionally substituted with $NR^{3-101}R^{3-102}$, (4) a C2-4 alkenyl optionally substituted with $NR^{3-101}R^{3-102}$, (5) $CF_3$, (6) nitrile, (7) halogen, or (8) a cyclic ring optionally substituted with 1-5 substituent(s) selected from the group consisting of halogen, a C1-4 alkyl, a C1-4 alkoxy, $CF_3$, nitrile and oxo, wherein the cyclic ring is selected from the group consisting of morpholine, pyrrolidine, benzene, piperazine, tetrahydropyran, piperidine, tetrahydrofuran, oxazole, thiazole, pyrazole and oxadiazole;

$R^4$ represents (1) halogen, (2) $CONR^{4-101}R^{4-102}$, (3) $CO_2R^{4-103}$, (4) ring3, (5) a C1-4 alkyl which is substituted with 1-5 substituent(s) selected from ring4, nitrile, $NR^{4-101}R^{4-102}$, $CONR^{4-101}R^{4-102}$, $CO_2R^{4-103}$, $COR^{4-103}$, $OR^{4-103}$, $SOR^{4-103}$ and $SO_2R^{4-103}$, or (6) C2-4 alkenyl which is substituted with 1-5 substituent(s) selected from ring4, nitrile, $NR^{4-101}R^{4-102}$, $CONR^{4-101}R^{4-102}$, $CO_2R^{4-103}$, $COR^{4-103}$, $OR^{4-103}$, $SOR^{4-103}$ and $SO_2R^{4-103}$;

$R^{3-101}$ and $R^{3-102}$ each independently represent (1) hydrogen, (2) a C1-4 alkyl, (3) $COR^{3-103}$, (4) $CONR^{3-103}R^{3-104}$ or (5) $SO_2R^{3-103}$, wherein $R^{3-103}$ and $R^{3-104}$ each independently represent hydrogen or a C1-4 alkyl;

$R^{4-101}$, $R^{4-102}$ and $R^{4-103}$ each independently represent (1) hydrogen, (2) $COR^{5-103}$, (3) $NR^{5-101}R^{5-102}$, (4) ring5, or (6) a C1-4 alkyl optionally substituted with $CO_2R^{5-103}$, $OR^{5-103}$, or $NR^{5-101}R^{5-102}$;

$R^{5-101}$, $R^{5-102}$ and $R^{5-103}$ each independently represent hydrogen or a C1-4 alkyl;

ring3, ring4 and ring5 each independently represent 4-7 membered heterocyclic ring optionally substituted with 1-5 substituent(s) selected from the group consisting of halogen, oxo, a C1-4 alkyl, a C1-4 alkoxy, $CF_3$, $CONR^{5-101}R^{5-102}$, $CO_2R^{5-103}$, $SOR^{5-103}$, $SO_2R^{5-103}$ and nitrile; n represents 0, or an integer of 1-4, wherein when n is more than 1, each $R^1$ may be same or different;
a salt thereof, a solvate thereof, an N-oxide thereof or a prodrug thereof,

[2] The compound as described above [1], wherein ring1 is selected from the group consisting of cyclopentane, benzene, thiazole, indole and benzothiazole,

[3] The compound as described above [1], wherein the ring2 is selected from the group consisting of cyclopentane, cyclohexane, cycloheptane, benzene, azetidine, pyrrolidine, tetrahydropyridine, piperidine, perhydroazepine, morpholine, piperazine, pyran, thiopyran, pyridine, pyrazole, isoindoline and perhydroisoquinoline,

[4] The compound as described above [1], wherein halogen in $R^4$ is chlorine;
ring3 in $R^4$ is selected from the group consisting of pyrrolidine, piperidine, morpholine, tetrahydrothiopyran and pyridine; or
ring4 in $R^4$ is selected from the group consisting of pyrrolidine, piperidine, morpholine, imidazole, tetrazole and pyridine,

[5] The compound as described above [4], wherein $R^4$ is (1) chlorine, (2) piperidine, (3) tetrahydrothiopyran, (4) pyrrolidine, (5) morpholine, (6) a C1-4 alkyl which is substituted with substituent(s) selected from the group consisting of $NR^{4-101}R^{4-102}$, $CO_2R^{4-103}$, $OR^{4-103}$, pyrrolidine, morpholine and pyridine, or (7) a C2-4 alkenyl which is substituted with substituent(s) selected from the group consisting of $NR^{4-101}$, $R^{4-102}$, $CO_2R^{4-103}$, $OR^{4-103}$, pyrrolidine, morpholine and pyridine, wherein all the symbols have the same meanings as described above [1],

[6] The compound as described above [1], which is a compound represented by formula (I-1)

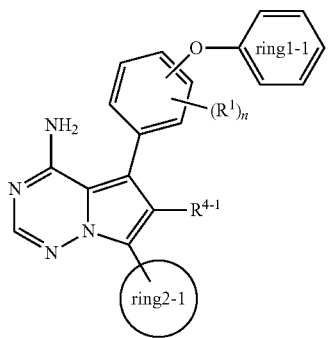

(I-1)

wherein ring1-1 represents benzene which may be optionally substituted with 1-5 substituent(s) selected from the group consisting of halogen, a C1-4 alkyl, $CF_3$, and nitrile;
ring2-1 represents cyclopentane, cycloheptane, benzene, azetidine, tetrahydropyridine, or piperidine optionally substituted with $K-R^3$,
$R^{4-1}$ represents (1) chlorine, (2) piperidine, (3) tetrahydrothiopyran, (4) pyrrolidine, (5) morpholine (6) a C1-4 alkyl which is substituted with 1-5 substituent(s) selected from the group consisting of $NR^{4-101}$, $R^{4-102}$, $CO_2R^{4-103}$, $OR^{4-103}$, pyrrolidine, morpholine and pyridine, or (7) a C2-4 alkenyl which is substituted with substituent(s) selected from the group consisting of $NR^{4-101}$, $R^{4-102}$, $CO_2R^{4-103}$, $OR^{4-103}$, pyrrolidine, morpholine and pyridine;
the other symbols have the same meanings as described above [1],

[7] The compound as described above [1], which is
(1) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 6-(3-(dimethylamino)propyl)-7-(3-methoxyphenyl)-5-(4-phenoxyphenyl)pyrrolo[2,1-f][1,2,4]triazin-4-amine,
(3) 7-(3-methoxyphenyl)-5-(4-phenoxyphenyl)-6-(3-(pyrrolidin-1-yl)propyl)pyrrolo[2,1-f][1,2,4]triazin-4-amine,
(4) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(5) 5-[4-(3-chlorophenoxy)phenyl]-7-(3-methoxyphenyl)-6-(4-morpholinylmethyl)pyrrolo[2,1-f][1,2,4]triazin-4-amine,
(6) 5-[4-(3-chlorophenoxy)phenyl]-7-cyclopentyl-6-(4-morpholinylmethyl)pyrrolo[2,1-f][1,2,4]triazin-4-amine,
(7) 1-(4-(4-amino-5-(4-(3,4-dichlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(8) 1-(4-(4-amino-5-(4-(3-chlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(9) 7-cyclopentyl-5-(4-(3,4-dichlorophenoxy)-3-methoxyphenyl)-6-(2-(pyridin-3-yl)ethyl)pyrrolo[2,1-f][1,2,4]triazin-4-amine,
(10) 7-(3-methoxyphenyl)-5-(4-phenoxyphenyl)-6-[2-(3-pyridinyl)ethyl]pyrrolo[2,1-f][1,2,4]triazin-4-amine,
(11) 5-[4-(3,4-dichlorophenoxy)phenyl]-7-(3-methoxyphenyl)-6-[2-(3-pyridinyl)ethyl]pyrrolo[2,1-f][1,2,4]triazin-4-amine,
(12) 7-(3-methoxyphenyl)-5-(4-phenoxyphenyl)-6-(piperidin-4-yl)pyrrolo[2,1-f][1,2,4]triazin-4-amine,
(13) 7-cyclopentyl-5-(4-(3,4-dichlorophenoxy)-3-methoxyphenyl)-6-(piperidin-4-yl)pyrrolo[2,1-f][1,2,4]triazin-4-amine,
(14) 5-(4-(3-chlorophenoxy)-3-methoxyphenyl)-7-cyclopentyl-6-(piperidin-4-yl)pyrrolo[2,1-f][1,2,4]triazin-4-amine,
(15) 3-(4-(4-amino-7-cyclopentyl-6-(piperidin-4-yl)pyrrolo[2,1-f][1,2,4]triazin-5-yl)-2-methoxyphenoxy)benzonitrile,
(16) 5-[4-(3,4-dichlorophenoxy)-3-methoxy-phenyl]-7-(1-methylsulfonyl-4-piperidyl)-6-(4-piperidyl)pyrrolo[2,1-f][1,2,4]triazin-4-amine,
(17) 5-(4-(3-chlorophenoxy)-3-methoxyphenyl)-7-(1-(methylsulfonyl)piperidin-4-yl)-6-(piperidin-4-yl)pyrrolo[2,1-f][1,2,4]triazin-4-amine,
(18) (3-{4-amino-5-[4-(3-chlorophenoxy)-3-methoxyphenyl]-6-(4-pyridinyl)pyrrolo[2,1-f][1,2,4]triazin-7-yl}phenyl)(4-methyl-1-piperazinyl)methanone,
(19) 7-cycloheptyl-5-[4-(3,4-dichlorophenoxy)-3-methoxyphenyl]-6-(4-piperidinyl)pyrrolo[2,1-f][1,2,4]triazin-4-amine,
(20) 5-[4-(3-chlorophenoxy)-3-methoxyphenyl]-7-cycloheptyl-6-(4-piperidinyl)pyrrolo[2,1-f][1,2,4]triazin-4-amine,
(21) 5-[4-(3,4-dichlorophenoxy)-3-methoxyphenyl]-7-(3-methoxyphenyl)-6-(4-piperidinyl)pyrrolo[2,1-f][1,2,4]triazin-4-amine,
(22) 5-[4-(3-chlorophenoxy)-3-methoxyphenyl]-6-(3-methoxyphenyl)-6-(4-piperidinyl)pyrrolo[2,1-f][1,2,4]triazin-4-amine,
(23) N-(4-{4-amino-5-[4-(3-chlorophenoxy)-3-methoxyphenyl]-6-(4-piperidinyl)pyrrolo[2,1-f][1,2,4]triazin-7-yl}phenyl)-N-methylmethanesulfonamide,

(24) 5-[4-(3-chlorophenoxy)-3-methoxyphenyl]-7-(4-methoxyphenyl)-6-(4-piperidinyl)pyrrolo[2,1-f][1,2,4]triazin-4-amine,
(25) N-(4-{4-amino-5-[4-(3,4-dichlorophenoxy)-3-methoxyphenyl]-6-(4-piperidinyl)pyrrolo[2,1-f][1,2,4]triazin-7-yl}phenyl)-N-methylmethanesulfonamide,
(26) 3-{4-[4-amino-7-(4-methoxyphenyl)-6-(4-piperidinyl)pyrrolo[2,1-f][1,2,4]triazin-5-yl]-2-methoxyphenoxy}benzonitrile,
(27) 6-chloro-5-(4-(3-chlorophenoxy)-3-methoxyphenyl)-7-(1-(methylsulfonyl)piperidin-4-yl)pyrrolo[2,1-f][1,2,4]triazin-4-amine,
(28) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(29) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(30) 5-(4-(3-chlorophenoxy)-3-methoxyphenyl)-7-cyclopentyl-6-(pyrrolidin-3-yl)pyrrolo[2,1-f][1,2,4]triazin-4-amine,
(31) 5-[4-(3-chlorophenoxy)phenyl]-7-cyclopentyl-6-(2-ethoxyethyl)pyrrolo[2,1-f][1,2,4]triazin-4-amine,
(32) 3-{4-amino-5-[4-(3,4-dichlorophenoxy)-3-methoxyphenyl]-7-(3-methoxyphenyl)pyrrolo[2,1-f][1,2,4]triazin-6-yl}propanoic acid,
(33) {4-amino-7-cyclopentyl-5-[4-(3,4-dichlorophenoxy)-3-methoxyphenyl]pyrrolo[2,1-f][1,2,4]triazin-6-yl}acetic acid,
(34) 2-{4-amino-7-cyclopentyl-5-[4-(3,4-dichlorophenoxy)-3-methoxyphenyl]pyrrolo[2,1-f][1,2,4]triazin-6-yl}ethanol,
(35) methyl 4-amino-7-(3-methoxyphenyl)-5-(4-phenoxyphenyl)pyrrolo[2,1-f][1,2,4]triazine-6-carboxylate,
(36) 4-amino-7-(3-methoxyphenyl)-5-(4-phenoxyphenyl)pyrrolo[2,1-f][1,2,4]triazine-6-carboxylic acid,
(37) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(38) 4-amino-7-cyclopentyl-5-(4-phenoxyphenyl)pyrrolo[2,1-f][1,2,4]triazine-6-carboxylic acid,
(39) 3-{4-amino-5-[4-(3-chlorophenoxy)-3-methoxyphenyl]-7-(1-propen-2-yl)pyrrolo[2,1-f][1,2,4]triazin-6-yl}propanoic acid,
(40) (2E)-3-[4-amino-7-cyclopentyl-5-(4-phenoxyphenyl)pyrrolo[2,1-f][1,2,4]triazin-6-yl]acrylonitrile,
(41) methyl ({[4-amino-7-cyclopentyl-5-(4-phenoxyphenyl)pyrrolo[2,1-f][1,2,4]triazin-6-yl]carbonyl}amino)acetate,
(42) 6-fluoro-7-(3-methoxyphenyl)-5-(4-phenoxyphenyl)pyrrolo[2,1-f][1,2,4]triazin-4-amine,
(43) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(44) 3-[4-amino-7-cyclopentyl-5-(4-phenoxyphenyl)pyrrolo[2,1-f][1,2,4]triazin-6-yl]-2-methylacrylic acid,
(45) (2E)-3-{4-amino-7-cyclopentyl-5-[4-(3,4-dichlorophenoxy)-3-methoxyphenyl]pyrrolo[2,1-f][1,2,4]triazin-6-yl}acrylic acid,
(46) (2E)-3-[4-amino-7-cyclopentyl-5-(4-phenoxyphenyl)pyrrolo[2,1-f][1,2,4]triazin-6-yl]acrylamide,
(47) (2E)-3-[4-amino-7-cyclopentyl-5-(4-phenoxyphenyl)pyrrolo[2,1-f][1,2,4]triazin-6-yl]-2-propen-1-ol,
(48) 6-(2-aminoethyl)-7-cyclopentyl-5-(4-phenoxyphenyl)pyrrolo[2,1-f][1,2,4]triazin-4-amine,
(49) (2E)-3-[4-amino-7-cyclopentyl-5-(4-phenoxyphenyl)pyrrolo[2,1-f][1,2,4]triazin-6-yl]acrylohydrazide,
(50) 3-{4-amino-5-[4-(3,4-dichlorophenoxy)-3-methoxyphenyl]-7-(3-methoxyphenyl)pyrrolo[2,1-f][1,2,4]triazin-6-yl}propanamide,
(51) (2E)-1-(3-{4-amino-6-chloro-5-[4-(3,4-dichlorophenoxy)-3-methoxyphenyl]pyrrolo[2,1-f][1,2,4]triazin-7-yl}-1-piperidinyl)-4-(dimethylamino)-2-buten-1-one,
(52) 1-(3-{4-amino-6-chloro-5-[4-(3-chlorophenoxy)-3-methoxyphenyl]pyrrolo[2,1-f][1,2,4]triazin-7-yl}-1-pyrrolidinyl)-2-propen-1-one,
(53) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(54) 3-{4-amino-5-[4-(3-chlorophenoxy)-3-methoxyphenyl]-7-cyclopentylpyrrolo[2,1-f][1,2,4]triazin-6-yl}propanoic acid,
(55) 4-{4-amino-5-[4-(3-chlorophenoxy)-3-methoxyphenyl]-7-(3-methoxyphenyl)pyrrolo[2,1-f][1,2,4]triazin-6-yl}butanoic acid,
(56) 4-{4-amino-5-[4-(3,4-dichlorophenoxy)-3-methoxyphenyl]-7-(3-methoxyphenyl)pyrrolo[2,1-f][1,2,4]triazin-6-yl}butanoic acid,
(57) 3-(4-amino-5-[4-(3-chlorophenoxy)-3-methoxyphenyl]-7-{4-[(methylsulfonyl)amino]phenyl}pyrrolo[2,1-f][1,2,4]triazin-6-yl)propanoic acid,
(58) (2E)-3-[4-amino-7-(3-methoxyphenyl)-5-(4-phenoxyphenyl)pyrrolo[2,1-f][1,2,4]triazin-6-yl]acrylic acid,
(59) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(60) 5-[4-(3,4-dichlorophenoxy)-3-methoxyphenyl]-7-(3-methoxyphenyl)-6-[2-(1H-tetrazol-5-yl)ethyl]pyrrolo[2,1-f][1,2,4]triazin-4-amine,
(61) 3-{4-amino-5-[4-(3-chlorophenoxy)phenyl]-7-cyclopentylpyrrolo[2,1-f][1,2,4]triazin-6-yl}propanoic acid,
(62) 3-{4-amino-7-cyclopentyl-5-[4-(3,4-dichlorophenoxy)phenyl]pyrrolo[2,1-f][1,2,4]triazin-6-yl}propanoic acid,
(63) 3-{4-amino-7-cyclopentyl-5-[4-(3,4-dichlorophenoxy)-3-methoxyphenyl]pyrrolo[2,1-f][1,2,4]triazin-6-yl}propanoic acid,
(64) 3-(4-amino-7-cyclopentyl-5-{4-[3-(2-propanyl)phenoxy]phenyl}pyrrolo[2,1-f][1,2,4]triazin-6-yl)propanoic acid,
(65) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,
(66) 3-[4-amino-7-cyclopentyl-5-(4-phenoxyphenyl)pyrrolo[2,1-f][1,2,4]triazin-b-yl]propanoic acid,
(67) 3-[4-amino-7-cyclopentyl-5-(3-hydroxyphenyl)pyrrolo[2,1-f][1,2,4]triazin-6-yl]propanoic acid,
(68) 1-(3-{4-amino-6-chloro-5-[4-(3-chlorophenoxy)-3-hydroxyphenyl]pyrrolo[2,1-f][1,2,4]triazin-7-yl}-1-piperidinyl)-2-propen-1-one,
(69) 3-{4-amino-5-[4-(3-chlorophenoxy)-3-methoxyphenyl]-7-(3-methoxyphenyl)pyrrolo[2,1-f][1,2,4]triazin-6-yl}propanoic acid,
(70) 3-{4-amino-5-[4-(3-chlorophenoxy)-3-methoxyphenyl]-7-(4-methoxyphenyl)pyrrolo[2,1-f][1,2,4]triazin-6-yl}propanoic acid,
(71) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(72) 3-{4-amino-5-[4-(3-chlorophenoxy)-3-methoxyphenyl]-7-phenylpyrrolo[2,1-f][1,2,4]triazin-6-yl}propanoic acid,
(73) 3-{4-amino-5-[4-(3-chlorophenoxy)-3-methoxyphenyl]-7-(2-fluorophenyl)pyrrolo[2,1-f][1,2,4]triazin-6-yl}propanoic acid,

(74) 3-{4-amino-5-[4-(3-chlorophenoxy)-3-methoxyphenyl]-7-(3-fluorophenyl)pyrrolo[2,1-f][1,2,4]triazin-6-yl}propanoic acid,
(75) 3-{4-amino-5-[4-(3-chlorophenoxy)-3-methoxyphenyl]-7-(4-fluorophenyl)pyrrolo[2,1-f][1,2,4]triazin-6-yl}propanoic acid,
(76) 3-{4-amino-7-cyclopentyl-5-[4-(3,5-difluorophenoxy)-3-methoxyphenyl]pyrrolo[2,1-f][1,2,4]triazin-6-yl}propanoic acid,
(77) 3-{4-amino-7-cyclopentyl-5-[4-(3,5-dichlorophenoxy)-3-methoxyphenyl]pyrrolo[2,1-f][1,2,4]triazin-6-yl}propanoic acid,
(78) 3-{4-amino-7-(3-carbamoylphenyl)-5-[4-(3-chlorophenoxy)-3-methoxyphenyl]pyrrolo[2,1-f][1,2,4]triazin-6-yl}propanoic acid,
(79) 3-{4-amino-7-cyclopentyl-5-[4-(3,5-difluorophenoxy)phenyl]pyrrolo[2,1-f][1,2,4]triazin-6-yl}propanoic acid,
(80) 3-{4-amino-7-cyclopentyl-5-[4-(3,5-dichlorophenoxy)phenyl]pyrrolo[2,1-f][1,2,4]triazin-6-yl}propanoic acid,
(81) (2E)-3-[4-amino-7-cyclopentyl-5-(4-phenoxyphenyl)pyrrolo[2,1-f][1,2,4]triazin-6-yl]acrylic acid,
(82) 3-{4-amino-5-[4-(3-chlorophenoxy)-3-methoxyphenyl]-7-(2-hydroxy-2-propanyl)pyrrolo[2,1-f][1,2,4]triazin-6-yl}propanoic acid,
(83) ({[4-amino-7-cyclopentyl-5-(4-phenoxyphenyl)pyrrolo[2,1-f][1,2,4]triazin-6-yl]carbonyl}amino)acetic acid,
(84) 3-(4-amino-5-[4-(3-chlorophenoxy)-3-methoxyphenyl]-7-{4-[methyl(methylsulfonyl)amino]phenyl}pyrrolo[2,1-f][1,2,4]triazin-6-yl)propanoic acid,
(85) 3-{4-amino-5-[4-(3-chlorophenoxy)-3-methoxyphenyl]-7-[4-(methylsulfonyl)phenyl]pyrrolo[2,1-f][1,2,4]triazin-6-yl}propanoic acid,
(86) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one,
(87) 3-[4-amino-7-{4-[methyl(methylsulfonyl)amino]phenyl}-5-(4-phenoxyphenyl)pyrrolo[2,1-f][1,2,4]triazin-6-yl]propanoic acid,
(88) (2E)-3-[4-amino-7-(2-hydroxy-2-propanyl)-5-(4-phenoxyphenyl)pyrrolo[2,1-f][1,2,4]triazin-6-yl]acrylic acid,
(89) 3-(4-amino-7-cyclopentyl-5-{3-methoxy-4-[3-(2-propanyl)phenoxy]phenyl}pyrrolo[2,1-f][1,2,4]triazin-6-yl)propanoic acid,
(90) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid,
(91) (2E)-3-{4-amino-7-[1-(methylsulfonyl)-4-piperidinyl]-5-(4-phenoxyphenyl)pyrrolo[2,1-f][1,2,4]triazin-6-yl}acrylic acid,
(92) (2E)-3-[4-amino-7-cyclopentyl-5-(2-fluoro-4-phenoxyphenyl)pyrrolo[2,1-f][1,2,4]triazin-6-yl]acrylic acid,
(93) 3-[4-amino-7-(3-methoxyphenyl)-5-(4-phenoxyphenyl)pyrrolo[2,1-f][1,2,4]triazin-6-yl]propanoic acid,
(94) (2E)-3-[4-amino-7-cyclohexyl-5-(4-phenoxyphenyl)pyrrolo[2,1-f][1,2,4]triazin-6-yl]acrylic acid,
(95) (2E)-3-[4-amino-7-(1,1-dioxidotetrahydro-2H-thiopyran-4-yl)-5-(4-phenoxyphenyl)pyrrolo[2,1-f][1,2,4]triazin-6-yl]acrylic acid,
(96) (2E)-3-(4-amino-7-cyclopentyl-5-{4-[3-(2-propanyl)phenoxy]phenyl}pyrrolo[2,1-f][1,2,4]triazin-6-yl)acrylic acid,
(97) (2E)-3-{4-amino-5-[4-(3-chlorophenoxy)-3-methoxyphenyl]-7-cyclopentylpyrrolo[2,1-f][1,2,4]triazin-6-yl}acrylic acid,
(98) (2E)-3-[4-amino-5-(4-phenoxyphenyl)-7-(tetrahydro-2H-pyran-4-yl)pyrrolo[2,1-f][1,2,4]triazin-6-yl]acrylic acid,
(99) (2E)-3-[4-amino-7-(3-hydroxy-3-methylbutyl)-5-(4-phenoxyphenyl)pyrrolo[2,1-f][1,2,4]triazin-6-yl]acrylic acid,
(100) (2E)-3-[4-amino-7-isopropyl-5-(4-phenoxyphenyl)pyrrolo[2,1-f][1,2,4]triazin-6-yl]acrylic acid,
(101) N-{2-[4-amino-7-cyclopentyl-5-(4-phenoxyphenyl)pyrrolo[2,1-f][1,2,4]triazin-6-yl]ethyl}acetamide,
(102) 1-[4-amino-7-cyclopentyl-5-(4-phenoxyphenyl)pyrrolo[2,1-f][1,2,4]triazin-6-yl]-1,2-ethanediol,
(103) 4-[4-amino-7-cyclopentyl-5-(4-phenoxyphenyl)pyrrolo[2,1-f][1,2,4]triazin-6-yl]-1-hydroxy-2-butanone,
(104) 4-amino-7-cyclopentyl-N-(2-hydroxyethyl)-5-(4-phenoxyphenyl)pyrrolo[2,1-f][1,2,4]triazine-6-carboxamide,
(105) 4-amino-7-cyclopentyl-5-(4-phenoxyphenyl)-N-(1H-pyrazol-4-yl)pyrrolo[2,1-f][1,2,4]triazine-6-carboxamide,
(106) 4-amino-7-cyclopentyl-5-(4-phenoxyphenyl)-N-(1H-pyrazol-3-yl)pyrrolo[2,1-f][1,2,4]triazine-6-carboxamide,
(107) (2E)-3-[4-amino-7-cyclopentyl-5-(4-phenoxyphenyl)pyrrolo[2,1-f][1,2,4]triazin-6-yl]acrylamide,
(108) 4-amino-7-cyclopentyl-N-(2-methoxyethyl)-5-(4-phenoxyphenyl)pyrrolo[2,1-f][1,2,4]triazine-6-carboxamide,
(109) 4-amino-7-cyclopentyl-5-(4-phenoxyphenyl)pyrrolo[2,1-f][1,2,4]triazine-6-carbohydrazide,
(110) 4-amino-7-cyclopentyl-N-[2-(dimethylamino)ethyl]-5-(4-phenoxyphenyl)pyrrolo[2,1-f][1,2,4]triazine-6-carboxamide,
(111) (2E)-3-[4-amino-7-cyclopentyl-5-(4-phenoxyphenyl)pyrrolo[2,1-f][1,2,4]triazin-6-yl]-N-(1H-pyrazol-4-yl)acrylamide, or
(112) 4-amino-7-cyclopentyl-5-(4-phenoxyphenyl)pyrrolo[2,1-f][1,2,4]triazine-6-carboxamide,

[8] The compound as described above [1], which is
(1) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(3) 7-cycloheptyl-5-(4-(3,4-dichlorophenoxy)-3-methoxyphenyl)-6-(piperidin-4-yl)pyrrolo[2,1-f][1,2,4]triazin-4-amine,
(4) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(5) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(6) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(7) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(8) 1-(3-{4-amino-6-chloro-5-[4-(3-chlorophenoxy)-3-methoxyphenyl]pyrrolo[2,1-f][1,2,4]triazin-7-yl}-1-pyrrolidinyl)-2-propen-1-one,
(9) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(10) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(11) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,

(12) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(13) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one, or
(14) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid,

[9] A pharmaceutical composition comprising the compound represented by formula (I) of above [1], a salt thereof, a solvate thereof, an N-oxide thereof or a prodrug thereof,

[10] A method for preventing and/or treating a Btk related disease, which comprises administering to a mammal an effective amount of the compound of formula (I) of above [1], a salt thereof, a solvate thereof, an N-oxide thereof or a prodrug thereof

[11] A method for preventing and/or treating a Btk related disease, which comprises administering to a mammal an effective amount of a compound of formula (I) of above [1] that is selective for Btk over Lek, a salt thereof, a solvate thereof, an N-oxide thereof or a prodrug thereof,

[12] The method as described above [10], wherein the Btk related disease is an allergic disease, an autoimmune disease, an inflammatory disease, a thromboembolic disease, or cancer,

[13] The method as described above [12], wherein the autoimmune disease is rheumatoid arthritis,

[14] The method as described above [12], wherein the cancer is a B cell lymphoma,

[15] Use of the compound of formula (I) of above [1], a salt thereof, a solvate thereof, an N-oxide thereof or a prodrug thereof, for the manufacture of an agent for preventing and/or treating a Btk related disease, and

[16] A compound of formula (I) of above [1], a salt thereof, a solvate thereof, an N-oxide thereof or a prodrug thereof, for preventing and/or treating a Btk related disease.

In the present invention, halogen includes chlorine, fluorine, bromine, and iodine.

In the present invention, C1-4 alkyl includes straight and branched chain C1-4 alkyl group, such as methyl, ethyl, n-propyl, isopropyl, n-butyl, isobutyl, sec-butyl, and tert-butyl.

In the present invention, C1-4 alkylene includes, such as methylene, ethylene, trimethylene, tetramethylene and isomer thereof.

In the present invention, C2-4 alkenyl includes straight and branched chain C1-4 alkenyl group, such as ethenyl, 1-propenyl, 2-propenyl, 1-butenyl, 2-butenyl, and 3-butenyl.

In the present invention, C1-4 alkoxy includes, such as methoxy, ethoxy, propoxy, isopropoxy, butoxy, isobutoxy, sec-butoxy, and tert-butoxy.

In the present invention, C4-7 carbocyclic ring includes, such as cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, and benzene.

In the present invention, C5-7 carbocyclic ring includes, such as cyclopentane, cyclohexane, cycloheptane, cyclopentene, cyclohexene, cycloheptene, cyclopentadiene, cyclohexadiene, cycloheptadiene, and benzene.

In the present invention, 5-10 membered heterocyclic ring includes, for example, 5-10 membered aromatic monocyclic or bicyclic aromatic heterocyclic ring containing 1-4 heteroatoms selected from a nitrogen atom, an oxygen atom and/or a sulfur atom optionally oxidized, and includes a monocyclic aromatic heterocyclic ring, a bicyclic aromatic heterocyclic ring, a bicyclic fused ring formed of a monocyclic aromatic heterocyclic ring and an unsaturated or saturated monocyclic carbocyclic ring, a bicyclic fused ring formed of a monocyclic aromatic carbocyclic ring and an unsaturated or saturated monocyclic heterocyclic ring, or a bicyclic fused ring formed of a monocyclic aromatic heterocyclic ring and an unsaturated or saturated monocyclic heterocyclic ring are included therein. For example, pyrrole, imidazole, triazole, pyrazole, pyridine, pyrazine, pyrimidine, pyridazine, furan, thiophene, oxazole, isooxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzooxazole, benzothiazole, benzoimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chromane, isochromane, tetrahydroquinoline, dihydroquinoline, tetrahydroisoquinoline, dihydroisoquinoline, tetrahydroquinoxaline, dihydroquinoxaline, tetrahydroquinazoline, dihydroquinazoline, and dioxaindan rings are given. However, in the case of the indole, isoindole, benzofuran, isobenzofuran, benzothiophene, isobenzothiophene, indazole, phthalazine, quinoxaline, quinazoline, cinnoline, benzooxazole, benzothiazole, benzoimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chromane, isochromane, and dioxaindan rings, a benzene ring among those rings, or in the case of tetrahydroquinoline, dihydroquinoline, tetrahydroisoquinoline, dihydroisoquinoline, tetrahydroquinoxaline, dihydroquinoxaline, tetrahydroquinazoline, and dihydroquinazoline rings, a pyridine, pyrimidine or pyrazine ring among those rings binds to L in the formula (I).

In the present invention, 4-7 member heterocyclic ring includes, for example, 4-7 membered monocyclic unsaturated or saturated heterocyclic ring containing 1-4 heteroatoms selected from a nitrogen atom, an oxygen atom and/or a sulfur atom optionally oxidized. Such as azetidine, oxetane, thietane, pyrrole, imidazole, triazole, pyrazole, pyridine, pyrazine, pyrimidine, pyridazine, azepine, diazepine, furan, pyran, oxepine, thiophene, thiopyran, thiepine, oxazole, isoxazole, thiazole, thiazole, isothiazole, furazan, oxadiazole, oxazine, oxadiazine, oxazepine, oxadiazepine, thiadiazole, thiazine, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, and the like.

In the present invention, 5-7 membered heterocyclic ring includes, for example, 5-7 membered monocyclic unsaturated or saturated heterocyclic ring containing 1-4 heteroatoms selected from a nitrogen atom, an oxygen atom and/or a sulfur atom optionally oxidized. Such as pyrrole, imidazole, triazole, pyrazole, pyridine, pyrazine, pyrimidine, pyridazine, azepine, diazepine, furan, pyran, oxepine, thiophene, thiopyran, thiepine, oxazole, isoxazole, thiazole, thiazole, isothiazole, furazan, oxadiazole, oxazine, oxadiazine, oxazepine, oxadiazepine, thiadiazole, thiazine, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, and the like.

In the present invention, 5-7 membered heterocyclic ring also includes the 5-7 membered monocyclic unsaturated or saturated nitrogen-containing heterocyclic ring, which means 5-7 membered heterocyclic necessarily containing 1-4 nitrogen atom(s) among above described recited 5-7 membered heterocyclic ring. Such as pyrrole, imidazole, triazole, pyrazole, pyridine, pyrazine, pyrimidine, pyridazine, azepine, diazepine, oxazole, isoxazole, thiazole, thiazole, isothiazole, furazan, oxadiazole, oxazine, oxadiazine, oxazepine, oxadiazepine, thiadiazole, thiazine, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, and the like.

In the present invention, ring1 is preferably cyclopentane, benzene, thiazole, indole, or benzothiazole, more preferably benzene.

In the present invention, the substituent of ring1 is preferably fluorine, chlorine, methyl, $CF_3$, or nitrile, more preferably chlorine.

In the present invention, L is preferably —O—.

In the present invention, $R^1$ is preferably C1-4 alkoxy, more preferably methoxy.

In the present invention, $R^2$ is preferably ring 2, which is preferably cyclopentyl, cyclohexyl, cycloheptyl, phenyl, azetidine, pyrrolidine, piperidine, perhydroazepine, morpholine, piperazine, pyran, thiopyran, dihydropyridine, pyridine, pyrazole, isoindoline, or perhydroisoquinoline, more preferably benzene, cyclopentane, cycloheptane, or piperidine, more preferably azetidine, tetrahydropyridine, piperidine, pyrrolidine, phenyl, or cycloheptane.

In the present invention, K is preferably bond, —O—, —C(O)CH$_2$—, —SO$_2$—, or —C(O)—, more preferably —O—, —C(O)—.

In the present invention, $R^3$ is preferably $NR^{3-101}R^{3-102}$, C1-4 alkyl, or C2-4 alkenyl, more preferably dimethylamine, diethylamine, N-methylmethanesulfonamide, methyl, ethyl, or ethenyl.

In the present invention, halogen atom in $R^4$ is preferably chlorine.

In the present invention, ring3 in $R^4$ is preferably pyrrolidine, piperidine, morpholine, imidazole, tetrahydrothiopyran, or pyridine, more preferably pyrrolidine, piperidine, morpholine, or tetrahydrothiopyran.

In the present invention, ring4 in $R^4$ is preferably 5-7 membered monocyclic unsaturated or saturated nitrogen-containing heterocyclic ring, more preferably pyrrolidine, piperidine, tetrahydropyran, morpholine, imidazole, tetrazole, tetrahydrothiopyran, or pyridine, further preferably pyrrolidine, morpholine, or pyridine.

In the present invention, ring 5 is preferably pyrazole.

In the present invention, $R^4$ is preferably (1) chlorine, (2) piperidine, (3) tetrahydrothiopyran, (4) pyrrolidine, (5) morpholine (6) C1-4 alkyl substituted with $NR^{4-1}R^{4-2}$, $CO_2R^{4-103}$, $OR^{4-103}$, pyrrolidine, morpholine or pyridine, or (7) C2-4 alkenyl substituted with $NR^{4-1}R^{4-2}$, $CO_2R^{4-103}$, $OR^{4-103}$, pyrrolidine, morpholine or pyridine.

In the present invention, the compound represented by formula (I) is preferably the compound represented by formula (I-1)

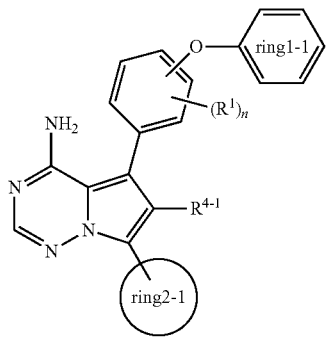

(I-1)

wherein all the symbols have the same meanings as the above.

In the present invention, the compounds described in Examples are preferred. It recites (1) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 6-(3-(dimethylamino)propyl)-7-(3-methoxyphenyl)-5-(4-phenoxyphenyl)pyrrolo[2,1-f][1,2,4]triazin-4-amine,
(3) 7-(3-methoxyphenyl)-5-(4-phenoxyphenyl)-6-(3-(pyrrolidin-1-yl)propyl)pyrrolo[2,1-f][1,2,4]triazin-4-amine,
(4) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(5) 5-[4-(3-chlorophenoxy)phenyl]-7-(3-methoxyphenyl)-6-(4-morpholinylmethyl)pyrrolo[2,1-f][1,2,4]triazin-4-amine,
(6) 5-[4-(3-chlorophenoxy)phenyl]-7-cyclopentyl-6-(4-morpholinylmethyl)pyrrolo[2,1-f][1,2,4]triazin-4-amine,
(7) 1-(4-(4-amino-5-(4-(3,4-dichlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(8) 1-(4-(4-amino-5-(4-(3-chlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(9) 7-cyclopentyl-5-(4-(3,4-dichlorophenoxy)-3-methoxyphenyl)-6-(2-(pyridin-3-yl)ethyl)pyrrolo[2,1-f][1,2,4]triazin-4-amine,
(10) 7-(3-methoxyphenyl)-5-(4-phenoxyphenyl)-6-[2-(3-pyridinyl)ethyl]pyrrolo[2,1-f][1,2,4]triazin-4-amine,
(11) 5-[4-(3,4-dichlorophenoxy)phenyl]-7-(3-methoxyphenyl)-6-[2-(3-pyridinyl)ethyl]pyrrolo[2,1-f][1,2,4]triazin-4-amine,
(12) 7-(3-methoxyphenyl)-5-(4-phenoxyphenyl)-6-(piperidin-4-yl)pyrrolo[2,1-f][1,2,4]triazin-4-amine,
(13) 7-cyclopentyl-5-(4-(3,4-dichlorophenoxy)-3-methoxyphenyl)-6-(piperidin-4-yl)pyrrolo[2,1-f][1,2,4]triazin-4-amine,
(14) 5-(4-(3-chlorophenoxy)-3-methoxyphenyl)-7-cyclopentyl-6-(piperidin-4-yl)pyrrolo[2,1-f][1,2,4]triazin-4-amine,
(15) 3-(4-(4-amino-7-cyclopentyl-6-(piperidin-4-yl)pyrrolo[2,1-f][1,2,4]triazin-5-yl)-2-methoxyphenoxy)benzonitrile,
(16) 5-[4-(3,4-dichlorophenoxy)-3-methoxy-phenyl]-7-(1-methylsulfonyl-4-piperidyl)-6-(4-piperidyl)pyrrolo[2,1-f][1,2,4]triazin-4-amine,
(17) 5-(4-(3-chlorophenoxy)-3-methoxyphenyl)-7-(1-(methylsulfonyl)piperidin-4-yl)-6-(piperidin-4-yl)pyrrolo[2,1-f][1,2,4]triazin-4-amine,
(18) (3-{4-amino-5-[4-(3-chlorophenoxy)-3-methoxyphenyl]-6-(4-pyridinyl)pyrrolo[2,1-f][1,2,4]triazin-7-yl}phenyl)(4-methyl-1-piperazinyl)methanone,
(19) 7-cycloheptyl-5-[4-(3,4-dichlorophenoxy)-3-methoxyphenyl]-6-(4-piperidinyl)pyrrolo[2,1-f][1,2,4]triazin-4-amine,
(20) 5-[4-(3-chlorophenoxy)-3-methoxyphenyl]-7-cycloheptyl-6-(4-piperidinyl)pyrrolo[2,1-f][1,2,4]triazin-4-amine,
(21) 5-[4-(3,4-dichlorophenoxy)-3-methoxyphenyl]-7-(3-methoxyphenyl)-6-(4-piperidinyl)pyrrolo[2,1-f][1,2,4]triazin-4-amine,
(22) 5-[4-(3-chlorophenoxy)-3-methoxyphenyl]-7-(3-methoxyphenyl)-6-(4-piperidinyl)pyrrolo[2,1-f][1,2,4]triazin-4-amine,
(23) N-(4-{4-amino-5-[4-(3-chlorophenoxy)-3-methoxyphenyl]-6-(4-piperidinyl)pyrrolo[2,1-f][1,2,4]triazin-7-yl}phenyl)-N-methylmethanesulfonamide,
(24) 5-[4-(3-chlorophenoxy)-3-methoxyphenyl]-7-(4-methoxyphenyl)-6-(4-piperidinyl)pyrrolo[2,1-f][1,2,4]triazin-4-amine,
(25) N-(4-{4-amino-5-[4-(3,4-dichlorophenoxy)-3-methoxyphenyl]-6-(4-piperidinyl)pyrrolo[2,1-f][1,2,4]triazin-7-yl}phenyl)-N-methylmethanesulfonamide,
(26) 3-{4-[4-amino-7-(4-methoxyphenyl)-6-(4-piperidinyl)pyrrolo[2,1-f][1,2,4]triazin-5-yl]-2-methoxyphenoxy}benzonitrile,
(27) 6-chloro-5-(4-(3-chlorophenoxy)-3-methoxyphenyl)-7-(1-(methylsulfonyl)piperidin-4-yl)pyrrolo[2,1-f][1,2,4]triazin-4-amine,
(28) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(29) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(30) 5-(4-(3-Chlorophenoxy)-3-methoxyphenyl)-7-cyclopentyl-6-(tetrahydro-2H-pyran-4-yl)pyrrolo[2,1-f][1,2,4]triazin-4-amine,
(31) 5-(4-(3-Chlorophenoxy)-3-methoxyphenyl)-7-cyclopentyl-6-(tetrahydro-2H-thiopyran-1,1-dioxide-4-yl)pyrrolo[2,1-f][1,2,4]triazin-4-amine,
(32) 5-(4-(4-Chloro-3-(trifluoromethyl)phenoxy)-3-methoxyphenyl)-7-cyclopentyl-6-(tetrahydro-2H-pyran-4-yl)pyrrolo[2,1-f][1,2,4]triazin-4-amine,
(33) 3-(4-(4-Amino-7-cyclopentyl-6-(tetrahydro-2H-pyran-4-yl)pyrrolo[2,1-f][1,2,4]triazin-5-yl)-2-methoxyphenoxy)benzonitrile,
(34) 7-cyclopentyl-5-[4-(3,4-dichlorophenoxy)-3-methoxyphenyl]-6-(1,1-dioxidotetrahydro-2H-thiopyran-4-yl)pyrrolo[2,1-f][1,2,4]triazin-4-amine,
(35) 3-{-4-[4-amino-7-cyclopentyl-6-(1,1-dioxidotetrahydro-2H-thiopyran-4-yl)pyrrolo[2,1-f][1,2,4]triazin-5-yl]-2-methoxyphenoxy}benzonitrile,
(36) 5-{4-[4-chloro-3-(trifluoromethyl)phenoxy]-3-methoxyphenyl}-7-cyclopentyl-6-(1,1-dioxidotetrahydro-2H-thiopyran-4-yl)pyrrolo[2,1-f][1,2,4]triazin-4-amine,
(37) 5-(4-(3-chlorophenoxy)-3-methoxyphenyl)-7-cyclopentyl-6-(pyrrolidin-3-yl)pyrrolo[2,1-f][1,2,4]triazin-4-amine,
(38) 5-[4-(3-chlorophenoxy)phenyl]-7-cyclopentyl-6-(2-ethoxyethyl)pyrrolo[2,1-f][1,2,4]triazin-4-amine,

(39) 3-{4-amino-5-[4-(3,4-dichlorophenoxy)-3-methoxyphenyl]-7-(3-methoxyphenyl)pyrrolo[2,1-f][1,2,4]triazin-6-yl}propanoic acid,
(40) {4-amino-7-cyclopentyl-5-[4-(3,4-dichlorophenoxy)-3-methoxyphenyl]pyrrolo[2,1-f][1,2,4]triazin-6-yl}acetic acid,
(41) 2-{4-amino-7-cyclopentyl-5-[4-(3,4-dichlorophenoxy)-3-methoxyphenyl]pyrrolo[2,1-f][1,2,4]triazin-6-yl}ethanol,
(42) methyl 4-amino-7-(3-methoxyphenyl)-5-(4-phenoxyphenyl)pyrrolo[2,1-f][1,2,4]triazine-6-carboxylate,
(43) 4-amino-7-(3-methoxyphenyl)-5-(4-phenoxyphenyl)pyrrolo[2,1-f][1,2,4]triazine-6-carboxylic acid,
(44) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(45) 4-amino-7-cyclopentyl-5-(4-phenoxyphenyl)pyrrolo[2,1-f][1,2,4]triazine-6-carboxylic acid,
(46) 3-{4-amino-5-[4-(3-chlorophenoxy)-3-methoxyphenyl]-7-(1-propen-2-yl)pyrrolo[2,1-f][1,2,4]triazin-6-yl}propanoic acid,
(47) (2E)-3-[4-amino-7-cyclopentyl-5-(4-phenoxyphenyl)pyrrolo[2,1-f][1,2,4]triazin-6-yl]acrylonitrile,
(48) methyl ({[4-amino-7-cyclopentyl-5-(4-phenoxyphenyl)pyrrolo[2,1-f][1,2,4]triazin-6-yl]carbonyl}amino)acetate,
(49) 6-fluoro-7-(3-methoxyphenyl)-5-(4-phenoxyphenyl)pyrrolo[2,1-f][1,2,4]triazin-4-amine,
(50) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(51) 3-[4-amino-7-cyclopentyl-5-(4-phenoxyphenyl)pyrrolo[2,1-f][1,2,4]triazin-6-yl]-2-methylacrylic acid,
(52) (2E)-3-{4-amino-7-cyclopentyl-5-[4-(3,4-dichlorophenoxy)-3-methoxyphenyl]pyrrolo[2,1-f][1,2,4]triazin-6-yl}acrylic acid,
(53) (2E)-3-[4-amino-7-cyclopentyl-5-(4-phenoxyphenyl)pyrrolo[2,1-f][1,2,4]triazin-6-yl]acrylamide,
(54) (2E)-3-[4-amino-7-cyclopentyl-5-(4-phenoxyphenyl)pyrrolo[2,1-f][1,2,4]triazin-6-yl]-2-propen-1-al,
(55) 6-(2-aminoethyl)-7-cyclopentyl-5-(4-phenoxyphenyl)pyrrolo[2,1-f][1,2,4]triazin-4-amine,
(56) (2E)-3-[4-amino-7-cyclopentyl-5-(4-phenoxyphenyl)pyrrolo[2,1-f][1,2,4]triazin-6-yl]acrylohydrazide,
(57) 3-{4-amino-5-[4-(3,4-dichlorophenoxy)-3-methoxyphenyl]-7-(3-methoxyphenyl)pyrrolo[2,1-f][1,2,4]triazin-6-yl}propanamide,
(58) (2E)-1-(3-{4-amino-6-chloro-5-[4-(3,4-dichlorophenoxy)-3-methoxyphenyl]pyrrolo[2,1-f][1,2,4]triazin-7-yl}-1-piperidinyl)-4-(dimethylamino)-2-buten-1-one,
(59) 1-(3-{4-amino-6-chloro-5-[4-(3-chlorophenoxy)-3-methoxyphenyl]pyrrolo[2,1-f][1,2,4]triazin-7-yl}-1-pyrrolidinyl)-2-propen-1-one,
(60) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(61) 3-{4-amino-5-[4-(3-chlorophenoxy)-3-methoxyphenyl]-7-cyclopentylpyrrolo[2,1-f][1,2,4]triazin-6-yl}propanoic acid,
(62) 4-{4-amino-5-[4-(3-chlorophenoxy)-3-methoxyphenyl]-7-(3-methoxyphenyl)pyrrolo[2,1-f][1,2,4]triazin-6-yl}butanoic acid,
(63) 4-{4-amino-5-[4-(3,4-dichlorophenoxy)-3-methoxyphenyl]-7-(3-methoxyphenyl)pyrrolo[2,1-f][1,2,4]triazin-6-yl}butanoic acid,
(64) 3-(4-amino-5-[4-(3-chlorophenoxy)-3-methoxyphenyl]-7-{4-[(methylsulfonyl)amino]phenyl}pyrrolo[2,1-f][1,2,4]triazin-6-yl)propanoic acid,
(65) (2E)-3-[4-amino-7-(3-methoxyphenyl)-5-(4-phenoxyphenyl)pyrrolo[2,1-f][1,2,4]triazin-6-yl]acrylic acid,
(66) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(67) 5-[4-(3,4-dichlorophenoxy)-3-methoxyphenyl]-7-(3-methoxyphenyl)-6-[2-(1H-tetrazol-5-yl)ethyl]pyrrolo[2,1-f][1,2,4]triazin-4-amine,
(68) 3-{4-amino-5-[4-(3-chlorophenoxy)phenyl]-7-cyclopentylpyrrolo[2,1-f][1,2,4]triazin-6-yl}propanoic acid,
(69) 3-{4-amino-7-cyclopentyl-5-[4-(3,4-dichlorophenoxy)phenyl]pyrrolo[2,1-f][1,2,4]triazin-6-yl}propanoic acid,
(70) 3-{4-amino-7-cyclopentyl-5-[4-(3,4-dichlorophenoxy)-3-methoxyphenyl]pyrrolo[2,1-f][1,2,4]triazin-6-yl}propanoic acid,
(71) 3-(4-amino-7-cyclopentyl-5-{4-[3-(2-propanyl)phenoxy]phenyl}pyrrolo[2,1-f][1,2,4]triazin-6-yl)propanoic acid,
(72) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,
(73) 3-[4-amino-7-cyclopentyl-5-(4-phenoxyphenyl)pyrrolo[2,1-f][1,2,4]triazin-6-yl]propanoic acid,
(74) 3-[4-amino-7-cyclopentyl-5-(3-hydroxyphenyl)pyrrolo[2,1-f][1,2,4]triazin-6-yl]propanoic acid,
(75) 1-(3-{4-amino-6-chloro-5-[4-(3-chlorophenoxy)-3-hydroxyphenyl]pyrrolo[2,1-f][1,2,4]triazin-7-yl}-1-piperidinyl)-2-propen-1-one,
(76) 3-{4-amino-5-[4-(3-chlorophenoxy)-3-methoxyphenyl]-7-(3-methoxyphenyl)pyrrolo[2,1-f][1,2,4]triazin-6-yl}propanoic acid,
(77) 3-{4-amino-5-[4-(3-chlorophenoxy)-3-methoxyphenyl]-7-(4-methoxyphenyl)pyrrolo[2,1-f][1,2,4]triazin-6-yl}propanoic acid,
(78) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(79) 3-{4-amino-5-[4-(3-chlorophenoxy)-3-methoxyphenyl]-7-phenylpyrrolo[2,1-f][1,2,4]triazin-6-yl}propanoic acid,
(80) 3-{4-amino-5-[4-(3-chlorophenoxy)-3-methoxyphenyl]-7-(2-fluorophenyl)pyrrolo[2,1-f][1,2,4]triazin-6-yl}propanoic acid,
(81) 3-{4-amino-5-[4-(3-chlorophenoxy)-3-methoxyphenyl]-7-(3-fluorophenyl)pyrrolo[2,1-f][1,2,4]triazin-6-yl}propanoic acid,
(82) 3-{4-amino-5-[4-(3-chlorophenoxy)-3-methoxyphenyl]-7-(4-fluorophenyl)pyrrolo[2,1-f][1,2,4]triazin-6-yl}propanoic acid,
(83) 3-{4-amino-7-cyclopentyl-5-[4-(3,5-difluorophenoxy)-3-methoxyphenyl]pyrrolo[2,1-f][1,2,4]triazin-6-yl}propanoic acid,
(84) 3-{4-amino-7-cyclopentyl-5-[4-(3,5-dichlorophenoxy)-3-methoxyphenyl]pyrrolo[2,1-f][1,2,4]triazin-6-yl}propanoic acid,
(85) 3-{4-amino-7-(3-carbamoylphenyl)-5-[4-(3-chlorophenoxy)-3-methoxyphenyl]pyrrolo[2,1-f][1,2,4]triazin-6-yl}propanoic acid,
(86) 3-{4-amino-7-cyclopentyl-5-[4-(3,5-difluorophenoxy)phenyl]pyrrolo[2,1-f][1,2,4]triazin-6-yl}propanoic acid,
(87) 3-{4-amino-7-cyclopentyl-5-[4-(3,5-dichlorophenoxy)phenyl]pyrrolo[2,1-f][1,2,4]triazin-6-yl}propanoic acid,
(88) (2E)-3-[4-amino-7-cyclopentyl-5-(4-phenoxyphenyl)pyrrolo[2,1-f][1,2,4]triazin-6-yl]acrylic acid,
(89) 3-{4-amino-5-[4-(3-chlorophenoxy)-3-methoxyphenyl]-7-(2-hydroxy-2-propanyl)pyrrolo[2,1-f][1,2,4]triazin-6-yl}propanoic acid,

(90) ({[4-amino-7-cyclopentyl-5-(4-phenoxyphenyl)pyrrolo[2,1-f][1,2,4]triazin-6-yl]carbonyl}amino)acetic acid,
(91) 3-(4-amino-5-[4-(3-chlorophenoxy)-3-methoxyphenyl]-7-{4-[methyl(methylsulfonyl)amino]phenyl}pyrrolo[2,1-f][1,2,4]triazin-6-yl)propanoic acid,
(92) 3-{4-amino-5-[4-(3-chlorophenoxy)-3-methoxyphenyl]-7-[4-(methylsulfonyl)phenyl]pyrrolo[2,1-f][1,2,4]triazin-6-yl}propanoic acid,
(93) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one,
(94) 3-[4-amino-7-{-4-[methyl(methylsulfonyl)amino]phenyl}-5-(4-phenoxyphenyl)pyrrolo[2,1-f][1,2,4]triazin-6-yl]propanoic acid,
(95) (2E)-3-[4-amino-7-(2-hydroxy-2-propanyl)-5-(4-phenoxyphenyl)pyrrolo[2,1-f][1,2,4]triazin-6-yl]acrylic acid,
(96) 3-(4-amino-7-cyclopentyl-5-{3-methoxy-4-[3-(2-propanyl)phenoxy]phenyl}pyrrolo[2,1-f][1,2,4]triazin-6-yl)propanoic acid,
(97) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid,
(98) (2E)-3-{4-amino-7-[1-(methylsulfonyl)-4-piperidinyl]-5-(4-phenoxyphenyl)pyrrolo[2,1-f][1,2,4]triazin-6-yl}acrylic acid,
(99) (2E)-3-[4-amino-7-cyclopentyl-5-(2-fluoro-4-phenoxyphenyl)pyrrolo[2,1-f][1,2,4]triazin-6-yl]acrylic acid,
(100) 3-[4-amino-7-(3-methoxyphenyl)-5-(4-phenoxyphenyl)pyrrolo[2,1-f][1,2,4]triazin-6-yl]propanoic acid,
(101) (2E)-3-[4-amino-7-cyclohexyl-5-(4-phenoxyphenyl)pyrrolo[2,1-f][1,2,4]triazin-6-yl]acrylic acid,
(102) (2E)-3-[4-amino-7-(1,1-dioxidotetrahydro-2H-thiopyran-4-yl)-5-(4-phenoxyphenyl)pyrrolo[2,1-f][1,2,4]triazin-6-yl]acrylic acid,
(103) (2E)-3-(4-amino-7-cyclopentyl-5-{-4-[3-(2-propanyl)phenoxy]phenyl}pyrrolo[2,1-f][1,2,4]triazin-6-yl)acrylic acid,
(104) (2E)-3-[4-amino-5-{4-(3-chlorophenoxy)-3-methoxyphenyl}-7-cyclopentylpyrrolo[2,1-f][1,2,4]triazin-6-yl]acrylic acid,
(105) (2E)-3-[4-amino-5-(4-phenoxyphenyl)-7-(tetrahydro-2H-pyran-4-yl)pyrrolo[2,1-f][1,2,4]triazin-6-yl]acrylic acid,
(106) (2E)-3-[4-amino-7-(3-hydroxy-3-methylbutyl)-5-(4-phenoxyphenyl)pyrrolo[2,1-f][1,2,4]triazin-6-yl]acrylic acid,
(107) (2E)-3-[4-amino-7-isopropyl-5-(4-phenoxyphenyl)pyrrolo[2,1-f][1,2,4]triazin-6-yl]acrylic acid,
(108) N-{2-[4-amino-7-cyclopentyl-5-(4-phenoxyphenyl)pyrrolo[2,1-f][1,2,4]triazin-6-yl]ethyl}acetamide,
(109) 1-[4-amino-7-cyclopentyl-5-(4-phenoxyphenyl)pyrrolo[2,1-f][1,2,4]triazin-6-yl]-1,2-ethanediol,
(110) 4-[4-amino-7-cyclopentyl-5-(4-phenoxyphenyl)pyrrolo[2,1-f][1,2,4]triazin-6-yl]-1-hydroxy-2-butanone,
(111) 4-amino-7-cyclopentyl-N-(2-hydroxyethyl)-5-(4-phenoxyphenyl)pyrrolo[2,1-f][1,2,4]triazine-6-carboxamide,
(112) 4-amino-7-cyclopentyl-5-(4-phenoxyphenyl)-N-(1H-pyrazol-4-yl)pyrrolo[2,1-f][1,2,4]triazine-6-carboxamide,
(113) 4-amino-7-cyclopentyl-5-(4-phenoxyphenyl)-N-(1H-pyrazol-3-yl)pyrrolo[2,1-f][1,2,4]triazine-6-carboxamide,
(114) (2E)-3-[4-amino-7-cyclopentyl-5-(4-phenoxyphenyl)pyrrolo[2,1-f][1,2,4]triazin-6-yl]acrylamide,
(115) 4-amino-7-cyclopentyl-N-(2-methoxyethyl)-5-(4-phenoxyphenyl)pyrrolo[2,1-f][1,2,4]triazine-6-carboxamide,
(116) 4-amino-7-cyclopentyl-5-(4-phenoxyphenyl)pyrrolo[2,1-f][1,2,4]triazine-6-carbohydrazide,
(117) 4-amino-7-cyclopentyl-N-[2-(dimethylamino)ethyl]-5-(4-phenoxyphenyl)pyrrolo[2,1-f][1,2,4]triazine-6-carboxamide,
(118) (2E)-3-[4-amino-7-cyclopentyl-5-(4-phenoxyphenyl)pyrrolo[2,1-f][1,2,4]triazin-6-yl]-N-(1H-pyrazol-4-yl)acrylamide, or
(119) 4-amino-7-cyclopentyl-5-(4-phenoxyphenyl)pyrrolo[2,1-f][1,2,4]triazine-6-carboxamide.

In particular, the compounds described in Examples shown below are preferable. It recites (1) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 6-(3-(dimethylamino)propyl)-7-(3-methoxyphenyl)-5-(4-phenoxyphenyl)pyrrolo[2,1-f][1,2,4]triazin-4-amine,
(3) 7-(3-methoxyphenyl)-5-(4-phenoxyphenyl)-6-(3-(pyrrolidin-1-yl)propyl)pyrrolo[2,1-f][1,2,4]triazin-4-amine,
(4) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(5) 5-[4-(3-chlorophenoxy)phenyl]-7-(3-methoxyphenyl)-6-(4-morpholinylmethyl)pyrrolo[2,1-f][1,2,4]triazin-4-amine,
(6) 5-[4-(3-chlorophenoxy)phenyl]-7-cyclopentyl-6-(4-morpholinylmethyl)pyrrolo[2,1-f][1,2,4]triazin-4-amine,
(7) 1-(4-(4-amino-5-(4-(3,4-dichlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(8) 1-(4-(4-amino-5-(4-(3-chlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(9) 7-cyclopentyl-5-(4-(3,4-dichlorophenoxy)-3-methoxyphenyl)-6-(2-(pyridin-3-yl)ethyl)pyrrolo[2,1-f][1,2,4]triazin-4-amine,
(10) 7-(3-methoxyphenyl)-5-(4-phenoxyphenyl)-6-[2-(3-pyridinyl)ethyl]pyrrolo[2,1-f][1,2,4]triazin-4-amine,
(11) 5-[4-(3,4-dichlorophenoxy)phenyl]-7-(3-methoxyphenyl)-6-[2-(3-pyridinyl)ethyl]pyrrolo[2,1-f][1,2,4]triazin-4-amine,
(12) 7-(3-methoxyphenyl)-5-(4-phenoxyphenyl)-6-(piperidin-4-yl)pyrrolo[2,1-f][1,2,4]triazin-4-amine,
(13) 7-cyclopentyl-5-(4-(3,4-dichlorophenoxy)-3-methoxyphenyl)-6-(piperidin-4-yl)pyrrolo[2,1-f][1,2,4]triazin-4-amine,
(14) 5-(4-(3-chlorophenoxy)-3-methoxyphenyl)-7-cyclopentyl-6-(piperidin-4-yl)pyrrolo[2,1-f][1,2,4]triazin-4-amine,
(15) 3-(4-(4-amino-7-cyclopentyl-6-(piperidin-4-yl)pyrrolo[2,1-f][1,2,4]triazin-5-yl)-2-methoxyphenoxy)benzonitrile,
(16) 5-[4-(3,4-dichlorophenoxy)-3-methoxy-phenyl]-7-(1-methylsulfonyl-4-piperidyl)-6-(4-piperidyl)pyrrolo[2,1-f][1,2,4]triazin-4-amine,
(17) 5-(4-(3-chlorophenoxy)-3-methoxyphenyl)-7-(1-(methylsulfonyl)piperidin-4-yl)-6-(piperidin-4-yl)pyrrolo[2,1-f][1,2,4]triazin-4-amine,
(18) (3-{amino-5-[4-(3-chlorophenoxy)-3-methoxyphenyl]-6-(4-pyridinyl)pyrrolo[2,1-f][1,2,4]triazin-7-yl}phenyl)(4-methyl-1-piperazinyl)methanone,
(19) 7-cycloheptyl-5-[4-(3,4-dichlorophenoxy)-3-methoxyphenyl]-6-(4-piperidinyl)pyrrolo[2,1-f][1,2,4]triazin-4-amine,
(20) 5-[4-(3-chlorophenoxy)-3-methoxyphenyl]-7-cycloheptyl-6-(4-piperidinyl)pyrrolo[2,1-f][1,2,4]triazin-4-amine,

(21) 5-[4-(3,4-dichlorophenoxy)-3-methoxyphenyl]-7-(3-methoxyphenyl)-6-(4-piperidinyl)pyrrolo[2,1-f][1,2,4]triazin-4-amine,
(22) 5-[4-(3-chlorophenoxy)-3-methoxyphenyl]-7-(3-methoxyphenyl)-6-(4-piperidinyl)pyrrolo[2,1-f][1,2,4]triazin-4-amine,
(23) N-(4-{4-amino-5-[4-(3-chlorophenoxy)-3-methoxyphenyl]-6-(4-piperidinyl)pyrrolo[2,1-f][1,2,4]triazin-7-yl}phenyl)-N-methylmethanesulfonamide,
(24) 5-[4-(3-chlorophenoxy)-3-methoxyphenyl]-7-(4-methoxyphenyl)-6-(4-piperidinyl)pyrrolo[2,1-f][1,2,4]triazin-4-amine,
(25) N-(4-{4-amino-5-[4-(3,4-dichlorophenoxy)-3-methoxyphenyl]-6-(4-piperidinyl)pyrrolo[2,1-f][1,2,4]triazin-7-yl}phenyl)-N-methylmethanesulfonamide,
(26) 3-{-4-[4-amino-7-(4-methoxyphenyl)-6-(4-piperidinyl)pyrrolo[2,1-f][1,2,4]triazin-5-yl]-2-methoxyphenoxy}benzonitrile,
(27) 6-chloro-5-(4-(3-chlorophenoxy)-3-methoxyphenyl)-7-(1-(methylsulfonyl)piperidin-4-yl)pyrrolo[2,1-f][1,2,4]triazin-4-amine,
(28) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(29) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(30) 5-(4-(3-chlorophenoxy)-3-methoxyphenyl)-7-cyclopentyl-6-(pyrrolidin-3-yl)pyrrolo[2,1-f][1,2,4]triazin-4-amine,
(31) 5-[4-(3-chlorophenoxy)phenyl]-7-cyclopentyl-6-(2-ethoxyethyl)pyrrolo[2,1-f][1,2,4]triazin-4-amine,
(32) 3-{4-amino-5-[4-(3,4-dichlorophenoxy)-3-methoxyphenyl]-7-(3-methoxyphenyl)pyrrolo[2,1-f][1,2,4]triazin-6-yl}propanoic acid,
(33) {4-amino-7-cyclopentyl-5-[4-(3,4-dichlorophenoxy)-3-methoxyphenyl]pyrrolo[2,1-f][1,2,4]triazin-6-yl}acetic acid,
(34) 2-{4-amino-7-cyclopentyl-5-[4-(3,4-dichlorophenoxy)-3-methoxyphenyl]pyrrolo[2,1-f][1,2,4]triazin-6-yl}ethanol,
(35) methyl 4-amino-7-(3-methoxyphenyl)-5-(4-phenoxyphenyl)pyrrolo[2,1-f][1,2,4]triazine-6-carboxylate,
(36) 4-amino-7-(3-methoxyphenyl)-5-(4-phenoxyphenyl)pyrrolo[2,1-f][1,2,4]triazine-6-carboxylic acid,
(37) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(38) 4-amino-7-cyclopentyl-5-(4-phenoxyphenyl)pyrrolo[2,1-f][1,2,4]triazine-6-carboxylic acid,
(39) 3-{4-amino-5-[4-(3-chlorophenoxy)-3-methoxyphenyl]-7-(1-propen-2-yl)pyrrolo[2,1-f][1,2,4]triazin-6-yl}propanoic acid,
(40) (2E)-3-[4-amino-7-cyclopentyl-5-(4-phenoxyphenyl)pyrrolo[2,1-f][1,2,4]triazin-6-yl]acrylonitrile,
(41) methyl ({[4-amino-7-cyclopentyl-5-(4-phenoxyphenyl)pyrrolo[2,1-f][1,2,4]triazin-6-yl]carbonyl}amino)acetate,
(42) 6-fluoro-7-(3-methoxyphenyl)-5-(4-phenoxyphenyl)pyrrolo[2,1-f][1,2,4]triazin-4-amine,
(43) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(44) 3-[4-amino-7-cyclopentyl-5-(4-phenoxyphenyl)pyrrolo[2,1-f][1,2,4]triazin-6-yl]-2-methylacrylic acid,
(45) (2E)-3-{4-amino-7-cyclopentyl-5-[4-(3,4-dichlorophenoxy)-3-methoxyphenyl]pyrrolo[2,1-f][1,2,4]triazin-6-yl}acrylic acid,
(46) (2E)-3-[4-amino-7-cyclopentyl-5-(4-phenoxyphenyl)pyrrolo[2,1-f][1,2,4]triazin-6-yl]acrylamide,
(47) (2E)-3-[4-amino-7-cyclopentyl-5-(4-phenoxyphenyl)pyrrolo[2,1-f][1,2,4]triazin-6-yl]-2-propen-1-ol,
(48) 6-(2-aminoethyl)-7-cyclopentyl-5-(4-phenoxyphenyl)pyrrolo[2,1-f][1,2,4]triazin-4-amine,
(49) (2E)-3-[4-amino-7-cyclopentyl-5-(4-phenoxyphenyl)pyrrolo[2,1-f][1,2,4]triazin-6-yl]acrylohydrazide,
(50) 3-{4-amino-5-[4-(3,4-dichlorophenoxy)-3-methoxyphenyl]-7-(3-methoxyphenyl)pyrrolo[2,1-f][1,2,4]triazin-6-yl}propanamide,
(51) (2E)-1-(3-{4-amino-6-chloro-5-[4-(3,4-dichlorophenoxy)-3-methoxyphenyl]pyrrolo[2,1-f][1,2,4]triazin-7-yl}-1-piperidinyl)-4-(dimethylamino)-2-buten-1-one,
(52) 1-(3-{4-amino-6-chloro-5-[4-(3-chlorophenoxy)-3-methoxyphenyl]pyrrolo[2,1-f][1,2,4]triazin-7-yl}-1-pyrrolidinyl)-2-propen-1-one,
(53) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(54) 3-{4-amino-5-[4-(3-chlorophenoxy)-3-methoxyphenyl]-7-cyclopentylpyrrolo[2,1-f][1,2,4]triazin-6-yl}propanoic acid,
(55) 4-{4-amino-5-[4-(3-chlorophenoxy)-3-methoxyphenyl]-7-(3-methoxyphenyl)pyrrolo[2,1-f][1,2,4]triazin-6-yl}butanoic acid,
(56) 4-{4-amino-5-[4-(3,4-dichlorophenoxy)-3-methoxyphenyl]-7-(3-methoxyphenyl)pyrrolo[2,1-f][1,2,4]triazin-6-yl}butanoic acid,
(57) 3-(4-amino-5-[4-(3-chlorophenoxy)-3-methoxyphenyl]-7-{4-[(methylsulfonyl)amino]phenyl}pyrrolo[2,1-f][1,2,4]triazin-6-yl)propanoic acid,
(58) (2E)-3-[4-amino-7-(3-methoxyphenyl)-5-(4-phenoxyphenyl)pyrrolo[2,1-f][1,2,4]triazin-6-yl]acrylic acid,
(59) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(60) 5-[4-(3,4-dichlorophenoxy)-3-methoxyphenyl]-7-(3-methoxyphenyl)-6-[2-(1H-tetrazol-5-yl)ethyl]pyrrolo[2,1-f][1,2,4]triazin-4-amine,
(61) 3-{4-amino-5-[4-(3-chlorophenoxy)phenyl]-7-cyclopentylpyrrolo[2,1-f][1,2,4]triazin-6-yl}propanoic acid,
(62) 3-{4-amino-7-cyclopentyl-5-[4-(3,4-dichlorophenoxy)phenyl]pyrrolo[2,1-f][1,2,4]triazin-6-yl}propanoic acid,
(63) 3-{4-amino-7-cyclopentyl-5-[4-(3,4-dichlorophenoxy)-3-methoxyphenyl]pyrrolo[2,1-f][1,2,4]triazin-6-yl}propanoic acid,
(64) 3-(4-amino-7-cyclopentyl-5-{4-{3-(2-propanyl)phenoxy}phenyl}pyrrolo[2,1-f][1,2,4]triazin-6-yl) propanoic acid,
(65) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,
(66) 3-[4-amino-7-cyclopentyl-5-(4-phenoxyphenyl)pyrrolo[2,1-f][1,2,4]triazin-6-yl]propanoic acid,
(67) 3-[4-amino-7-cyclopentyl-5-(3-hydroxyphenyl)pyrrolo[2,1-f][1,2,4]triazin-6-yl]propanoic acid,
(68) 1-(3-{4-amino-6-chloro-5-[4-(3-chlorophenoxy)-3-hydroxyphenyl]pyrrolo[2,1-f][1,2,4]triazin-7-yl}-1-piperidinyl)-2-propen-1-one,
(69) 3-{4-amino-5-[4-(3-chlorophenoxy)-3-methoxyphenyl]-7-(3-methoxyphenyl)pyrrolo[2,1-f][1,2,4]triazin-6-yl}propanoic acid,
(70) 3-{4-amino-5-[4-(3-chlorophenoxy)-3-methoxyphenyl]-7-(4-methoxyphenyl)pyrrolo[2,1-f][1,2,4]triazin-6-yl}propanoic acid,

(71) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(72) 3-{4-amino-5-[4-(3-chlorophenoxy)-3-methoxyphenyl]-7-phenylpyrrolo[2,1-f][1,2,4]triazin-6-yl}propanoic acid,
(73) 3-{4-amino-5-[4-(3-chlorophenoxy)-3-methoxyphenyl]-7-(2-fluorophenyl)pyrrolo[2,1-f][1,2,4]triazin-6-yl}propanoic acid,
(74) 3-{4-amino-5-[4-(3-chlorophenoxy)-3-methoxyphenyl]-7-(3-fluorophenyl)pyrrolo[2,1-f][1,2,4]triazin-6-yl}propanoic acid,
(75) 3-{4-amino-5-[4-(3-chlorophenoxy)-3-methoxyphenyl]-7-(4-fluorophenyl)pyrrolo[2,1-f][1,2,4]triazin-6-yl}propanoic acid,
(76) 3-{4-amino-7-cyclopentyl-5-[4-(3,5-difluorophenoxy)-3-methoxyphenyl]pyrrolo[2,1-f][1,2,4]triazin-6-yl}propanoic acid,
(77) 3-{4-amino-7-cyclopentyl-5-[4-(3,5-dichlorophenoxy)-3-methoxyphenyl]pyrrolo[2,1-f][1,2,4]triazin-6-yl}propanoic acid,
(78) 3-{4-amino-7-(3-carbamoylphenyl)-5-[4-(3-chlorophenoxy)-3-methoxyphenyl]pyrrolo[2,1-f][1,2,4]triazin-6-yl}propanoic acid,
(79) 3-{4-amino-7-cyclopentyl-5-[4-(3,5-difluorophenoxy)phenyl]pyrrolo[2,1-f][1,2,4]triazin-6-yl}propanoic acid,
(80) 3-{4-amino-7-cyclopentyl-5-[4-(3,5-dichlorophenoxy)phenyl]pyrrolo[2,1-f][1,2,4]triazin-6-yl}propanoic acid,
(81) (2E)-3-[4-amino-7-cyclopentyl-5-(4-phenoxyphenyl)pyrrolo[2,1-f][1,2,4]triazin-6-yl]acrylic acid,
(82) 3-{4-amino-5-[4-(3-chlorophenoxy)-3-methoxyphenyl]-7-(2-hydroxy-2-propanyl)pyrrolo[2,1-f][1,2,4]triazin-6-yl}propanoic acid,
(83) ({[4-amino-7-cyclopentyl-5-(4-phenoxyphenyl)pyrrolo[2,1-f][1,2,4]triazin-6-yl]carbonyl}amino)acetic acid,
(84) 3-(4-amino-5-[4-(3-chlorophenoxy)-3-methoxyphenyl]-7-{4-[methyl(methylsulfonyl)amino]phenyl}pyrrolo[2,1-f][1,2,4]triazin-6-yl)propanoic acid,
(85) 3-{4-amino-5-[4-(3-chlorophenoxy)-3-methoxyphenyl]-7-[4-(methylsulfonyl)phenyl]pyrrolo[2,1-f][1,2,4]triazin-6-yl}propanoic acid,
(86) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one,
(87) 3-[4-amino-7-{-4-[methyl(methylsulfonyl)amino]phenyl}-5-(4-phenoxyphenyl)pyrrolo[2,1-f][1,2,4]triazin-6-yl]propanoic acid,
(88) (2E)-3-[4-amino-7-(2-hydroxy-2-propanyl)-5-(4-phenoxyphenyl)pyrrolo[2,1-f][1,2,4]triazin-6-yl]acrylic acid,
(89) 3-(4-amino-7-cyclopentyl-5-{3-methoxy-4-[3-(2-propanyl)phenoxy]phenyl}pyrrolo[2,1-f][1,2,4]triazin-6-yl)propanoic acid,
(90) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid,
(91) (2E)-3-{4-amino-7-[1-(methylsulfonyl)-4-piperidinyl]-5-(4-phenoxyphenyl)pyrrolo[2,1-f][1,2,4]triazin-6-yl}acrylic acid,
(92) (2E)-3-[4-amino-7-cyclopentyl-5-(2-fluoro-4-phenoxyphenyl)pyrrolo[2,1-f][1,2,4]triazin-6-yl]acrylic acid,
(93) 3-[4-amino-7-(3-methoxyphenyl)-5-(4-phenoxyphenyl)pyrrolo[2,1-f][1,2,4]triazin-6-yl]propanoic acid,
(94) (2E)-3-[4-amino-7-cyclohexyl-5-(4-phenoxyphenyl)pyrrolo[2,1-f][1,2,4]triazin-6-yl]acrylic acid,
(95) (2E)-3-[4-amino-7-(1,1-dioxidotetrahydro-2H-thiopyran-4-yl)-5-(4-phenoxyphenyl)pyrrolo[2,1-f][1,2,4]triazin-6-yl]acrylic acid,
(96) (2E)-3-(4-amino-7-cyclopentyl-5-{4-[3-(2-propanyl)phenoxy]phenyl}pyrrolo[2,1-f][1,2,4]triazin-6-yl)acrylic acid,
(97) (2E)-3-{4-amino-5-[4-(3-chlorophenoxy)-3-methoxyphenyl]-7-cyclopentylpyrrolo[2,1-f][1,2,4]triazin-6-yl}acrylic acid,
(98) (2E)-3-[4-amino-5-(4-phenoxyphenyl)-7-(tetrahydro-2H-pyran-4-yl)pyrrolo[2,1-f][1,2,4]triazin-6-yl]acrylic acid,
(99) (2E)-3-[4-amino-7-(3-hydroxy-3-methylbutyl)-5-(4-phenoxyphenyl)pyrrolo[2,1-f][1,2,4]triazin-6-yl]acrylic acid,
(100) (2E)-3-[4-amino-7-isopropyl-5-(4-phenoxyphenyl)pyrrolo[2,1-f][1,2,4]triazin-6-yl]acrylic acid,
(101) N-{2-[4-amino-7-cyclopentyl-5-(4-phenoxyphenyl)pyrrolo[2,1-f][1,2,4]triazin-6-yl]ethyl}acetamide,
(102) 1-[4-amino-7-cyclopentyl-5-(4-phenoxyphenyl)pyrrolo[2,1-f][1,2,4]triazin-6-yl]-1,2-ethanediol,
(103) 4-[4-amino-7-cyclopentyl-5-(4-phenoxyphenyl)pyrrolo[2,1-f][1,2,4]triazin-6-yl]-1-hydroxy-2-butanone,
(104) 4-amino-7-cyclopentyl-N-(2-hydroxyethyl)-5-(4-phenoxyphenyl)pyrrolo[2,1-f][1,2,4]triazine-6-carboxamide,
(105) 4-amino-7-cyclopentyl-5-(4-phenoxyphenyl)-N-(1H-pyrazol-4-yl)pyrrolo[2,1-f][1,2,4]triazine-6-carboxamide,
(106) 4-amino-7-cyclopentyl-5-(4-phenoxyphenyl)-N-(1H-pyrazol-3-yl)pyrrolo[2,1-f][1,2,4]triazine-6-carboxamide,
(107) (2E)-3-[4-amino-7-cyclopentyl-5-(4-phenoxyphenyl)pyrrolo[2,1-f][1,2,4]triazin-6-yl]acrylamide,
(108) 4-amino-7-cyclopentyl-N-(2-methoxyethyl)-5-(4-phenoxyphenyl)pyrrolo[2,1-f][1,2,4]triazine-6-carboxamide,
(109) 4-amino-7-cyclopentyl-5-(4-phenoxyphenyl)pyrrolo[2,1-f][1,2,4]triazine-6-carbohydrazide,
(110) 4-amino-7-cyclopentyl-N-[2-(dimethylamino)ethyl]-5-(4-phenoxyphenyl)pyrrolo[2,1-f][1,2,4]triazine-6-carboxamide,
(111) (2E)-3-[4-amino-7-cyclopentyl-5-(4-phenoxyphenyl)pyrrolo[2,1-f][1,2,4]triazin-6-yl]-N-(1H-pyrazol-4-yl)acrylamide, or
(112) 4-amino-7-cyclopentyl-5-(4-phenoxyphenyl)pyrrolo[2,1-f][1,2,4]triazine-6-carboxamide.

More preferably, it recites (1) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(3) 7-cycloheptyl-5-(4-(3,4-dichlorophenoxy)-3-methoxyphenyl)-6-(piperidin-4-yl)pyrrolo[2,1-f][1,2,4]triazin-4-amine,
(4) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(5) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(6) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(7) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(8) 1-(3-{4-amino-6-chloro-5-[4-(3-chlorophenoxy)-3-methoxyphenyl]pyrrolo[2,1-f][1,2,4]triazin-7-yl}-1-pyrrolidinyl)-2-propen-1-one, (9) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(10) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(11) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,
(12) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(13) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one, or
(14) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid.

The prodrug for the compound of the formula (I) means a compound which is converted to the compound represented by the formula (I) by the reaction with an enzyme, a gastric acid, or the like, in the living body. Examples of the prodrug for the compound represented by the formula (I) include a compound wherein the amino group of the compound represented by the formula (I) is acylated, alkylated, phosphorylated, or the like (such as a compound wherein the amino group of the compound represented by the formula (I) is substituted with eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, acetoxymethylation, tert-butylation, and the like); a compound wherein the hydroxy group of the compound represented by the formula (I) is acylated, alkylated, phosphorylated, borated, or the like (such as a compound wherein the hydroxy group of the compound represented by the formula (I) is modified by acetylation, palmitoylation, propanoylation, pivaloylation, succinylation, fumaration, alanylation, dimethylaminomethylcarbonylation, and the like); a compound wherein the carboxyl of the compound represented by the formula (I) is modified by esterification, amidation, or the like (such as a compound wherein the carboxyl of the compound represented by the formula (I) is esterified or amidated with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, and the like), and the like. These compounds may be prepared by a known method. In addition, the prodrug for the compound represented by the formula (I) may take a hydrate form or a non-hydrate form. In addition, the prodrug for the compound represented by the formula (I) may be a compound which is converted into the compound represented by the formula (I) under the physiological conditions as described in Pharmaceutical Research and Development, Vol. 7 "Molecular Design", pages 163-198 published in 1990 by Hirokawa Publishing Co. In addition, the compound represented by formula (I) may be labeled with an isotope (such as $^{2}H$, $^{3}H$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like.) and the like.

Unless otherwise specified, the compound of the present invention includes all isomers thereof. For example, alkyl, alkenyl, alkynyl, alkoxy, alkylthio, alkylene, alkenylene and alkynylene group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention. Further, isomers due to the tautomerism are all included in the present invention.

[Salt]

In the present invention, the compound represented by the formula (I) may form a salt thereof, and may be N-oxide form thereof or quaternary ammonium salt thereof. Furthermore, these compounds may be a solvate thereof. The compounds of the present invention include all pharmacologically acceptable salts thereof. As pharmacologically acceptable salts, water-soluble salts with very low toxicity are preferred. Suitable pharmacologically acceptable salts of the compound of the present invention include, for example, salts of alkali metals (such as potassium, sodium, lithium, and the like); salts of alkaline earth metals (such as calcium, magnesium, and the like); ammonium salts (such as tetramethylammonium salts, tetrabutylammonium salts, and the like); salts of organic amines (such as triethylamine, methylamine, dimethylamine, cyclopentylamine, benzylamine, phenethylamine, piperidine, monoethanolamine, diethanolamine, tris (hydroxymethyl)methylamine, lysine, arginine, N-methyl-D-glucamine, and the like); and acid addition salts such as salts of inorganic acid (such as hydrochloride, hydrobromide, hydroiodide, sulfate, phosphate, nitrate, and the like), and salts of organic acid (such as acetate, trifluoroacetate, lactate, tartrate, oxalate, fumarate, maleate, benzoate, citrate, methansulfonate, ethansulfonate, benzenesulfonate, toluenesulfonate, isethionate, gulcuronate, gluconate, and the like), and the like. The N-oxide form of the compound represented by the formula (I) means the compound of which the nitrogen atom was oxidized. The quaternary ammonium salt of the compound represented by the formula (I) means the compound wherein the nitrogen atom is quaternized by $R^0$ ($R^0$ represents alkyl, alkenyl, or alkynyl (herein, which has the same meaning as described above) which each are optionally substituted, and cyclic ring (which has the same meaning as described above) which may have a substituent(s).) The quaternary ammonium salt of the compound represented by the formula (I) may additionally form the salt described above and the N-oxide form described above. The appropriate solvate of the compound represented by the formula (I), a salt thereof, an N-oxide form thereof, and a quaternary ammonium salt thereof, include water, alcohol solvate (such as ethanol) and the like. The solvates are preferably nontoxic and water-soluble. The compounds represented by the formula (I) can be converted into the salt described above, the N-oxide form described above thereof, or the solvates described above by conventional means.

[Process for Preparing the Compounds of the Present Invention]

The compounds of the present invention as represented by the formula (I) can be produced, for example, in accordance with the below described processes or processes similar thereto, or the processes described in examples. In the below described production processes, the starting compounds may be used as salts, wherein as such salts, there may be used the pharmaceutically acceptable salts of the compounds represented by the formula (I) to be described below.

In the Scheme A to Scheme E described below, "Sonogashira reaction" may be abbreviated as "Sonogashira", "Suzuki coupling reaction" may be abbreviated as "Suzuki" and "Stille coupling reaction" may be abbreviated as "Stille".

In the compounds represented by the formula (I), for example, the compounds wherein $R^2$ represents $R^{2A}$ and $R^4$ represents C2-4alkyl substituted with $R^{4A}$, i.e., the compound represented by formula (I-A);

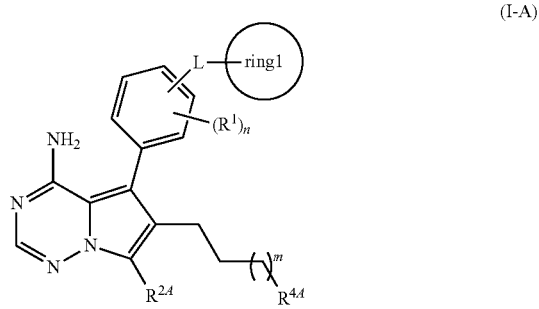

(I-A)

wherein ring0, $R^1$, L and n have the same meanings as the above described, $R^{2A}$ represents ring2 optionally substituted with —K—$R^3$, $R^{4A}$ it represents ring4, $NR^{4-101}R^{4-102}$, $CO_2R^{4-103}$ or $OR^{4-103}$, m is 0 or an integer of 1-2, can be produced by as shown below in Scheme A.

The compounds of the formula A-2 may be synthesized by a Sonogashira reaction with the compound corresponding to Example 5 and the compounds of formula A-1. This reaction is a known method, and can be carried out, for example, in an organic solvent (such as toluene, benzene, N,N-dimethylformamide (DMF), N-methylpyrrolidone (NMP), N,N-dimethylacetamide (DMA), tetrahydrofuran, acetonitrile, dimethoxyethane, and the like) and under the presence of a base (such as sodium hydroxide, potassium hydroxide, diisopropylamine, triethylamine, sodium carbonate, sodium hydrogen carbonate, potassium carbonate, and the like) in the presence of a palladium catalyst (such as tetrakis(triphenylphosphine)palladium ($Pd(PPh_3)_4$), dichlorobis(triphenylphosphine)palladium ($Cl_2Pd(PPh_3)_2$) and the like) or a copper catalyst (such as copper iodide and the like) at the temperature of 0° C. to reflux temperature.

The compounds of the present invention may be synthesized by known coupling methods instead of Songashira reaction described in Scheme A. For example, the intended compounds instead of compounds of formula A-2 may be synthesized by reactions with the compound corresponding to Example 5 and any of following compounds selected from the organozinc compounds, alkene compounds and alcohol compounds with carbon monoxide instead of the compound of formula A-1. These reactions can be carried out, for example, in an organic solvent (such as tetrahydrofuran, toluene, acetonitrile, benzene, N,N-dimethylformamide (DMF), N-methylpyrrolidone (NMP), N,N-dimethylacetamide (DMA), tetrahydrofuran, dimethoxyethane and the like) under the presence or absence of a base (such as N,N-diisopropylethylamine, sodium hydroxide, potassium hydroxide, diisopropylamine, triethylamine, sodium carbonate, sodium hydrogen carbonate, potassium carbonate, and the like) in the presence of a palladium catalyst (such as tetrakis(triphenylphosphine)palladium ($Pd(PPh_3)_4$), dichlorobis(triphenylphosphine)palladium ($Cl_2Pd(PPh_3)_2$) and the like) or nickel catalyst (such as [1,3-Bis(diphenylphosphino)propane]nickel(II) dichloride ($Ni(dppp)Cl_2$) and the like) at the temperature of 0° C. to reflux temperature.

The compounds of formula A-3 may be synthesized by a reduction reaction of the compounds of formula A-2. This reduction reaction is a known method, and can be carried out, for example, in an organic solvent (such as methanol, ethanol, tetrahydrofuran, and the like) using a catalyst (such as palladium carbon, platinum (IV) oxide and the like), under an atmosphere of hydrogen at atmospheric pressure or applied pressure at the temperature of –78° C. to reflux temperature.

The compounds of formula A-4 may be synthesized by a bromination of the compounds of formula A-3. This reaction is a known method, and can be carried out, for example, in an organic solvent (such as DMF, dichloromethane, tetrahydrofuran, toluene, acetic acid, and the like) with a brominating agent (such as 1,3-dibromo-5,5-dimethylimidazolidine-2,4-dione, bromine, N-bromosuccinimide (NBS), and the like) at the temperature of –78° C. to reflux temperature.

The compounds of formula A-7 may be synthesized by a Suzuki coupling reaction with the compounds of formula A-5 or A-6 and the compounds of formula A-4. This reaction is a known method, and can be carried out, for example, in an organic solvent (such as toluene, benzene, N,N-dimethylformamide (DMF), tetrahydrofuran, methanol, ethanol, acetonitrile, dimethoxyethane, acetone, dioxane, dimethylacetamide, and the like) and water and under the presence of a base (such as sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide, tetrabutylammonium fluoride, and the like) in the presence of palladium catalyst (such as tetrakis (triphenylphosphine)palladium ($Pd(PPh_3)_4$), dichlorobis (triphenylphosphine)palladium ($Cl_2Pd(PPh_3)_2$), palladium acetate ($Pd(OAc)_2$), and the like) at the temperature of room temperature to 120° C.

Herein, the compound of formula A-7 may be reduced by the above described reduction reaction, if necessary.

The compounds of formula A-8 may be synthesized by a bromination of the compounds of formula A-7.

The compounds of formula (I-A) may be synthesized by a Suzuki coupling reaction with compounds of formula A-9 or A-10 and compounds of formula A-8.

If the variable groups of the compounds described in the below scheme contain protective groups, the deprotection reaction for the protective group can be performed as necessary. The deprotection reactions for the protective groups of carboxyl, hydroxyl, amino or thiol group are well known, and are exemplified by:

(1) Alkali hydrolysis,
(2) Deprotection reaction under acidic conditions,
(3) Deprotection reaction through hydrogenolysis,
(4) Deprotection reaction for a silyl group,
(5) Deprotection reaction with a metal, and
(6) Deprotection reaction with a metal complex.

Each reaction above is described below in detail.

The deprotection reaction through alkali hydrolysis is carried out, for example, in an organic solvent (such as methanol, tetrahydrofuran, dioxane, and the like) with use of a hydroxide of an alkali metal (sodium hydroxide, potassium hydroxide, lithium hydroxide, and the like), a hydroxide of an alkaline earth metal (barium hydroxide, calcium hydroxide, and the like) or a carbonate (sodium carbonate, potassium carbonate, and the like), an aqueous solution thereof, or their mixtures at a temperature of about 0 to 40° C.

The deprotection reaction under acidic conditions is carried out, for example, in an organic solvent (such as dichloromethane, chloroform, dioxane, ethyl acetate, anisole, and the like) and in an organic acid (such as acetic acid, trifluoroacetic acid, methanesulfonic acid, p-tosyl acid, and the like), inorganic acid (such as hydrochloric acid, sulfuric acid, and the like) or their mixtures (hydrobromic acid/acetic acid, and the like) in the presence or absence of 2,2,2-trifluoroethanol at a temperature of about 0 to 100° C.

The deprotection reaction through hydrogenolysis is carried out, for example, in a solvent (such as ether-based ones (such as tetrahydrofuran, dioxane, dimethoxyethane, diethyl ether, and the like), alcohol-based ones (such as methanol, ethanol, and the like), benzene-based ones (such as benzene, toluene and the like), ketone-based ones (acetone, methyl ethyl ketone, and the like), nitrile-based ones (such as acetonitrile and the like), amide-based ones (such as dimethylformamide and the like), water, ethyl acetate, acetic acid or solvent mixtures of not less than two thereof, and the like) in the presence of a catalyst (such as palladium-carbon, palladium black, palladium hydroxide-carbon, platinum oxide, Raney-nickel, and the like), under an atmosphere of hydrogen at atmospheric pressure or applied pressure, or in the presence of ammonium formate at a temperature of about 0 to 200° C.

The deprotection reaction for a silyl group is conducted into practice, for example, in a water-miscible organic solvent (such as tetrahydrofuran, acetonitrile, and the like) with use of tetrabutylammonium fluoride at a temperature of about 0 to 40° C.

The deprotection reaction with use of a metal is performed, for example, in an acidic solvent (such as acetic acid, a buffer of pH about 4.2 to 7.2 or mixed solutions thereof with organic solvents, such as tetrahydrofuran, and the like) in the presence of powdered zinc at a temperature of about 0 to 40° C., under application of ultrasonics, if necessary.

The deprotection reaction with use of a metal complex is carried out, for example, in an organic solvent (such as dichloromethane, dimethylformamide, tetrahydrofuran, ethyl acetate, acetonitrile, dioxane, ethanol, and the like), water or solvent mixtures thereof in the presence of a trap reagent (such as tribuityltin hydride, triethylsilane, dimedone, morpholine, diethylamine, pyrrolidine, and the like), organic acid (such as acetic acid, formic acid, 2-ethylhexanoic acid, and the like) and/or organic acid salt (such as sodium 2-ethylhexanoate, potassium 2-ethylhexanoate, and the like), in the presence or absence of a phosphine-based reagent (such as triphenylphosphine, and the like), at a temperature of about 0 to 40° C., while using a metal complex (such as tetrakis-triphenylphosphine palladium (0), palladium (II) bis(triphenylphosphine) dichloride, palladium (II) acetate, rhodium (I) tris(triphenylphosphine) chloride, and the like).

In addition to the above-described procedures, the deprotection reaction can be carried out, for example, by the methods described in T. W. Greene, Protective Groups in Organic synthesis, Wiley, New York, 1999.

The protective groups for carboxyl group include, for example, methyl, ethyl, allyl, t-butyl, trichloroethyl, benzyl (Bn), phenacyl, methoxybenzyl, trityl or 2-chlorotrityl group, or solid-phase carriers having these chemical structures bonded thereto.

The protecting groups for hydroxyl group include, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDPS), t-butyldiphenylsilyl (TBDPS), acetyl (Ac), pivaloyl, benzoyl, benzyl (Bn), methoxybenzyl, allyloxy-carbonyl (Alloc) or 2,2,2-trichloroethoxycarbonyl (Troc) group, and the like.

The protective groups for amino group include, for example, a benzyloxycarbonyl, t-butoxycarbonyl (Boc), allyloxycarbonyl (Alloc), 1-methyl-1-(4-biphenyl)-ethoxycarbonyl (Bpoc), trifluoroacetyl, 9-fluorenylmethoxy-carbonyl, benzyl (Bn), methoxybenzyl, benzyloxymethyl (BOM) or 2-(trimethylsilyl)ethoxymethyl (SEM) group, and the like The protective groups for thiol group include, for example, a benzyl (Bn), methoxybenzyl, methoxymethyl (MOM), 2-tetrahydropyranyl (THP), diphenylmethyl or acetyl group, and the like.

The protective groups for carboxyl, hydroxyl, amino or thiol group are not limited particularly to the above described ones, only if they are easily and selectively removable. For example, use may be made of those described in T. W. Greene, Protective Groups in Organic Synthesis, Wiley, New York, 1999.

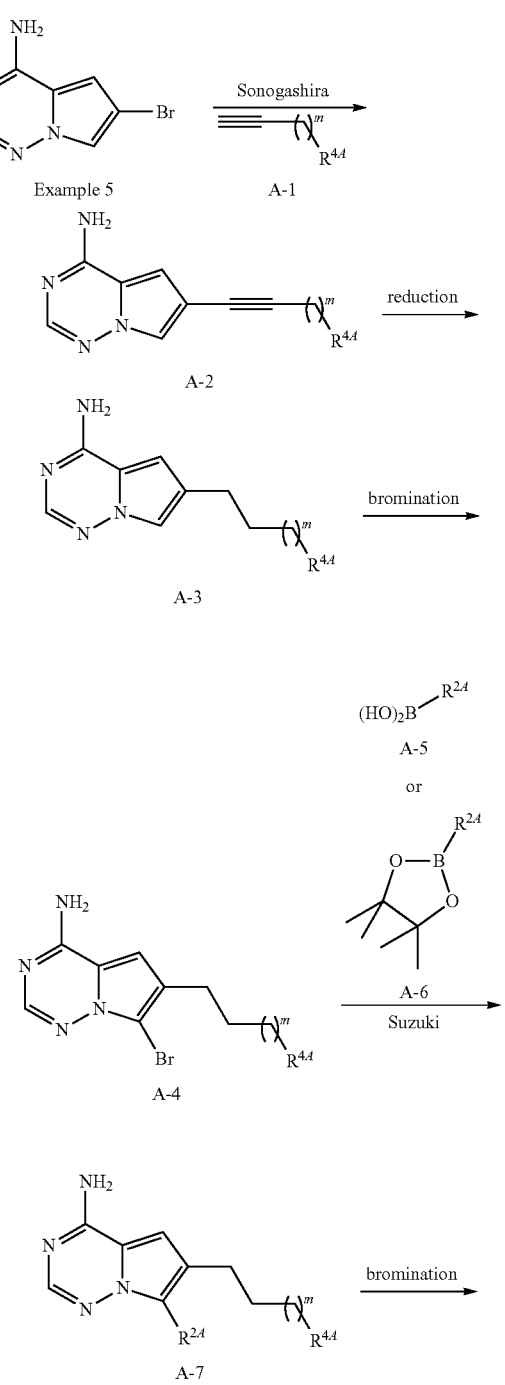

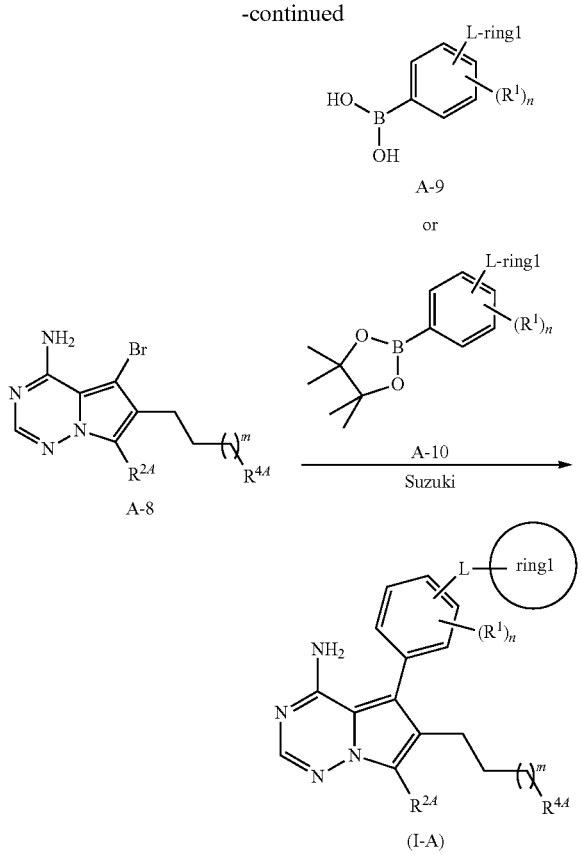

In the compounds represented by the formula (I), for example, the compounds wherein $R^2$ represents $R^{2A}$ and $R^4$ represents methylene substituted with $NR^{4-101}R^{4-102}$, i.e., the compound represented by formula (I-B);

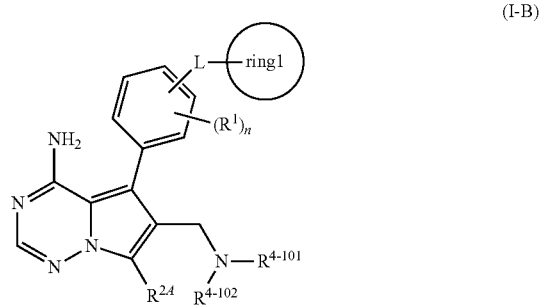

wherein ring1, $R^1$, L, $R^{2A}$, $R^{4-101}$, $R^{4-102}$ and n have the same meanings as the above described, can be produced by the below shown Scheme B.

The compounds of formula B-2 may be synthesized by a Stille coupling reaction with the compound corresponding to Example 5 and the compounds of formula B-1 (tributyl(vinyl) stannum). This reaction is a known method, and can be carried out, for example, in an organic solvent (such as toluene, benzene, N,N-dimethylformamide (DMF), tetrahydrofuran, methanol, acetonitrile, dimethoxyethane, acetone, and the like) and in the presence of a base (such as sodium hydroxide, potassium hydroxide, triethylamine, sodium carbonate, sodium hydrogen carbonate, potassium carbonate, and the like) in the presence of a lithium chloride and a palladium catalyst (such as tetrakis(triphenylphosphine)palladium (Pd (PPh$_3$)$_4$), dichlorobis(triphenylphosphine)palladium (Cl$_2$Pd (PPh$_3$)$_2$) and the like) at the temperature of 0° C. to reflux temperature.

The compounds of formula B-3 may be synthesized by an oxidation reaction of the compounds of formula B-2. This reaction is a known method, and can be carried out, for example, in an organic solvent (such as methanol, ethanol, tetrahydrofuran, dichloromethane, and the like) using ozone gas at the temperature of −78° C. to reflux temperature.

The compounds of formula B-5 may be synthesized by a reductive amination reaction with the compounds of formula B-3 and the compounds of formula B-4. This reaction is known method, and can be carried out, for example, in an organic solvent (such as dichloroethane, dichloromethane, dimethylformamide, acetonitrile, tetrahydrofuran, methanol, and the like) in the presence of a reductive agent (such as sodium tri(acetoxy) boron hydride, sodium cyanoboron hydride, sodium boron hydride, and the like) in the presence or absence of acid (such as acetic acid, trifluoroacetic acid, titanium propoxide, and the like) at the temperature of 0° C. to 40° C.

The process of producing the compound of formula (I-B) from the compound of formula B-5 shown in Scheme B can be carried out using in combination the bromination and Suzuki coupling reaction as above described.

Herein, the compound of formula B-7 may be reduced by the above described reduction reaction, if necessary.

In addition, in the compounds represented by formula (I), the compounds wherein $R^2$ represents $R^{2A}$ and $R^4$ represents methylene substituted 5-7 membered N-containing heterocyclic ring in ring4 can be produced using the corresponding cyclic amine instead of the compound formula B-4 according to Scheme B.

If the variable groups of the compounds described in the below scheme contain protective groups, the deprotection reaction for the protective group can be performed as necessary.

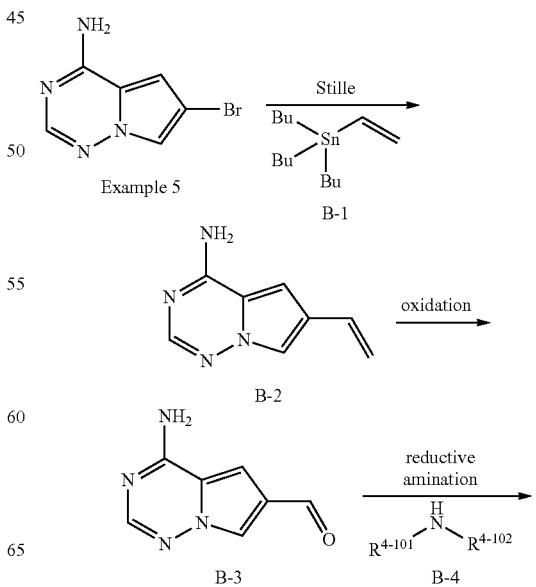

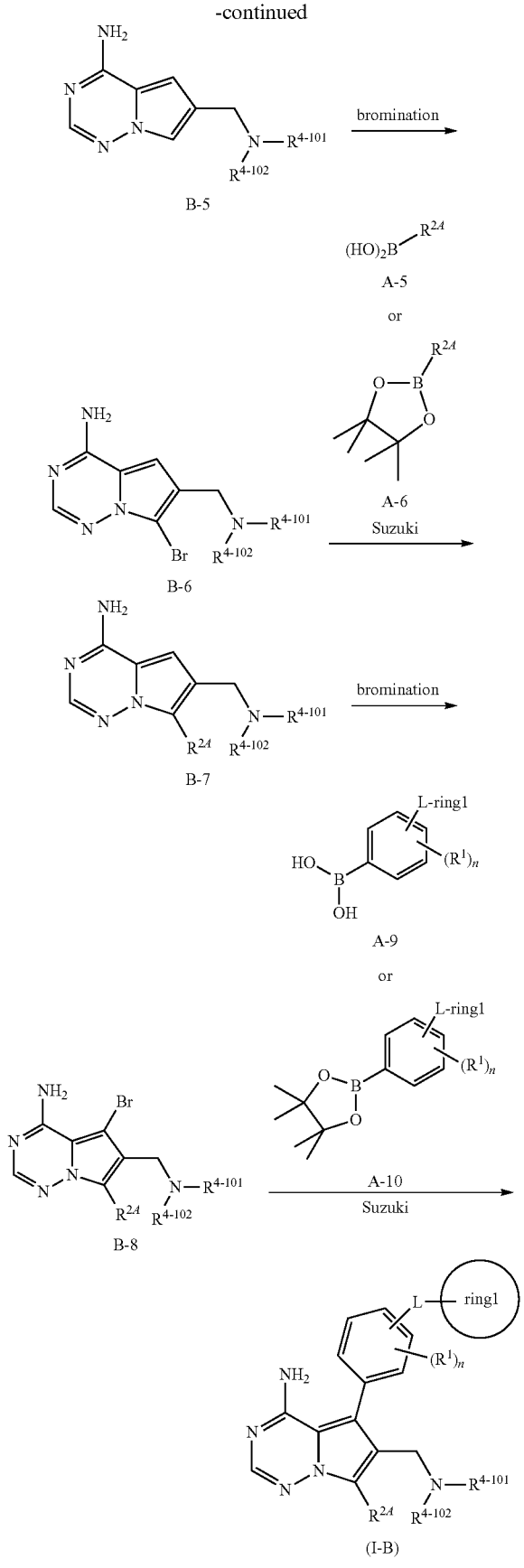

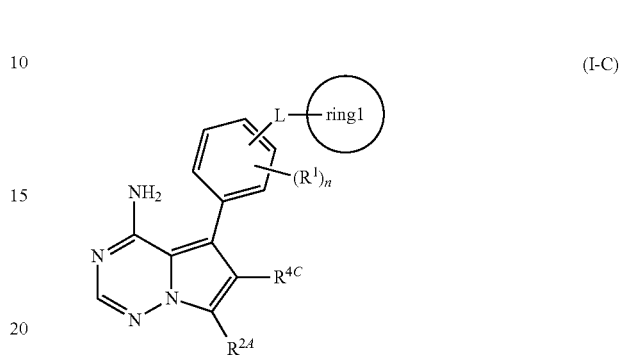

In the compounds represented by the formula (I), for example, the compounds wherein $R^2$ represents $R^{2A}$ and $R^4$ represents $R^{4C}$, i.e., the compound represented by formula (I-C);

wherein $R^{4C}$ is ring3, and ring1, $R^1$, L, $R^{2A}$ and n have the same meanings as the above described, can be produced by the below shown Scheme C.

The compound of formula C-2 may be synthesized by an alkylation reaction with the compound corresponding to Example 5 and the compounds of formula C-1. This reaction is a known method, and can be carried out, for example, in an organic solvent (such as toluene, benzene, N,N-dimethylformamide (DMF), tetrahydrofuran, methanol, acetonitrile, dimethoxyethane, acetone, and the like) and in the presence of a Grignard reagent (such as 2-propylmagnesium chloride, and the like) with or without a silane (such as chlorotrimethylsilane and the like) or an organolithium reagent (such as n-butyllithium, sec-butyllithium, tert-butyllithium, and the like) at the temperature of 0° C. to reflux temperature.

The compounds of formula C-3 may be synthesized by a dehydration reaction of the compounds of formula C-2. This reaction is a known method, and can be carried out, for example, in an organic solvent (such as toluene, benzene, N,N-dimethylformamide (DMF), tetrahydrofuran, methanol, acetonitrile, dimethoxyethane, acetone, and the like) and in the presence of an acid (such as hydrochloric acid, sulfuric acid, trifluoroacetic acid, trifluoroacetic anhydride, and the like) at the temperature of 0° C. to reflux temperature.

The compound of formula C-4 may be synthesized by the above described reductive reaction of the compounds of formula C-3.

The process of producing the compound of formula (I-C) from the compound of formula C-4 shown in Scheme C can be carried out using in combination the bromination and Suzuki coupling reaction as the above described.

Herein, the compound of formula C-6 may be reduced by the above described reduction reaction, if necessary.

If the variable groups of the compounds described in the below scheme contain protective groups, the deprotection reaction for the protective group can be performed as necessary.

Scheme C

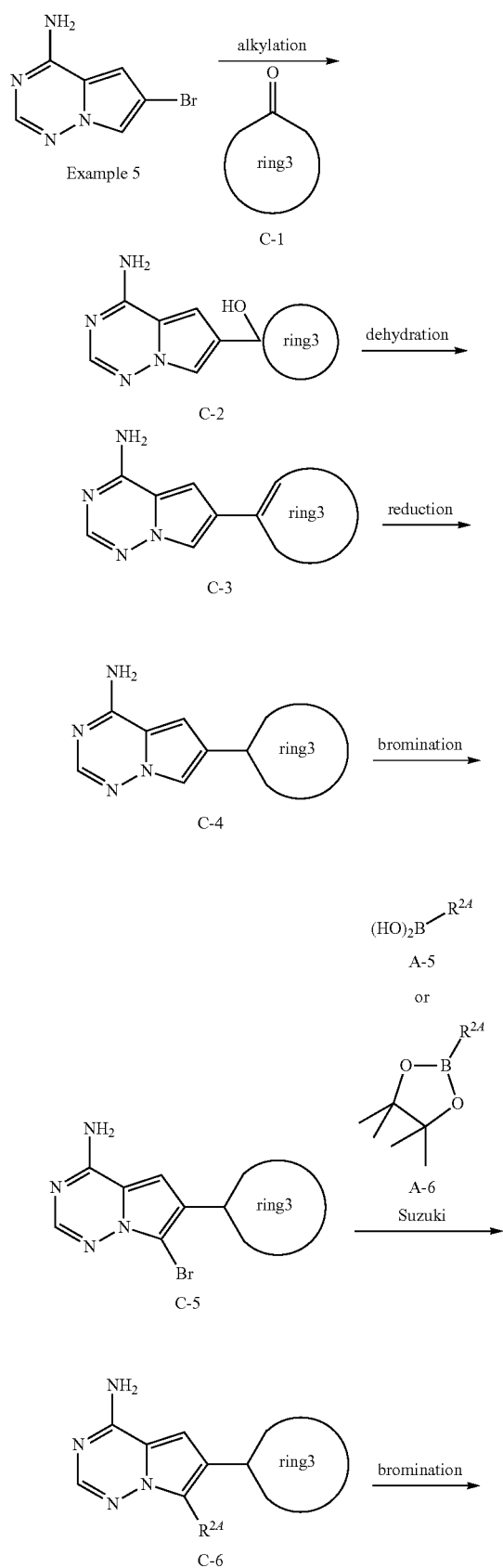

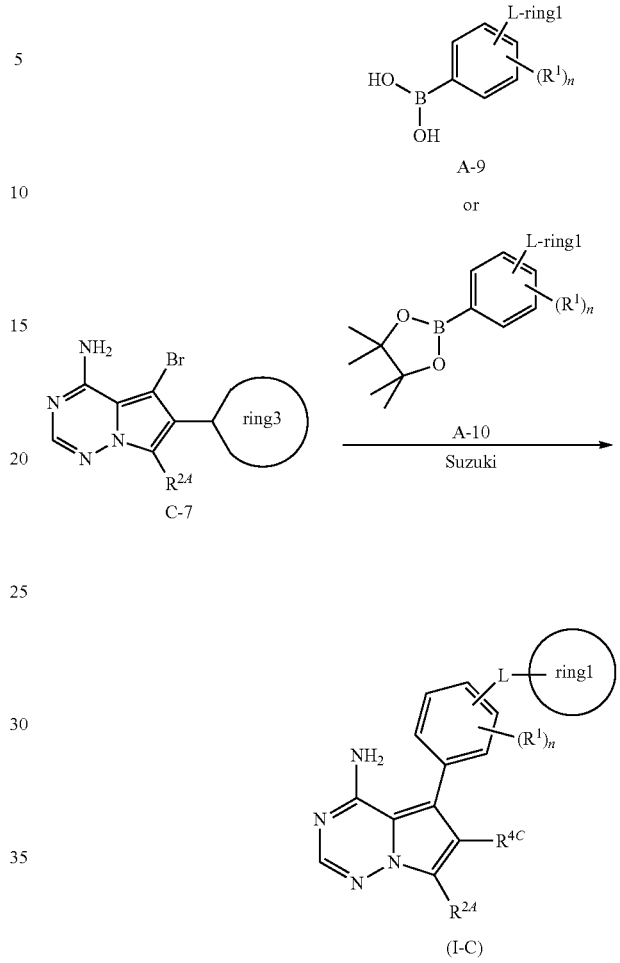

(I-C)

The compound of formula (I-C) can be also synthesized by the below shown Scheme D.

The compounds of formula D-3 may be synthesized by the above described Suzuki coupling reaction with the compound corresponding to Example 5 with the compounds of formula D-1 or D-2.

The compound of formula D-4 may be synthesized by the above described reductive reaction of the compounds of formula D-3.

The process which produces the compound of formula (I-C) from the compound of formula D-4 shown in Scheme D can be carried out using in combination the bromination and Suzuki coupling reaction as the above described.

Herein, the compound of formula D-6 may be reduced by the above described reduction reaction, if necessary.

If the variable groups of the compounds described in the below scheme contain protective groups, the deprotection reaction for the protective group can be performed as necessary.

Scheme D

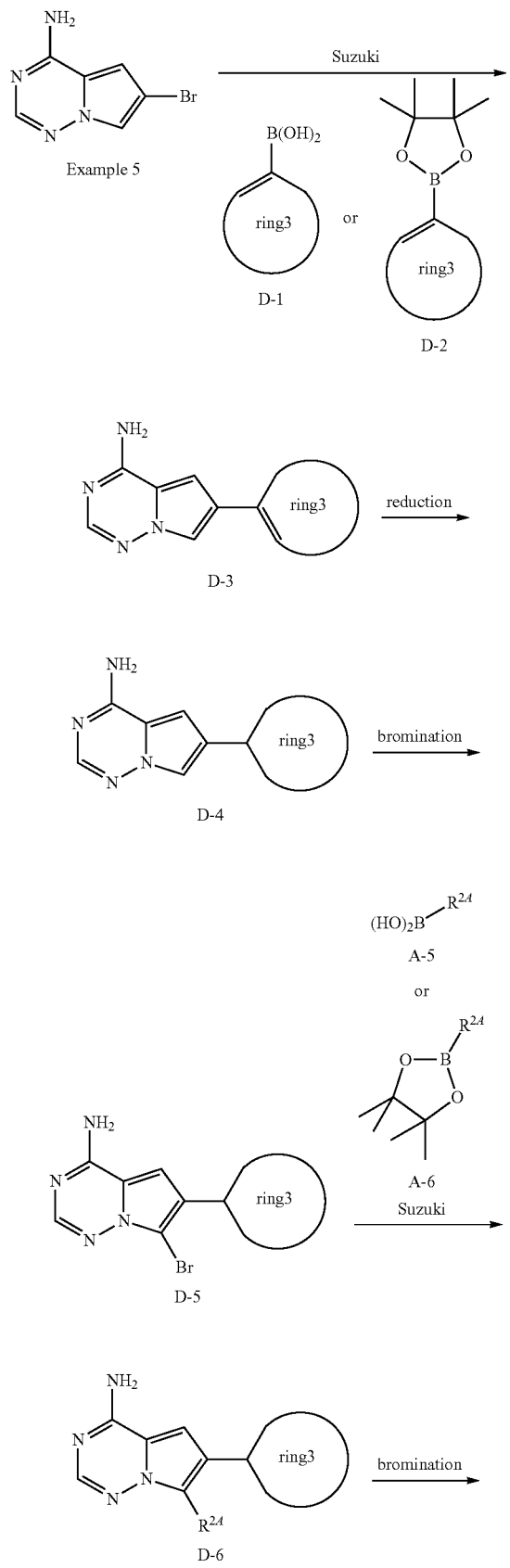

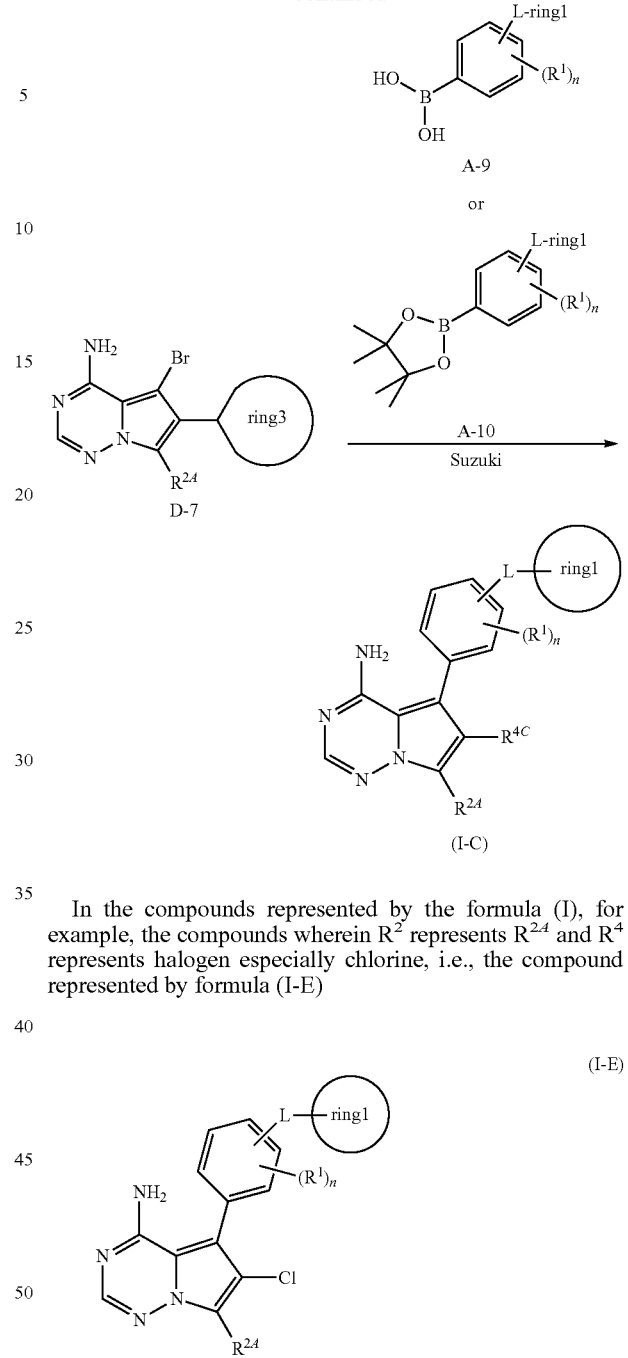

In the compounds represented by the formula (I), for example, the compounds wherein $R^2$ represents $R^{2A}$ and $R^4$ represents halogen especially chlorine, i.e., the compound represented by formula (I-E)

wherein ring1, $R^1$, L, $R^{2A}$ and n have the same meanings as the above described, can be produced by the below shown Scheme E.

The compound of formula E-2 may be synthesized by the above described Suzuki coupling reaction with the compound of formula E-1 prepared according to Example 5 with the compounds of formula A-5 or A-6.

Herein, the compound of formula E-2 may be reduced by the above described reduction reaction, if necessary.

The compounds of formula E-4 may be synthesized by the above described bromination and Suzuki coupling reaction with the compounds of formula E-2.

The compound of formula (I-E) may be synthesized by a chlorination of the compounds of formula E-4. This reaction is a known method, and can be carried out, for example, in an organic solvent (such as DMF, dichloromethane, tetrahydrofuran, acetic acid, and the like) with a chlorinating agent (such as 1,3-dichloro-5,5-dimethylimidazolidine-2,4-dione, chlorine, N-chlorosuccinimide, and the like) at the temperature of −78° C. to reflux temperature.

The compound, wherein $R^4$ is halogen other than chlorine, may be synthesized by the corresponding halogenation reaction (such as bromination and the like).

If the variable groups of the compounds described in the below scheme contain the protective groups, deprotection reaction for the protective group can be performed as necessary.

Scheme E

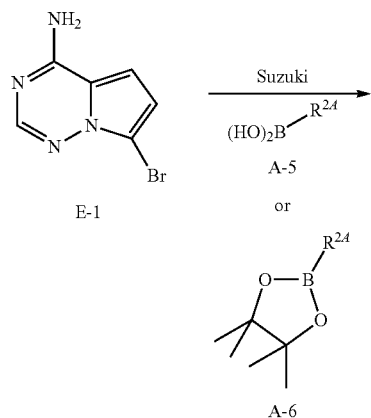

E-1

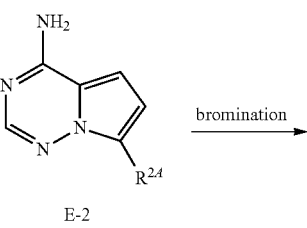

E-2

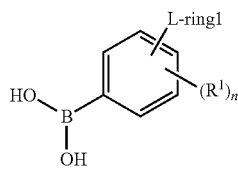

A-9 or

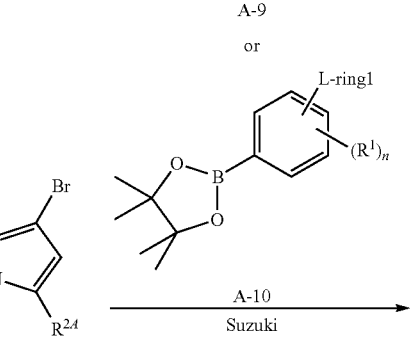

E-3

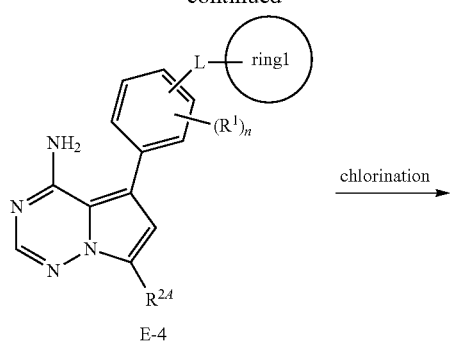

E-4

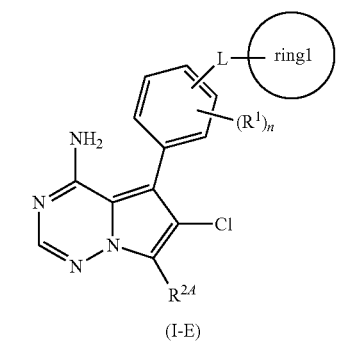

(I-E)

The compounds of formula I-E can also be synthesized by replacing the Suzuki step with an alkylation, dehydration, reduction sequence as shown in Scheme F.

Scheme F

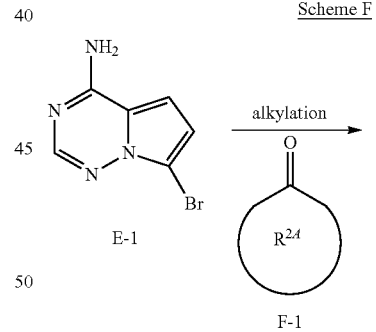

F-1

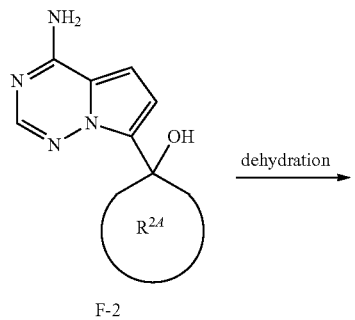

F-2

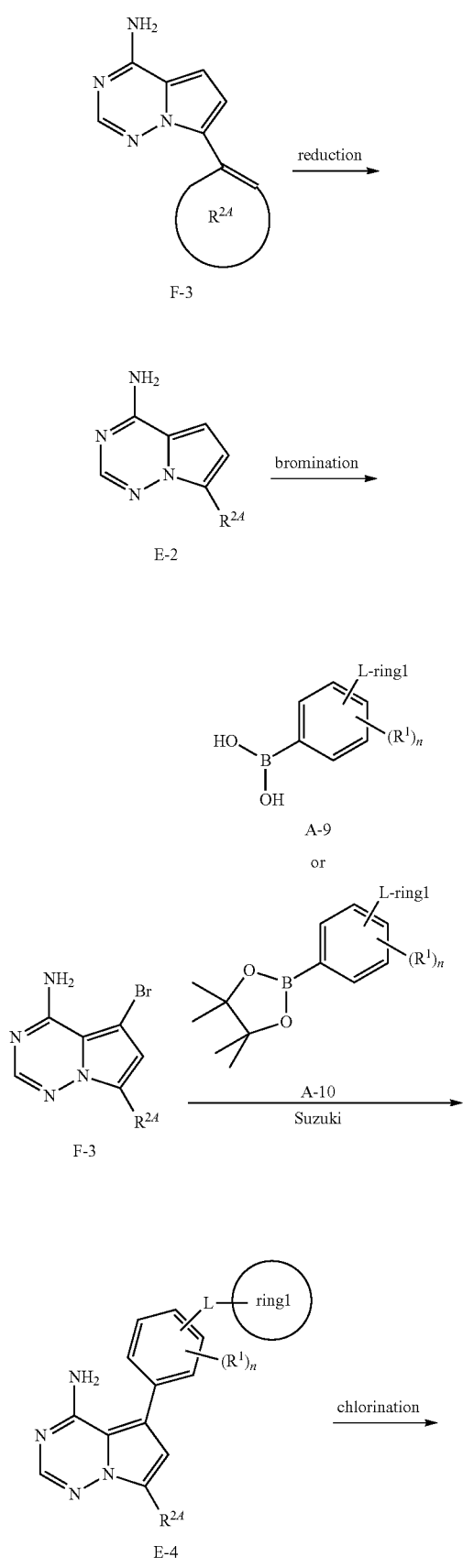

The above described compounds represented by the formulae A-1, A-5, A-6, A-9, A-10, B-1, B-4, C-1, D-1, D-2 and E-1 which are usable as a starting compound in the above described all the scheme are conventionally known or can be easily produced by utilizing the conventionally known methods, such as the procedures as described in "Comprehensive Organic Transformations: A Guide to Functional Group Preparations, $2^{nd}$ Edition (Richard C. Larock, John Wiley & Sons Inc., 1999)".

In the compounds of the present invention represented by the formula (I), any compounds other than the above described compounds can be synthesized by utilizing in combination the procedures or methods as described in Examples to be given in the present specification or the conventionally known methods, such as those described in "Comprehensive Organic Transformations: A Guide to Functional Group Preparations, $2^{nd}$ Edition (Richard C. Larock, John Wiley & Sons Inc., 1999).

In the respective reactions described in the present specification, any reactions being accompanied by heating can be carried out with use of a water bath, oil bath, sand bath or microwave, as may be self-evident to an ordinarily skilled person.

In the respective reactions described in the present specification, appropriate use may be made of solid-phase supported reagents having chemicals supported on high molecular polymers (such as polystyrene, polyacrylamide, polypropylene, polyethylene glycol, and the like).

In the respective reactions described in the present specification, the reaction products can be purified by ordinarily employed purification means, such as distillation under atmospheric pressure or reduced pressure, high-performance liquid chromatography using silica gel or magnesium silicate, thin-layer chromatography, ion exchange resins, scavenger resins or column chromatography, or such techniques as washing, recrystallization, and the like. Purification may be performed in the reaction-by-reaction manner or after completion of several reactions.

[Toxicity]

The toxicity of the compound represented by formula (I), a salt thereof, an N-oxide thereof, a solvate thereof or a prodrug thereof (herein, which may be abbreviated to "the compound of present invention", hereinafter) is very low, and thus it is considered that the compound is sufficiently safe to be used as a pharmaceutical agent.

[Application to Pharmaceutical Agent]

The compound of present invention can be used for a preventive and/or therapeutic agent of Btk related diseases, for example, an allergic disease, an autoimmune disease, an inflammatory disease, a thromboembolic disease, cancer, graft versus host disease, and the like.

In the present invention, allergic disease includes, for example, allergies, anaphylaxis, allergic conjunctivitis, allergic rhinitis, atopic dermatitis.

In the present invention, autoimmune disease includes, for example, inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Grave's disease, Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, vulvodynia, systemic lupus erythematosus.

In the present invention, inflammatory disease includes, for example, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis, myocarditis, myositis, nephritis, oophoritis, orchitis, osteitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, vulvitis.

In the present invention, thromboembolic disease includes, for example, myocardial infarct, angina pectoris, reocclusion after angioplasty, restenosis after angioplasty, reocclusion after aortocoronary bypass, restenosis after aortocoronary bypass, stroke, transitory ischemia, peripheral arterial occlusive disorder, pulmonary embolism, deep venous thrombosis.

In the present invention, cancer includes B cell lymphoma, for example, burkitt lymphoma, AIDS-related lymphoma, marginal zone B cell lymphoma (nodal marginal zone B cell lymphoma, extranodal marginal zone B cell lymphoma, splenic marginal zone lymphoma), diffuse large B cell lymphoma, primary effusion lymphoma, lymphomatoid granulomatosis, follicular lymphoma, B-cell chronic lymphocytic lymphoma, B cell prolymphocytic leukemia, lymphoplasmacytic lymphoma/Waldenstrom macroglobulinemia, plasmacytoma, mantle cell lymphoma, mediastinal large B cell lymphoma, intravascular B cell lymphoma.

The compound of the present invention may be administered as a combination preparation by combining with other pharmaceuticals for the purpose of;

1) supplementing and/or enhancing the preventive and/or treatment effect of the compound of the present invention, 2) improving pharmacokinetics and absorption of the compound, and reducing the dose of the compound of the present invention, and/or 3) reducing side effect of the compound of the present invention.

The combination preparations of the compound of the present invention and a concomitant drug(s) may be administered as one combination preparation comprising these components, or may be administered separately. When they are administered separately as independent preparations, they may be administered simultaneously or with time lag. Administration with time lag includes the method of administering the compound of the present invention before other drugs and vice versa, and each administration route may be the same or different. There is no limitation on a disease on which the combination preparations of the compound of the present invention and a concomitant drug(s) have preventive and/or treatment effects, so long as the preventive and/or treatment effect of the combination preparation is supplemented and/or enhanced in the disease. There is no limitation on the weight ratio between the compound of the present invention and the concomitant drug(s) in a combined preparation by combining the compound of the present invention with the concomitant drug(s).

Furthermore, the concomitant drug(s) is not limited to a low molecular weight compound, and may be a macromolecule protein, polypeptide, polynucleotide (such as DNA, RNA, gene, and the like), antisense, decoy, antibody, vaccine, and the like. The dosage of the concomitant drug(s) can be properly selected according to the clinical dosage. The compounding ratio of the compound of the present invention and the concomitant drug(s) can be properly selected by the age and body weight of the object, administration route, administration term, target disease, symptom, combination, and the like. For example, the amount of the concomitant drug(s) may be used 0.01 parts by weight to 100 parts by weight relative to 1 part by weight of the compound of the present invention.

The concomitant drug(s) may be administrated in the proper combination of arbitrary one or two or more member(s) selected from the same or different groups in arbitrary proportion.

The concomitant drug(s) for supplementation and/or enhancement of the preventive and/or therapeutic effect of the compound of the present invention includes not only those which have so far been found but also those which will be found on the basis of the aforementioned mechanism. The concomitant drug(s) which can be used in combination with the compounds of the present invention include, for example, those given below.

Examples of the concomitant drug(s) for supplementing and/or enhancing the preventive and/or therapeutic effect for allergic disease of the compound of the present invention include, for example, an anti-histaminic drug, an anti-leukotriene drug, an anti-allergic drug, a thromboxane A2 receptor antagonist, a thromboxane synthetase inhibitor, a steroid, and the like.

Examples of the concomitant drug(s) for supplementing and/or enhancing the preventive and/or therapeutic effect for autoimmune disease of the compound of the present invention include, for example, an immunosuppressant, a steroid, a disease modifying anti-rheumatic drug, an elastase inhibitor, a cannabinoid-2 receptor stimulator, a prostaglandin, a prostaglandin synthase inhibitor, a phosphodiesterase inhibitor, a metalloproteinase inhibitor, an adhesion molecule inhibitor, an anti-cytokine protein preparation such as an anti-TNF-αpreparation, an anti-IL-1 preparation, an anti-IL-6 preparation, a cytokine inhibitor, a non-steroidal antiinflammatory drug, and the like.

Examples of concomitant drug(s) for supplementing and/or enhancing the preventive and/or therapeutic effect for inflammatory disease of the compound of the present invention include, for example, a steroid, an elastase inhibitor, a cannabinoid-2 receptor stimulator, a prostaglandin, a prostaglandin synthase inhibitor, a phosphodiesterase inhibitor, a metalloproteinase inhibitor, an adhesion molecule inhibitor, anti-leukotriene drug, an anticholinergic drug, a thromboxane A2 receptor antagonist, a thromboxane synthetase inhibitor, β2-adrenaline receptor stimulator, a xanthine derivative, an expectorant, an antibacterial drug, an anti-histaminic drug, an anti-cytokine protein preparation, a cytokine inhibitor, a forskolin preparation, a mediator release inhibitor, a nonsteroidal antiinflammatory drug, and the like.

Examples of concomitant drug(s) for supplementing and/or enhancing the preventive and/or therapeutic effect for thromboembolic disease of the compound of the present invention include, for example, a thrombolytic drug, a heparin, a heparin analog, a low-molecular-weight heparin, a warfarin, a thrombin inhibitor, a factor Xa inhibitor, an ADP receptor antagonist, a cyclooxygenase inhibitor, and the like.

Examples of concomitant drug(s) for supplementing and/or enhancing the preventive and/or therapeutic effect for B-cell lymphoma of the compound of the present invention include, for example, an alkylating drug, an anti-metabolite, an antibiotics, a vegetable alkaloid drug, hormonal drug, a platinum-containing drug, other anti-cancer drugs, and the like.

Examples of the anti-histamic chug(s) include, for example, azelastine hydrochloride, ebastine, epinastine hydrochloride, emedastine difumarate, auranofin, oxatomide, olopatadine hydrochloride, d-chlorpheniramine maleate, clemastine fumarate, ketotifen fumarate, cimetidine, dimenhydrinate, diphenhydramine hydrochloride, cyproheptadine hydrochloride, cetirizine hydrochloride, desloratadine, terfenadine, famotidine, fexofenadine, fexofenadine hydrochloride, bepotastine, bepotastine besilate, mizolastine, mequitazine, mometasone furoate, ranitidine, ranitidine hydrochloride, loratadine, promethazine hydrochloride, homochlorcyclizine hydrochloride, and the like.

Examples of the anti-leukotriene drug(s) include, for example, pranlukast hydrate, montelukast sodium, zafirlukast, ablukast, pobilukast, sulukast, iralukast sodium, verlukast, ritolukast, cinalukast, pirodomast, tomelukast, doqualast, and the like.

Examples of the anti-allergic drug(s) include, for example, amlexanox, azelastine hydrochloride, israpafant, ibudilast, imitrodast sodium, ebastine, epinastine hydrochloride, emedastine difumarate, oxatomide, ozagrel hydrochloride, olopatadine hydrochloride, cromoglicate, sodium cromoglicate, ketotifen fumarate, seratrodast, cetirizine hydrochloride, suplatast tosilate, tazanolast, terfenadine, domitroban calcium hydrate, tranilast, nedocromil, fexofenadine, fexofenadine hydrochloride, pemirolast potassium, mequitazine, ramatroban, repirinast, loratadine, and the like.

Examples of the thromboxane A2 receptor antagonist include, for example, seratrodast, domitroban calcium hydrate, ramatroban, and the like.

Examples of the thromboxane synthetase inhibitor include, for example, imitrodast sodium, ozagrel hydrochloride, and the like.

Examples of the steroid include, for example, amcinonide, hydrocortisone sodium succinate, prednisolone sodium succinate, methylprednisolone sodium succinate, ciclesonide, difluprednate, betamethasone dipropionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfonate, mometasone furoate, fluocinonide, fluocinolone acetonide, fludroxycortide, flunisolide, prednisolone, alclometasonedi propionate, clobetasol propionate, dexamethasone propionate, deprodone propionate, fluticasone propionate, beclometasone dipropionate, betamethasone, methylprednisolone, methylprednisolone suleptanate, methylprednisolone sodium succinate, mometasone furoate, dexamethasone sodium phosphate, hydrocortisone sodium phosphate, prednisolone sodium phosphate, diflucortolone valerate, dexamethasone valerate, betamethasone valerate, prednisolone valerate-acetate, cortisone acetate, diflorasone diacetate, dexamethasone acetate, triamcinolone acetate, paramethason acetate, halopredone acetate, fludrocortisone acetate, prednisolone acetate, methylprednisolone acetate, hydrocortisone butyrate, hydrocortisone butyrate propionate, betamethasone butyrate propionate, and the like.

Examples of the immunosuppressant include, for example, azathioprine, ascomycin, everolimus, salazosulfapyridine, cyclosporine, cyclophosphamide, sirolimus, tacrolimus, bucillamine, methotrexate, leflunomide, and the like.

Examples of the disease modifying anti-rheumatic drug include, for example, D-penicillamine, actarit, auranofin, salazosulfapyridine, hydroxychloroquine, bucillamine, methotrexate, leflunomide, lobenzarit disodium, aurothioglucose, sodium aurothio malate, and the like.

Examples of the elastase inhibitor include, for example, ONO-5046, ONO-6818, MR-889, PBI-1101, EPI-HNE-4, R-665, ZD-0892, ZD-8321, GW-311616, DMP-777, L-659286, L-658758, L-680833, L-683845, AE-3763, and the like.

Examples of the prostaglandin (hereinafter, abbreviated as PG) include, for example, PG receptor agonists, PG receptor antagonists, and the like.

Examples of the PG receptor include PGE receptors ($EP_1$, $EP_2$, $EP_3$ and $EP_4$), PGD receptors (DP, CRTH2), PGF receptors (FP), PGI receptors (IP), TX receptors (TP), and the like.

Examples of the prostaglandin synthase inhibitor include, for example, alazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam betadex, piroxicam cinnamate, tropineindometacinate, zaltoprofen, pranoprofen, and the like.

Examples of the phosphodiesterase include, for example, PDE4 inhibitors such as rolipram, cilomilast (trade name: Ariflo), Bay19-8004, NLK-616, roflumilast (BY-217), cipamfylline (BRL-61063), atizoram (CP-80633), SCH-351591, YM-976, V-11294A, PD-168787, D-4396, IC-485, PDE5 inhibitors such as sildenafil, and the like.

Examples of the adhesion molecule inhibitor include, for example, α4 integrin antagonist, and the like.

Examples of the anti-TNF-α preparation include antibody against TNF-α, soluble TNF-α receptor, antibody against TNF-α receptor, soluble TNF-α receptor binding protein, and specifically, infliximab, etanercept, and the like.

Examples of the anti-IL-1 preparation include antibody against IL-1, soluble IL-1 receptor, antibody against IL-1Ra and/or IL-1 receptors, and specifically, for example, anakinra, and the like.

Examples of the anti-IL-6 preparation include antibody against IL-6, soluble IL-6 receptor, antibody against 11-6 receptor, and for example, tocilizumab, and the like.

Examples of the cytokine inhibitor include suplatast tosylate (trade name: IPD), T-614, SR-31747, sonatimod, and the like.

Examples of the steroidal agent include clobetasol propionate, diflorasone diacetate, fluocinonide, mometasone furoate, betamethasone dipropionate, betamethasone butyrate propionate, betamethasone valerate, difluprednate, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate-acetate, fluocinolone acetonide, beclometasone dipropionate, triamcinolone acetonide, flumetasone pivalate, alclometasone dipropionate, clobetasone butyrate, prednisolone, fludroxycortide, cortisone acetate, hydrocortisone, hydrocortisone sodium phosphate, hydrocortisone sodium succinate, fludrocortisone acetate, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, dexamethasone sodium phosphate, dexamethasone palmitate, paramethasone acetate, betamethasone, fluticasone propionate, budesonide, flunisolide, ST-126P, ciclesonide, dexamethasone palomithionate, mometasone furoate, prasterone sulfonate, deflazacort, methylprednisolone suleptanate, methylprednisolone sodium succinate, and the like.

Examples of the anticholinergic drug include, for example, trihexyphenidyl, trihexyphenidyl hydrochloride, biperiden, biperiden hydrochloride, and the like.

Examples of the β2 Adrenaline receptor stimulator include, for example, fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenalinemesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, formoterol, KUR-1246, KUL-7211, AR-C89855, S-1319, and the like.

Examples of the xanthine derivative include, for example, aminophylline, theophylline, doxofylline, sipamphylline, diprophylline, and the like.

Examples of the expectorant agent include foeniculated ammonia spirit, sodium hydrogen carbonate, bromhexine hydrochloride, carbocysteine, ambroxol hydrochloride, ambroxol hydrochloride sustained preparation, methylcysteine hydrochloride, acetylcysteine, ethyl L-cysteine hydrochloride, tyloxapol, and the like.

Examples of the antibacterial drug include sodium cefuroxime, meropenem trihydrate, netilmicin sulfate, sisomicin sulfate, ceftibuten, PA-1806, IB-367, tobramycin, PA-1420, doxorubicin, astromicin sulfate, cefetamet pivoxil hydrochloride, and the like.

Examples of the mediator release inhibitor include tranilast, sodium cromoglicate, amlexanox, repirinast, ibudilast, dazanolast, pemirolast potassium, and the like.

Examples of the thrombolytic drug include, for example, alteplase, urokinase, tisokinase, nasaruplase, nateplase, tissue plasminogen activator; t-PA, pamiteplase, monteplase, prourokinase, streptokinase, and the like.

Examples of the heparin analog include, for example, fondaparinux, and the like.

Examples of the low-molecular-weight heparin include, for example, danaparoid sodium, enoxaparin (sodium), nadroparin calcium, bemiparin (sodium), reviparin (sodium), tinzaparin (sodium), and the like.

Examples of the thrombin inhibitor include, for example, argatroban, ximelagatran, melagatran, dabigatran, bivalirudin, lepirudin, hirudin, desirudin, and the like.

Examples of the ADP receptor antagonist include, for example, ticlopidine hydrochloride, clopidogrel sulfate, and the like.

Examples of the cyclooxygenase inhibitor include, for example, aspirin, and the like.

Examples of the alkylating drug include, for example, nitrogen mustard N-oxide hydrochloride, cyclophosphamide, ifosfamide, melphalan, thiotepa, carboquone, busulfan, nimustine hydroxychloride, dacarbazine, ranimustine, and the like.

Examples of the anti-metabolite include, for example, methotrexate, mercaptopurine, 6-mercaptopurine riboside, fluorouracil, tegafur, tegafur/uracil, carmofur, doxifluridine, cytarabine, enocitabine, tegafur/gimestat/otastat, gemcitabine hydrochloride, cytarabine ocfosfate, procarbazine hydrochloride, hydroxycarbamide, and the like.

Examples of the antibiotics include, for example, actinomycin D, mitomycin C, daunorubicin hydrochloride, doxorubicin hydrochloride, aclarubicin hydrochloride, neocarzinostatin, pirarubicin hydrochloride, epirubicin hydrochloride, idarubicin hydrochloride, chromomycin A3, bleomycin hydrochloride, peplomycin sulfate, therarubicin, zinostatin stimalamer, and the like.

Examples of the vegetable alkaloid drug include, for example, vinblastine sulfate, vincristine sulfate, vindesine sulfate, irinotecan hydrochloride, etoposide, flutamide, vinorelbine ditartrate, docetaxel hydrate, paclitaxel, and the like.

Examples of the hormonal drug include, for example, estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, exemestane, and the like.

Examples of the platinum-containing drug include, for example, carboplatin, cisplatin, nedaplatin, and the like.

Examples of the other anti-cancer drugs include, for example, L-asparaginase, octreotide acetate, porfimer sodium, mitoxantrone hydrochloride, and the like.

In order to use the compounds of the present invention, or the compounds of the present invention in combination with the other pharmaceutical preparations by the above described purpose, these compounds are normally administered systemically or topically, and orally or parenterally.

The dose of the compounds of the present invention depends on age, body weight, symptom, therapeutic effect, administration method, treatment period and so on. In practice, however, these compounds are administered orally once or several times per day each in an amount of from 100 μg to 1000 mg per adult, parentally once or several times per day each in an amount of from 50 μg to 500 mg per adult or continuously administered into vein for 1 hour to 24 hours per day.

The dose of these compounds may be less than the above described dose or may need to exceed the above described range because the dose varies under various conditions as above described.

When the compounds of the present invention, or the compounds of the present invention are administered in combination with the other pharmaceutical preparations, they are used in the form of solid or liquid agent for oral administration, injection, agent for external application, suppository, eye drops or inhalant for parenteral administration, and the like.

Examples of the solid agent for oral administration include tablet, pill, capsule, powder, and pellet. Examples of the capsule include hard capsule, and soft capsule. In such a solid agent for internal application, one or more active materials are used in the form of preparation produced by an ordinary method singly or in admixture with a vehicle (such as lactose, mannitol, glucose, microcrystalline cellulose, starch, and the like), binder (such as hydroxypropyl cellulose, polyvinyl pyrrolidone, magnesium metasilicoaluminate, and the like), disintegrant (such as calcium fibrinoglycolate and the like), glidant (such as magnesium stearate and the like), stabilizer, dissolution aid (such as glutamic acid, aspartic acid and the like) or the like. The solid agent may be coated with a coating agent (such as white sugar, gelatin, hydroxypropyl cellulose, hydroxypropyl methyl cellulose phthalate, and the like) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (such as purified water, ethanol, mixture thereof and the like). Furthermore, such a liquid agent may comprise a wetting agent, a suspending agent, an emulsifier, a sweetening agent, a flavor, a fragrance, a preservative, a buffer, and the like.

The agent for parenteral administration may be in the form of, such as ointment, gel, cream, wet compress, paste, liniment, nebula, inhalant, spray, aerosol, eye drops, collunarium, and the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (such as adipic acid, myristic acid, palmitic acid, stearic acid, oleic acid, adipic acid ester, myristic acid ester, palmitic acid ester, stearic acid ester, oleic acid ester, and the like), wax (such as beeswax, whale wax, ceresin, and the like), surface active agent (such as polyoxyethylenealkylether phosphoric acid ester, and the like), higher alcohol (such as cetanol, stearyl alcohol, setostearyl alcohol, and the like), silicon oil (such as dimethyl polysiloxane and the like), hydrocarbon (such as hydrophilic petrolatum, white petrolatum, purified lanolin, liquid paraffin, and the like), glycol (such as ethylene glycol, diethylene glycol, propylene glycol, polyethylene glycol, macrogol, and the like), vegetable oil (such as castor oil, olive oil, sesame oil, turpentine oil, and the like), animal oil (such as mink oil, vitelline oil, squalane, squalene, and the like), water, absorption accelerator and rash preventive may be used singly or in admixture of two or more thereof. The base may further comprise a humectant, a preservative, a stabilizer, an antioxidant, a perfume, and the like.

The gel is prepared by any known or commonly used formulation. For example, one or more active materials are dissolved in a base to prepare such a gel. The gel base is selected from known or commonly used materials. For example, lower alcohol (such as ethanol, isopropyl alcohol and the like), gelling agent (such as carboxymethyl cellulose, hydroxyethyl cellulose, hydroxypropyl cellulose, ethyl cellulose, and the like), neutralizing agent (such as triethanolamine, diisopropanolamine and the like), surface active agent (such as polyethylene glycol monostearate and the like), gums, water, absorption accelerator, and rash preventive are used singly or in admixture of two or more thereof. The gel base may further comprise a preservative, an antioxidant, a perfume, and the like.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (such as propylene glycol, 1,3-butylene glycol and the like), higher alcohol (such as 2-hexyl decanol, cetanol and the like), emulsifier (such as polyoxyethylene alkyl ethers, aliphatic acid esters and the like), water, absorption accelerator, and rash preventive are used singly or in admixture of two or more thereof. The cream base may further comprise a preservative, an antioxidant, a perfume, and the like.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (such as polyacrylic acid, polyvinyl pyrrolidone, gum arabic, starch, gelatin, methyl cellulose, and the like), wetting agent (such as urea, glycerin, propylene glycol and the like), filler (such as kaolin, zinc oxide, talc, calcium, magnesium, and the like), water, dissolution aid, tackifier, and rash preventive may be used singly or in admixture of two or more thereof. The wet compress base may further comprise a preservative, an antioxidant, a perfume, and the like.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a preservative, an antioxidant, a perfume, and the like.

The liniment is prepared by any known or commonly used formulation. For example, one or more active materials are dissolved, suspended or emulsified in water, alcohol (such as ethanol, polyethylene glycol and the like), higher aliphatic acid, glycerin, soap, emulsifier, suspending agent, and the like, singly or in combination of two or more thereof, to prepare such a liniment. The liniment may further comprise a preservative, an antioxidant, a perfume, and the like The nebulizer, inhalant, spray and aerosol each may comprise a commonly used diluent, additionally, a stabilizer such as sodium hydrogen sulfite and a buffer capable of providing isotonicity such as isotonic agent (such as sodium chloride, sodium citrate, citric acid, and the like).

The injection for parenteral administration consists of solid injection which is dissolved or suspended in the form of solution, suspension, emulsion and a solvent to be dissolved before use. The injection is prepared by dissolving, suspending or emulsifying one or more active materials in a solvent. As such a solvent, distilled water for injection, physiological saline, vegetable oil, alcohol such as propylene glycol, polyethylene glycol and ethanol, and the like, singly or in combination thereof is used. The injection may further comprise a stabilizer, a dissolution aid (such as glutamic acid, aspartic acid, Polysolvate 80 (trade name), and the like), a suspending agent, an emulsifier, a soothing agent, a buffer, a preservative, and the like. The injection is sterilized at the final step or prepared by an aseptic process. Alternatively, an aseptic solid agent such as freeze-dried product which has previously been prepared may be rendered aseptic or dissolved in aseptic distilled water for injection or other solvents before use.

The eye drops for parenteral administration consist of eye drop, suspension eye drop, emulsion eye drop, eye drop to be dissolved before use and ointment and the like.

These eye drops are prepared by a known method. For example, it is prepared by dissolving, suspending or emulsifying one or more active materials in a solvent. As such a solvent for eye drops, physiological saline, the other aqueous solvent or nonaqueous solvent for injection (such as vegetable oil and the like), and the like, singly or in combination thereof is used. The eye drops may comprise, if necessary, of materials properly selected from tonicity agent (such as sodium chloride, concentrated glycerin and the like), buffer agents (such as sodium phosphate, sodium acetate and the like), surfactants (such as polysorbate 80 (trade name), polyoxyl 40 stearate, polyoxyethylene hydrogenated castor oil, and the like), stabilizer (such as sodium citrate, sodium edentate and the like), antiseptic agent (such as benzalkonium chloride, paraben and the like). These are sterilized at the final step or prepared by an aseptic process. Alternatively, an aseptic solid agent such as freeze-dried product which has previously been prepared may be rendered aseptic or dissolved in aseptic distilled water for injection or other solvents before use.

The inhalant for parenteral administration may be in the form of aerosol, powder for inhalation or liquid for inhalation. The liquid for inhalation may be dissolved or suspended in water or other proper medium in use.

These inhalants are prepared by a known method.

For example, the liquid for inhalation is prepared from materials properly selected from preservatives (such as benzalconium chloride, Paraben and the like), colorants, buffering agents (such as sodium phosphate, sodium acetate and the like), isotonic agents (such as sodium chloride, concentrated glycerin and the like), thickening agents (such as carboxyvinyl polymer and the like), absorption accelerators, and the like as necessary.

The powder for inhalation is prepared from materials properly selected from glidants (such as stearic acid and salt thereof and the like), binders (such as starch, dextrin and the like), vehicles (such as lactose, cellulose and the like), colorants, preservatives (such as benzalconium chloride, Paraben and the like), absorption accelerators, and the like, if necessary.

In order to administer the liquid for inhalation, a sprayer (such as atomizer, nebulizer and the like) is normally used. In order to administer the powder for inhalation, a powder inhaler is normally used.

Other examples of the composition for parenteral administration include suppository for rectal administration and pessary for vaginal administration prepared by an ordinary formulation comprising one or more active materials.

EFFECT OF THE INVENTION

Since the compounds of the present invention have selective Btk inhibitory activity, it could be useful for therapy for an allergic disease, an autoimmune disease, an inflammatory disease, a thromboembolic disease, a cancer, graft versus host disease and the like.

BEST MODE FOR CARRYING OUT THE INVENTION

The present invention is described below in detail by reference to the following Examples, however, the present invention is not interpreted as being restricted thereto.

The solvents in parentheses at chromatographic separations section and TLC section show the developing or eluting solvents and the ratios of the solvents used are indicated by volume. Unless otherwise indicated, the NMR data are $^1$H-NMR data. The solvents in parentheses indicated in NMR section show solvents used in determination.

The LC/MS data are indicated in below procedure. Unless otherwise indicated, (LCMS) shows m/z value and RT means retention time. Electron impact mass spectra (EI-MS) were obtained with a Waters Micromass ZQ equipped with a Waters Alliance HT 2795 LC with a Waters Sunfire C-18 column (4×6 mm, 5 microns, Waters Corp, Milford, Mass., USA). The ion source was maintained at 100° C. and spectra were scanned from 105-1200 amu at 0.4 sec per scan.

Electrospray mass spectra (HPLC ES-MS) were obtained using a Waters Alliance HT 2795 HPLC (Waters Corp, Milford, Mass., USA) equipped with dual pumps, a dual wavelength detector set at 254 nm, and a Waters Micromass ZQ (Waters Corp, Milford, Mass., USA). Spectra were scanned from 105-1200 amu using a variable ion time according to the number of ions in the source. The eluents were A: 5% acetonitrile in water with 0.1% trifluoroacetic acid (TFA) and B: acetonitrile with 0.1% TFA. Gradient elution from 1.0% B to 95% over 5.0 minutes at a flowrate of 3.5 ml/min was used with an initial hold of 0.3 minutes and a finial hold at 95% B of 0.3 minutes. Total run time was 5.0 minutes.

Example 1 tert-butyl 1H-pyrrol-1-ylcarbamate

Under an atmosphere of nitrogen, a solution of 2,5-dimethoxytetrahydrofuran (400 g, 3.03 mol) and tert-butyl carbazate (364 g, 2.75 mol) in 1,4-dioxane (2.5 L) were combined in a flask. Then, aqueous hydrochloric acid solution (2N, 35.8 mL, 71.5 mmol) was added dropwise and the reaction mixture was stirred for 21 hours at 85° C. The reaction mixture was treated with saturated sodium carbonate aqueous solution (120 mL) at room temperature. The quenched mixture was filtered to give a precipitate which was dried to give the title compound as a gray solid (250 g). The organic phase of the filtrate was concentrated and the resultant precipitate was washed with diisopropyl ether (200 mL) and filtered to give the title compound as a gray solid (60 g). The residue was purified by column chromatography on silica gel (hexane:ethyl acetate=4:1→3:1→2:1) to obtain the title compound (47 g). A total of 357 g of the title compound having the following physical data was obtained.

TLC: Rf=0.52 (hexane:ethyl acetate=3:1);
$^1$H NMR (300 MHz, CDCl$_3$) δ ppm 1.49 (s, 9H) 6.12 (t, J=2.3 Hz, 2H) 6.67 (t, J=2.3 Hz, 2H) 7.15 (s, 1H).

Example 2 text-butyl (2-cyano-1H-pyrrol-1-yl)carbamate

Under an atmosphere of nitrogen, the suspension of the compound (322 g) prepared in Example 1 in acetonitrile (2 L) was added into a flask. The solution was cooled to −7° C. Chlorosulfonyl isocyanate (162 mL, 1.86 mol) was dropped into the solution and was stirred for an hour at 0° C. Then, N,N-dimethylformamide (DMF) (325 mL) was dropped into the mixture and stirred for an hour at 5° C. The reaction solution was poured into iced water (4 L) and the aqueous layer was extracted with ethyl acetate. The combined organic layers were dried over anhydrous sodium sulfate and solvent removed under reduced pressure. The residue was purified by column chromatography on silica gel (hexane:ethyl acetate=1:0→4:1→3:1→3:2). The obtained solids were washed in hexane/diisopropylether (1:1; 400 mL) to obtain the title compound (148 g) as a white solid. The filtrate was concentrated and washed in hexane/diisopropylether (10:1; 300 mL) to obtain the title compound (112 g) as a white solid. A total of 260 g of the title compound having the following physical data was obtained.

TLC: Rf 0.42 (hexane:ethyl acetate=3:1);
$^1$H NMR (300 MHz, CDCl$_3$) δ ppm 1.52 (s, 9H) 6.19 (dd, J=4.4, 2.9 Hz, 1H) 6.79 (dd, J=4.4, 1.8 Hz, 1H) 6.90 (dd, J=2.9, 1.8 Hz, 1H) 7.26 (s, 1H).

Example 3 tert-butyl (4-bromo-2-cyano-1H-pyrrol-1-yl)carbamate

Under an atmosphere of nitrogen, a solution of the compound (270 g) prepared in Example 2 in acetonitrile was added into a flask and was cooled to −30° C. 1,3-Dibromo-5,5-dimethylimidazolidine-2,4-dione (205 g) was added into the solution then the bath was removed and the reaction was allowed to warm to room temperature. The solution was added into water. The aqueous layer was extracted with ethyl acetate. The combined organic layers were washed in saturated sodium chloride aqueous solution, were dried over anhydrous sodium sulfate and solvent removed under reduced pressure. The residue was purified by column chromatography on silica gel (hexane:ethyl acetate=9:1→5:1) to obtain the title compound (423 g) having the following physical data as a yellow oily matter.
TLC: Rf 0.44 (hexane:ethyl acetate=3:1);
$^1$H NMR (300 MHz, CDCl$_3$) δ ppm 1.52 (s, 9H) 6.78 (dd, J=1.8, 0.6 Hz, 1H) 6.92 (dd, J=1.8, 0.6 Hz, 1H) 7.31 (s, 1H).

Example 4

1-amino-4-bromo-1H-pyrrol-2-carbonitrile

Under an atmosphere of nitrogen, a solution of the compound (264 g) prepared in Example 3 in 1,4-dioxane (0.8 L) was added into a flask and hydrochloric acid/dioxane (4N, 1.25 L) was added into the solution in ice. The mixture was stirred overnight at 25° C. The reaction mixture was diluted with diisopropyl ether (1.5 L), and was filtered. The solids were washed with diisopropylether, then hexane to give the title compound (158 g) having the following physical data as a white solid.
TLC: Rf 0.31 (hexane:ethyl acetate=3:1);
$^1$H NMR (300 MHz, CD$_3$OD) δ ppm 6.71 (d, J=2.0 Hz, 1H) 7.03 (d, J=2.0 Hz, 1H).

Example 5

6-bromopyrrolo[2,1-f][1,2,4]triazin-4-amine

Under an atmosphere of nitrogen, a solution of the compound (118 g) prepared in Example 4 in ethanol was added into a flask. To the solution were added with formamidine acetate (275 g) and tripotassium phosphate (2.65 mol) and the mixture was stirred overnight at 78° C. The mixture was cooled to room temperature, was treated with methanol (500 mL) and tetrahydrofuran (THF) (1.5 L), and filtered through Celite™. The solvent was removed under reduced pressure. The reaction mixture was washed with water, then filtered. The solids were washed with water. The residue was dried under reduced pressure to a brown solid. The brown solid was diluted with THF (500 mL), added to silica gel (500 g) and the solvent was removed under reduced pressure. The residue was purified by column chromatography on silica gel (hexane:ethyl acetate=1:1→1:2→1:3). The obtained yellow solid (210 g) was washed in ethyl acetate/hexane (1:1), filtered, washed with hexane and then dried to give the title compound (160 g) having the following physical data as a white solid.

TLC: Rf 0.28 (hexane:ethyl acetate=1:1);
$^1$H NMR (300 MHz, DMSO-d$_6$) δ 6.95 (d, J=1.8 Hz, 1H) 7.79 (d, J=1.8 Hz, 1H) 7.81 (s, 1H) 7.84 (s, 2H).

Example 6

1-(3-chlorophenoxy)-2-methoxy-4-nitrobenzene

In a 250 mL round-bottom flask was added 3-chlorophenol (4.13 g, 32.1 mmol), 1-fluoro-2-methoxy-4-nitrobenzene (5.00 g, 29.2 mmol), potassium carbonate (6.06 g, 43.8 mmol) and acetonitrile (25 mL). The reaction was heated to 95° C. for 48 hours. The reaction was cooled to room temperature and was purified by column chromatography on silica gel (hexane/ethyl acetate=3:1). The reaction was poured into sodium hydroxide (2 mol) and extracted with ethyl acetate. The ethyl acetate layers were washed with sodium hydroxide (2 mol), water and brine. The combined organic layers were dried over sodium sulfate, filtered and solvent removed. A small amount of methanol added and oil was triturated to obtain the title compound (7.5 g) having the following physical data.
$^1$H NMR (400 MHz, CDCl$_3$) δ 7.84 (dt, J=8.7, 2.6, 2H), 7.28 (t, J=8.1, 1H), 7.13 (ddd, J=8.0, 1.9, 0.9, 1H), 6.99 (t, J=2.2, 1H), 6.96 (s, 1H), 6.91-6.86 (m, 1H), 3.94 (d, J=3.8, 3H).

Example 7

4-(3-chlorophenoxy)-3-methoxyaniline

Nickel chloride 6H$_2$O (3.19 g, 13.4 mmol) was dissolved in methanol (20 mL) and celite (200 mg) was added and 1.5 eq (1.52 g, 40.18 mmol) of sodium tetrahydridoborate was added slowly portion wise. The slurry was stirred for 30 minutes at room temperature. The compound (7.5 g, 26.8 mmol) prepared in Example 6 dissolved in methanol was added slowly to the slurry. After addition, sodium tetrahydridoborate (3.55 g, 93.84 mmol) was slowly added portion wise. The reaction was then stirred for an hour at room temperature. The reaction was filtered through celite and the pad was washed with methanol (50 mL). The solvent was removed and the residue was taken up in hydrochloric acid (1N) and the aqueous layer was extracted with ethyl acetate. The combine organic layers were dried over anhydrous sodium sulfate, filtered and solvent was removed to leave a reddish solid. The solid was triturate with hexane to obtain the title compound (6.03 g) having the following physical data.
TLC: Rf=0.52 (hexane:ethyl acetate=3:1);
$^1$H NMR (400 MHz, CDCl$_3$) δ 7.54 (s, 1H), 7.47 (t, J=8.1, 1H), 7.43 (d, j=1.9, 1H), 7.29 (ddd, J=8.0, 1.9, 0.9, 1H), 7.26-7.23 (m, 2H), 7.13 (t, J=2.1, 1H), 7.05 (ddd, J=8.3, 2.4, 0.9, 1H), 4.13 (d, J=36.8, 3H).

Example 8

4-bromo-1-(3-chlorophenoxy)-2-methoxybenzene

The compound (6.02 g, 24.11 mmol) prepared in Example 7 was taken up in 1:1 mixture of concentrated hydrochloric acid:water (24 mL) and cooled to 0° C. A solution of the sodium nitrite (2.16 g, 31.3 mmol) in water (6 mL) was added slowly. The ice bath was removed and the reaction was warmed to room temperature. After 45 minutes the copper bromide (10.77 g, 48.2 mmol) was added and after 5 minutes at room temperature the reaction was heated to 60° C. for 4.5 hours. The reaction was cooled to room temperature and then cooled in an ice bath. Ammonium hydroxide was added till the reaction was basic. The aqueous layer was then extracted with ethyl acetate. The combined organic layers were washed with water, brine and dried over sodium sulfate, filtered and solvent removed. The product was isolated by flash chromatography (5% ethyl acetate/hexane) to obtain the title compound (3.6 g) having the following physical data.

$^1$H NMR (400 MHz, CDCl$_3$) δ 7.19 (tdd, J=8.3, 1.9, 0.6, 1H), 7.12 (d, f=2.2, 1H), 7.07 (dd, J=8.5, 2.2, 1H), 7.03-6.97 (m, 1H), 6.90-6.84 (m, 1H), 6.81-6.77 (m, 1H), 6.63 (tt, J=4.8, 2.5, 1H), 3.86-3.69 (m, 3H).

Example 9

2-(4-(3-chlorophenoxy)-3-methoxyphenyl)-4,4,5,5-tetramethyl-1,3,2-dioxaborolane

The compound (3.6 g, 11.48 mmol) prepared in Example 8, 4,4,4',4',5,5,5',5'-octamethyl-2,2'-bi(1,3,2-dioxaborolane) (4.37 g, 17.22 mmol), potassium acetate (3.66 g, 37.3 mmol) and dichloro[1,1'-bis(diphenylphosphino) ferrocene]palladium(II) dichloromethane adduct (0.59 g, 0.72 mmol) were combined in a pressure tube and dry dioxane (25 mL) was added. The tube was flushed for 5 minutes with argon and then sealed. The reaction was heated to 80° C. for 24 hours. The reaction was cooled to room temperature and filtered through celite. The celite was washed with ethyl acetate. The ethyl acetate was evaporated with silica gel present and the product was isolated by flash chromatography (2% ethyl acetate/hexane to 10% ethyl acetate/hexane). The product after purification had the title compound (1.86 g) having the following physical data.

$^1$H NMR (400 MHz, CDCl$_3$) δ 7.41 (s, 3H), 7.39 (d, J=1.3, 1H), 7.18 (t, J=8.1, 2H), 7.02-6.93 (m, 4H), 6.88 (dd, J=4.3, 2.3, 2H), 6.84-6.79 (m, 2H), 3.85 (s, 6H), 1.34 (d, J=2.3, 26H).

Example 10

4-(3-chlorophenoxy)-3-methoxyphenylboronic acid

To a solution of the compound (179.0 mg, 0.50 mmol) prepared in Example 9 in 10 mL acetone were added sodium periodate (318.0 mg, 1.49 mmol), ammonium acetate (84.0 mg, 1.09 mmol), and water (10 mL). The suspension was allowed to stir at room temperature for 18 hours. The acetone was removed under reduced pressure and the resulting aqueous layer was acidified with concentrated hydrochloric acid to pH 3. The resulting solid was collected and washed several times with water then dried under vacuum to obtain the title compound (106 mg) having the following physical data.

$^1$H NMR (400 MHz, CDCl$_3$) δ 7.63 (s, 1H), 7.15-6.97 (m, 1H), 6.95-6.59 (m, 5H), 3.78 (s, 3H).

Example 11

6-(3-(pyrrolidin-1-yl)prop-1-ynyl)pyrrolo[2,1-f][1,2,4]triazin-4-amine

To a 20 mL pressure bottle were charged the compound (426 mg, 2.0 mmol) prepared in Example 5,1-(prop-2-ynyl)pyrrolidine (309 mg, 3 mmol), copper iodide (38 mg, 0.2 mmol), triphenylphosphine (52 mg, 0.2 mmol), potassium carbonate (276 mg, 2 mmol), and DMF (12 mL). The reaction mixture was flushed with nitrogen and dichlorobis(triphenylphosphine)palladium (Cl$_2$Pd(PPh$_3$)$_2$) (140 mg, 0.2 mmol) was added, and the reaction mixture was sealed. After heating to 60° C. for 3 days, the reaction was cooled, and DMF was removed by bulb-to-bulb distillation under reduced pressure. The crude mixture was purified by column chromatography on silica gel using a gradient of 5% methanol in dichloromethane (DCM) (1% ammonium hydroxide) to obtain the title compound (269 mg) having the following physical data.

$^1$H NMR (400 MHz, CDCl$_3$) δ 7.89 (s, 1H), 7.65 (d, J=1.6, 1H), 6.64 (d, J=1.6, 1H), 5.43 (s, 2H), 2.72-2.62 (m, 5H), 1.85-1.80 (m, 5H).

Example 12

6-(3-(pyrrolidin-1-yl)propyl)pyrrolo[2,1-f][1,2,4]triazin-4-amine

In a round-bottom flask, the compound (269 mg, 1.14 mmol) prepared in Example 11, palladium/carbon (10%, 20 mg) and methanol (10 mL) was added and the atmosphere was replaced with hydrogen gas at 1 atm. After 18 hours, the mixture was filtered through celite and the celite pad was washed with methanol. The methanol was removed in vacuo to obtain the title compound (257 mg) having the following physical data.

$^1$H NMR (400 MHz, CDCl$_3$) δ 7.84 (s, 1H), 7.43-7.37 (m, 1H), 6.42 (d, J=1.6, 1H), 5.67 (s, 2H), 2.66 (t, J=7.6, 2H), 2.48 (ddd, J=4.2, 3.7, 1.3, 6H), 1.85 (dt, J=15.3, 7.7, 2H), 1.80-1.71 (m, 5H).

Example 13

7-bromo-6-(3-(pyrrolidin-1-yl)propyl)pyrrolo[2,1-f][1,2,4]triazin-4-amine

To a solution of the compound (257 mg, 1.05 mmol) prepared in Example 12 in DMF (8 mL) at −78° C. was added 1,3-dibromo-5,5-dimethylimidazolidine-2,4-dione (150 mg, 0.52 mmol) portion wise over a period of 5 minutes. The reaction was stirred for 30 minutes and was allowed to warm to room temperature, and stirred overnight. DMF was removed under vacuum, and the crude solid was extracted with DCM/sodium hydroxide (1N) solution. The organic layer was dried, concentrated, and the crude product was purified by prep HPLC. The pure fractions were concentrated, extracted with saturated sodium bicarbonated/DCM, and the organic layer was dried sodium sulfate, filtered and concentrated to obtain the title compound (135 mg) having the following physical data.

$^1$H NMR (400 MHz, CDCl$_3$) δ 7.98 (s, 1H), 6.82 (s, 1H), 5.86 (s, 2H), 3.00 (s, 4H), 2.91-2.81 (m, 2H), 2.71 (t, J=7.0, 2H), 2.17-2.04 (m, 2H), 2.03-1.93 (m, 4H).

Example 14

7-(3-methoxyphenyl)-6-(3-(pyrrolidin-1-yl)propyl)pyrrolo[2,1-f][1,2,4]triazin-4-amine To a solution of the compound (135 mg, 0.42 mmol) prepared in Example 13, 3-methoxyphenylboronic acid (96 mg, 0.63 mmol), potassium phosphate (2N, 1 mL 2.0 mmol), tetrakis(triphenylphosphine)palladium(0) (Pd(PPh$_3$)$_4$) (11 mg, 0.01 mmol) in dioxane (3 mL) was deoxygenated by nitrogen gas for 5 minutes, and the reactor was sealed, heated at 90° C. for 20 hours. The mixture was concentrated, extracted with DCM and sodium hydroxide (1N). The organic layer was dried, concentrated, and the crude product was purified by prep TLC using 9% methanol in DCM (with 1% ammonium hydroxide) to obtain the title compound (98 mg) having the following physical data.
$^1$H NMR (400 MHz, CDCl$_3$) δ 7.88 (s, 1H), 7.44-7.33 (m, 1H), 7.16-7.08 (m, 2H), 6.92 (ddd, J=8.4, 2.6, 0.8, 1H), 6.64 (s, 1H), 5.52 (s, 2H), 3.82 (s, 3H), 2.73 (t, J=7.6, 2H), 2.49 (dd, J=15.3, 7.4, 7H), 1.88 (dt, J=15.3, 7.7, 2H), 1.82-1.72 (m, 5H).

Example 15

5-bromo-7-(3-methoxyphenyl)-6-(3-(pyrrolidin-1-yl) propyl)pyrrolo[2,1-f][1,2,4]triazin-4-amine To a solution of the compound (98 mg, 0.28 mmol) prepared in Example 14 in DMF (4 mL) at −40° C. was added 1,3-dibromo-5,5-dimethylimidazolidine-2,4-dione (40 mg, 0.14 mmol) portion wise over a period of 1 minute. The reaction was stirred for 30 minutes and was allowed to warm to room temperature, and stirred overnight. DMF was removed, and the crude solid was extracted with sodium hydroxide (1N) and DCM. The organic layer was dried, concentrated to obtain the title compound (97 mg) having the following physical data.
$^1$H NMR (400 MHz, CDCl$_3$) δ 7.80 (s, 1H), 7.41-7.33 (m, 1H), 7.10-7.01 (m, 2H), 6.94 (ddd, J=8.3, 2.6, 1.0, 1H), 6.28 (s, 1H), 3.92-3.72 (m, 3H), 2.74-2.59 (m, 2H), 2.50-2.22 (m, 6H), 1.83-1.60 (m, 6H).

Example 16

5-(4-(3-chlorophenoxy)-3-methoxyphenyl)-7-(3-methoxyphenyl)-6-(3-(pyrrolidin-1-yl)propyl)pyr-rolo[2,1-f][1,2,4]triazin-4-amine To a solution of the compound (43 mg, 0.01 mmol) prepared in Example 15, the compound (29.4 mg, 0.15 mmol) prepared in Example 10, potassium phosphate (2N, 0.1 mL, 0.2 mmol), Pd(PPh$_3$)$_4$ (3 mg, 0.003 mmol) in DMF (3 mL) was deoxygenated by nitrogen gas for 5 minutes, and the reactor was sealed, heated at 90° C. for 6 hours. The mixture was concentrated, purified by prep TLC using 5% methanol in DCM (with 3% ammonium hydroxide solution) to give crude product which was further purified by prep HPLC to obtain the title compound (2.4 mg) having the following physical data.
$^1$H NMR (400 MHz, CDCl$_3$) δ 7.87 (s, 1H), 7.40 (t, J=7.9, 1H), 7.27-7.21 (m, 2H), 7.19-7.12 (m, 2H), 7.05 (ddd, J=13.8, 8.1, 1.9, 4H), 7.00-6.93 (m, 2H), 6.88 (dd, J=8.3, 2.4, 1H), 5.15 (s, 2H), 3.84 (d, J=3.5, 6H), 2.83-2.56 (m, 2H), 2.25 (s, 6H), 1.67 (s, 7H), 1.49 (s, 2H);
(LCMS) M$^+$=584.5, RT=2.06 min.

Example 16 (1)-(5)

The compounds of the present invention having the following physical data were prepared by using the compound prepared in Example 5,1-(prop-2-ynyl)pyrrolidine or a corresponding terminal alkyne derivative instead thereof, and a corresponding boronic acid instead of the compound prepared in Example 10 in the process of Example 11→Example 12→Example 13→Example 14→Example 15→Example 16.

Example 16(1)

6-(3-(dimethylamino)propyl)-7-(3-methoxyphenyl)-5-(4-phenoxyphenyl)pyrrolo[2,1-f][1,2,4]triazin-4-amine $^1$H NMR (400 MHz, CDCl$_3$) δ 7.85 (s, 1H), 7.44-7.31 (m, 5H), 7.19-7.11 (m, 3H), 7.11-7.04 (m, 4H), 6.98-6.91 (m, 1H), 5.08 (s, 1H), 3.84 (s, 3H), 2.61 (t, J=7.9, 2H), 2.03 (d, J=13.0, 8H), 1.43 (d, J=7.1, 2H);
(LCMS) M$^+$=494.2, RT=1.84 min.

Example 16(2)

7-(3-methoxyphenyl)-5-(4-phenoxyphenyl)-6-(3-(pyrrolidin-1-yl)propyl)pyrrolo[2,1-f][1,2,4]triazin-4-amine $^1$H NMR (400 MHz, CDCl$_3$) δ 7.85 (s, 1H), 7.44-7.33 (m, 5H), 7.19-7.06 (m, 7H), 6.95 (ddd, J=8.3, 2.6, 1.0, 1H), 5.18 (s, 2H), 3.84 (s, 3H), 2.78-2.61 (m, 2H), 2.32 (s, 5H), 1.75 (s, 4H), 1.55 (s, 2H);
(LCMS) M$^+$=519.5, RT=2.11 min.

Example 16(3)

5-(4-(3,4-dichlorophenoxy)-3-methoxyphenyl)-7-(3-methoxyphenyl)-6-(3-(pyrrolidin-1-yl)propyl)pyr-rolo[2,1-f][1,2,4]triazin-4-amine

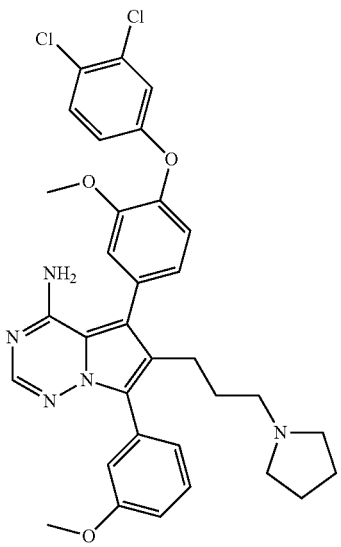 [SMILES: COc1cccc(-c2c(CCCN3CCCC3)c(-c3ccc(Oc4ccc(Cl)c(Cl)c4)c(OC)c3)c3c(N)ncnn23)c1]

$^1$H NMR (400 MHz, CDCl$_3$) δ 7.87 (s, 1H), 7.44-7.34 (m, 2H), 7.19-7.01 (m, 6H), 6.95 (dd, J=8.3, 2.6, 1H), 6.84 (dd, J=8.8, 2.8, 1H), 5.18 (s, 2H), 3.84 (d, J=1.0, 6H), 2.74-2.59 (m, 2H), 2.29-2.15 (m, 5H), 1.65 (s, 5H), 1.56-1.38 (m, 2H);
(LCMS) M$^+$=618.5, RT=2.27 min.

Example 16(4)

5-(4-(3-chlorophenoxy)phenyl)-7-(3-methoxyphenyl)-6-(morpholinomethyl)pyrrolo[2,1-f][1,2,4]tri-azin-4-amine (LCMS) M$^+$=542.3, RT=4.48 min.

Example 16(5)

5-(4-(3-chlorophenoxy)phenyl)-7-cyclopentyl-6-(morpholinomethyl)pyrrolo[2,1-f][1,2,4]triazin-4-amine (LCMS) M$^+$=504.3, RT=4.46 min.

Example 17 tert-butyl 4-(4-amino-6-(3-(pyrrolidin-1-yl)propyl)pyrrolo[2,1-f][1,2,4]triazin-7-yl)-5,6-dihydropyridine-1(2H)-carboxylate To a solution of the compound (135 mg, 0.42 mmol) prepared in Example 13, tert-butyl 4-(4,4,5,5-tetramethyl-1,3,2-dioxaborolan-2-yl)-5,6-dihydropyridine-1(2H)-carboxylate (194 mg, 0.63 mmol), potassium phosphate (2N, 1 mL, 2.0 mmol), Pd(PPh$_3$)$_4$ (11 mg, 0.01 mmol) in dioxane (3 mL) was deoxygenated by nitrogen gas for 5 minutes, and the reactor was sealed, heated at 90° C. for 20 hours. The mixture was concentrated, extracted with DCM and sodium hydroxide (1N). The organic layer was dried, concentrated, and the crude product was purified by prep TLC using 5% methanol in DCM (with 1% ammonium hydroxide) to obtain the title compound (132 mg) having the following physical data.

$^1$H NMR (400 MHz, CDCl$_3$) δ 7.84 (d, J=3.8, 1H), 6.48 (s, 1H), 5.83 (s, 1H), 5.49 (s, 1H), 4.10 (s, 2H), 3.65 (s, 2H), 2.70-2.34 (m, 10H), 1.89-1.66 (m, 6H), 1.48 (s, 9H).

Example 18 tert-butyl 4-(4-amino-6-(3-(pyrrolidin-1-yl)propyl)pyrrolo[2,1-f][1,2,4]triazin-7-yl)piperidine-1-carboxylate In a pressure reactor (50 mL), a mixture of the compound (132 mg, 0.31 mmol) prepared in Example 17 and platinum (IV) oxide in acetyl hydroxide (10 mL) was stirred under hydrogen atmosphere (3 atm). At 6 hours, the mixture was filtered through celite, eluting with acetyl hydroxide. The solvent was removed in vacuo. The resulting material extracted with DCM/sodium bicarbonate aqueous solution. The organic layers were dried over sodium sulfate, filtered and the solvent removed in vacuum to obtain the title compound (133 mg) having the following physical data.

$^1$H NMR (400 MHz, CDCl$_3$) δ 7.81 (s, 1H), 6.46 (s, 1H), 5.64 (s, 2H), 4.68 (s, 2H), 4.22 (s, 2H), 3.32 (t, J=12.5, 1H), 2.78 (s, 2H), 2.65 (t, J=7.6, 2H), 2.48 (t, J=7.5, 6H), 2.23 (dd, J=12.8, 4.1, 2H), 1.83 (dd, J=15.3, 7.8, 2H), 1.76 (s, 4H), 1.63 (d, J=12.2, 2H), 1.46 (s, 9H).

Example 19 tert-butyl 4-(4-amino-5-(4-(3,4-dichlorophenoxy)-3-methoxyphenyl)-6-(3-(pyrrolidin-1-yl)propyl)pyrrolo[2,1-f][1,2,4]triazin-7-yl)piperidine-1-carboxylate The title compound having the following physical data was prepared by reacting the product of Example 18 with 4-(3,4-dichlorophenoxy)-3-methoxyphenylboronic acid (which was prepared in Example 10) according to the process of Example 15→÷Example 16.

$^1$H NMR (400 MHz, CDCl$_3$) δ 7.83 (s, 1H), 7.36 (d, J=8.9, 1H), 7.08-6.93 (m, 4H), 6.84 (dd, J=8.8, 2.8, 1H), 5.06 (s, 1H), 4.37-4.16 (m, 1H), 3.82 (d, J=4.7, 3H), 3.29 (s, 1H), 2.82 (s, 1H), 2.57 (dd, J=44.4, 36.5, 9H), 1.79 (s, 4H), 1.67 (d, J=12.2, 4H), 1.48 (d, J=3.5, 9H).

Example 20

5-[4-(3,4-dichlorophenoxy)-3-methoxyphenyl]-7-piperidin-4-yl-6-(3-pyrrolidin-1-ylpropyl)pyrrolo[2,1-f][1,2,4]triazin-4-amine A solution of the compound (32 mg, 0.046 mmol) prepared in Example 19 in concentrated hydrochloric acid/dioxane (1 mL) was stirred at room temperature for 20 minutes. The volatiles were removed under the reduced pressure to bring the crude product to complete dryness. The product was used as is in the next reaction without further purification.

Example 21

1-(4-(4-amino-5-(4-(3,4-dichlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone To the mixture of the compound (0.045 mmol) prepared in Example 20, 2-(diethylamino)acetic acid (13 mg, 0.1 mmol) in DMF (2 mL) were added 1-hydroxybenzothiazole (HOBt) (0.5 mmol, 7 mg), 1-ethyl-3-(3-dimethylaminopropyl) carbodiimide hydrochloride (EDCI) (19 mg, 0.01 mmol) and triethanolamine (TEA) (50 µL), then the mixture was stirred overnight. The reaction was quenched by addition of water (1 mL) and the volatiles were evaporated, and the residue was extracted with DCM/sodium bicarbonate aqueous solution. The organic layer was dried, concentrated, and purified by prep HPLC followed by extraction with DCM/sodium bicarbonate aqueous solution. The organic layer was dried, concentrated to obtain the title compound (11.3 mg) having the following physical data.

$^1$H NMR (400 MHz, CD$_3$OD) δ 7.72 (s, 1H), 7.43 (d, J=8.9, 1H), 7.21 (d, J=8.0, 1H), 7.16 (d, J=1.9, 1H), 7.08-6.99 (m, 2H), 6.89 (dd, J=8.9, 2.9, 1H), 4.84 (s, 3H), 4.69 (d, J=13.0, 1H), 4.38 (d, J=12.6, 1H), 3.49 (d, J=14.2, 2H), 3.22 (dd, J=34.4, 12.5, 2H), 2.82-2.46 (m, 9H), 2.38 (dd, J=20.5, 12.7, 6H), 1.75 (s, 6H), 1.64 (d, J=7.5, 2H), 1.11 (t, J=7.1, 6H);

(LCMS) M$^+$=708.5, RT=1.91 min.

Example 21(1)

The compounds of the present invention having the following physical data were prepared by using the compound prepared in Example 5, 1-(prop-2-ynyl)pyrrolidine, tert-butyl 4-(4,4,5,5-tetramethyl-1,3,2-dioxaborolan-2-yl)-5,6-dihydropyridine-1(2H)-carboxylate instead of 3-methoxyphenylboronic acid, and the compound prepared in Example 10 in the process of Example 11→Example 12→Example 13→Example 14→Example 18→Example 19→Example 20→Example 21.

Example 21(1)

1-(4-(4-amino-5-(4-(3-chlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone $^1$H NMR (400 MHz, CD$_3$OD) δ 7.72 (s, 1H), 7.28 (t, J=8.1, 1H), 7.17 (dd, J=12.4, 5.0, 2H), 7.08-7.00 (m, 2H), 6.92-6.83 (m, 2H), 4.84 (s, 3H), 4.69 (d, J=12.6, 1H), 4.38 (d, J=13.1, 1H), 3.50 (d, J=14.2, 2H), 3.23 (dd, J=37.7, 12.5, 2H), 2.82-2.49 (m, 8H), 2.39 (dd, J=20.9, 13.2, 6H), 1.70 (d, J=49.5, 8H), 1.11 (t, J=7.2, 6H);

(LCMS) M$^+$=674.5, RT=1.76 min.

Example 22

7-cyclopentyl-5-(4-(3,4-dichlorophenoxy)-3-methoxyphenyl)-6-(2-(pyridin-3-yl)ethyl)pyrrolo[2,1-f][1,2,4]triazin-4-amine The title compound having the following physical data were prepared by using the compound prepared in Example 5, a 3-prop-2-yl-1-ylpyridine instead of a 1-(prop-2-ynyl)pyrrolidine, 2-cyclopentenyl-4,4,5,5-tetramethyl-1,3,2-dioxaborolane (194 mg) instead of 3-methoxyphenylboronic acid and using a 4-(3,4-dichlorophenoxy)-3-methoxyphenylboronic acid (64 mg) instead of the compound prepared in Example 10 in the process of Example 11→Example 13→Example 14→Example 12→Example 15→Example 16.

$^1$H NMR (400 MHz, CDCl$_3$) δ 8.37 (dd, J=4.8, 1.7, 1H), 8.14 (d, J=1.7, 1H), 7.85 (s, 1H), 7.38 (d, J=8.8, 1H), 7.19 (dt, J=7.8, 2.0, 1H), 7.10 (dd, J=7.7, 4.8, 1H), 7.03 (dd, J=9.8, 5.4, 2H), 6.89-6.75 (m, 3H), 5.03 (s, 2H), 3.78 (s, 3H), 3.44 (t, J=8.4, 1H), 2.89 (dd, J=12.7, 7.4, 2H), 2.65 (t, J=7.7, 2H), 2.21 (s, 2H), 1.97 (s, 2H), 1.82 (s, 2H), 1.70 (dd, J=15.1, 9.4, 2H);

(LCMS) M$^+$=574.5, RT=2.21 min.

Example 22 (1)-(2)

The compounds of the present invention having the following physical data were prepared by using the compound prepared in Example 5, a 3-prop-2-yl-1-ylpyridine instead of a 1-(prop-2-ynyl)pyrrolidine, 3-methoxyphenylboronic acid and a corresponding boronic acid instead of the compound prepared in Example 10 in the process of Example 11→Example 13→Example 14→Example 12→Example 15→Example 16.

Example 22(1)

7-(3-methoxyphenyl)-5-(4-phenoxyphenyl)-6-(2-(pyridin-3-yl)ethyl)pyrrolo[2,1-f][1,2,4]triazin-4-amine $^1$H NMR (400 MHz, CDCl$_3$) δ 8.33 (dd, J=4.6, 1.6, 1H), 8.02 (s, 1H), 7.84 (s, 1H), 7.39 (ddt, J=9.7, 7.6, 2.3, 3H), 7.31-7.25 (m, 2H), 7.20-7.13 (m, 1H), 7.13-7.03 (m, 8H), 7.03-6.98 (m, 1H), 6.95 (ddd, J=8.4, 2.6, 0.7, 1H), 5.27 (s, 1H), 3.83 (s, 3H), 3.05-2.81 (m, 2H), 2.48 (t, J=7.7, 2H);

(LCMS) M$^+$=5115, RT=1.99 min.

Example 22(2)

5-(4-(3,4-dichlorophenoxy)phenyl)-7-(3-methoxyphenyl)-6-(2-(pyridin-3-yl)ethyl)pyrrolo[2,1-f][1,2,4]triazin-4-amine $^1$11 NMR (400 MHz, CDCl$_3$) δ 8.33 (dd, J=4.6, 1.9, 1H), 8.00 (d, J=1.2, 1H), 7.86 (s, 1H), 7.48-7.37 (m, 2H), 7.33-7.25 (m, 2H), 7.19 (d, J=2.8, 1H), 7.13-6.91 (m, 10H), 5.11 (s, 2H), 3.84 (s, 3H), 2.92 (t, J=7.6, 2H), 2.48 (t, J=7.6, 2H);

(LCMS) M$^+$=582.5, RT=2.26 min.

Example 23 tert-butyl 4-(4-aminopyrrolo[2,1-f][1,2,4]triazin-6-yl)piperidine-1-carboxylate

By the same procedure as Example 14 and Example 18 using the compound (1.08 g) prepared in Example 5 and tert-butyl 4-(4,4,5,5-tetramethyl-1,3,2-dioxaborolan-2-yl)-5,6-dihydropyridine-1(2H)-carboxylate (1.64 g) instead of 3-methoxyphenylboronic acid, the title compound (1.02 g) having the following physical data was obtained.

(LCMS) M$^+$=317.1, RT=1.97 min

Example 24 tert-butyl 4-(4-amino-5-bromo-7-(3-methoxyphenyl)pyrrolo[2,1-f][1,2,4]triazin-6-yl)piperidine-1-carboxylate By the same procedure as Example 13, Example 14 and Example 15 using the compound (390.0 mg) prepared in Example 23 and 3-methoxyphenylboronic acid (14.72 mg) instead of the compound prepared in Example 10, the title compound (46.3 mg) having the following physical data was obtained.

(LCMS) M$^+$=504.2, RT=2.53 min.

Example 25

7-(3-methoxyphenyl)-5-(4-phenoxyphenyl)-6-(piperidin-4-yl)pyrrolo[2,1-f][1,2,4]triazin-4-amine The compound (25 mg, 0.050 mmol) prepared in Example 24, 4-phenoxyphenylboronic acid (10.65 mg, 0.050 mmol), potassium phosphate (10.56 mg, 0.050 mmol) and Pd(PPh$_3$)$_4$ (11.50 mg, 0.01 mmol) were added to a small pressure tube and DMF/water (1 mL/0.5 mL) was added. The reaction mixture was flushed with argon for 5 minutes then sealed. The reaction was heated to 100° C. for 24 hours. The DMF was removed under vacuum and the product was isolated by prep-HPLC. The product was then treated with trifluoroacetic acid (TFA) in DCM for 2 hours. The solvent (DCM/TFA) was removed under vacuum and the residue taken up in ethyl acetate/1N sodium hydroxide. The organic layer was separated and aqueous layer extracted with ethyl acetate, dried over sodium sulfate, filtered and solvent removed. Solid was dried under vacuum to obtain the title compound (8 mg) having the following physical data.

$^1$H NMR (400 MHz, CDCl$_3$) δ 7.74 (s, 1H), 7.38-7.28 (m, 5H), 7.15-6.91 (m, 8H), 3.78 (d, J=3.4, 3H), 3.06 (d, J=12.3, 1H), 2.83-2.70 (m, 1H), 2.53 (s, 2H), 1.65 (s, 3H), 1.18 (s, 3H);

(LCMS) M$^+$=492.2, RT=1.74 min.

Example 25(1)-25(14)

The compounds having the following physical data were prepared by using the compound prepared in Example 5, tert-butyl 4-(4,4,5,5-tetramethyl-1,3,2-dioxaborolan-2-yl)-5,6-dihydropyridine-1(2H)-carboxylate, or a corresponding boronic acid instead of thereof, and 4-(3-chlorophenoxy)-3-methoxyphenylboronic or a corresponding boronic acid instead thereof in the process of Example 23→Example 24→Example 25→Example 25(1)

7-cyclopentyl-5-(4-(3,4-dichlorophenoxy)-3-methoxyphenyl)-6-(piperidin-4-yl)pyrrolo[2,1-f][1,2,4]triazin-4-amine $^1$H NMR (400 MHz, CDCl$_3$) δ 7.82 (s, 1H), 7.29-7.21 (m, 1H), 6.98 (dddd, J=17.6, 15.2, 8.7, 1.5, 6H), 5.02 (s, 2H), 3.82 (s, 3H), 3.73-3.57 (m, 1H), 3.32 (d, J=12.1, 2H), 2.72 (dd, J=24.1, 11.9, 3H), 2.31 (s, 2H), 2.11 (s, 2H), 1.96 (d, J=11.6, 2H), 1.79 (t, J=15.8, 7H);

(LCMS) M$^+$=551.2, RT=2.15 min.

Example 25(2)

5-(4-(3-chlorophenoxy)-3-methoxyphenyl)-7-cyclopentyl-6-(piperidin-4-yl)pyrrolo[2,1-f][1,2,4]triazin-4-amine $^1$H NMR (400 MHz, CDCl$_3$) δ 7.82 (s, 1H), 7.29-7.21 (m, 1H), 6.98 (dddd, J=17.6, 15.2, 8.7, 1.5, 6H), 5.02 (s, 2H), 3.82 (s, 3H), 3.73-3.57 (m, 1H), 3.32 (d, J=12.1, 2H), 2.72 (dd, J=24.1, 11.9, 3H), 2.31 (s, 2H), 2.11 (s, 2H), 1.96 (d, J=11.6, 2H), 1.79 (t, J=15.8, 7H);
(LCMS) M$^+$=518.3, RT=2.14 min,

Example 25(3)

3-(4-(4-amino-7-cyclopentyl-6-(piperidin-4-yl)pyrrolo[2,1-f][1,2,4]triazin-5-yl)-2-methoxyphenoxy)benzonitrile $^1$H NMR (400 MHz, CD$_3$OD) δ 7.72 (s, 1H), 7.46-7.31 (m, 2H), 7.26-7.17 (m, 2H), 7.06 (d, J=8.0, 1H), 7.01-6.89 (m, 2H), 3.77 (s, 3H), 3.61-3.46 (m, 4H), 3.13 (d, J=12.1, 2H), 2.73 (t, J=12.2, 1H), 2.60 (t, J=11.3, 2H), 2.26 (s, 2H), 1.96 (s, 2H), 1.82 (d, J=6.1, 5H);
(LCMS) M$^+$=608.7, RT=3.39 min,

Example 25(4)

5-[4-(3,4-dichlorophenoxy)-3-methoxy-phenyl]-7-(1-methylsulfonyl-4-piperidyl)-6-(4-piperidyl)pyrrolo[2,1-f][1,2,4]triazin-4-amine $^1$H NMR (400 MHz, CD$_3$OD) δ 7.72 (s, 1H), 7.37 (d, J=8.8, 1H), 7.08-7.02 (m, 2H), 6.94 (d, J=1.9, 1H), 6.91-6.82 (m, 2H), 3.88-3.73 (m, 5H), 3.56-3.49 (m, 2H), 3.40-3.31 (m, 2H), 3.16 (t, J=11.4, 2H), 2.95-2.68 (m, 9H), 2.37-2.14 (m, 2H), 1.76 (dd, J=41.9, 12.9, 4H);
(LCMS) M$^+$=645.1, RT=2.04 min.

Example 25(5)

5-(4-(3-chlorophenoxy)-3-methoxyphenyl)-7-(1-(methylsulfonyl)piperidin-4-yl)-6-(piperidin-4-yl)pyrrolo[2,1-f][1,2,4]triazin-4-amine $^1$H NMR (400 MHz, CDCl$_3$) δ 7.78 (s, 1H), 7.25 (dd, J=8.8, 7.5, 1H), 7.08-7.02 (m, 2H), 6.97 (dd, J=4.2, 2.0, 2H), 6.93-6.87 (m, 2H), 3.99 (t, J=10.4, 2H), 3.81 (s, 3H), 3.33 (t, J=20.1, 1H), 3.09 (d, J=11.7, 2H), 2.97-2.78 (m, 8H), 2.76-2.65 (m, 1H), 2.59 (t, J=11.8, 2H), 1.72 (d, J=10.2, 4H);
(LCMS) M$^+$=611.1, RT=1.89 min.

Example 25(6)

(3-{4-amino-5-[4-(3-chlorophenoxy)-3-methoxyphenyl]-6-(4-pyridinyl)pyrrolo[2,1-f][1,2,4]triazin-7-yl}phenyl)(4-methyl-1-piperazinyl)methanone

Example 25(7)

7-cycloheptyl-5-(4-(3,4-dichlorophenoxy)-3-methoxyphenyl)-6-(piperidin-4-yl)pyrrolo[2,1-f][1,2,4]triazin-4-amine $^1$H NMR (400 MHz, CDCl$_3$) δ 7.83 (s, 1H), 7.38 (d, J=8.9, 1H), 7.09 (d, J=2.8, 1H), 7.03 (d, J=8.1, 1H), 6.98 (d, J=1.8, 1H), 6.93 (dd, J=8.1, 1.9, 1H), 6.87 (dd, J=8.8, 2.8, 1H), 3.80 (d, J=4.3, 3H), 3.40 (s, 1H), 3.20 (d, j=12.1, 2H), 2.76 (s, 1H), 2.66 (t, J=11.0, 2H), 2.35 (s, 1H), 1.93-1.48 (m, 16H);
(LCMS) M$^+$=582.3, RT=3.80 min.

Example 25(8)

5-(4-(3-chlorophenoxy)-3-methoxyphenyl)-7-cycloheptyl-6-(piperidin-4-yl)pyrrolo[2,1-f][1,2,4]triazin-4-amine $^1$H NMR (400 MHz, CDCl$_3$) δ 7.83 (s, 1H), 7.27 (d, j=8.1, 0H), 7.09-6.87 (m, 5H), 4.95 (s, 2H), 3.81 (d, J=6.0, 3H), 3.32 (d, J=12.1, 2H), 2.73 (t, J=12.5, 2H), 2.36 (s, 1H), 2.05-1.48 (m, 15H), 1.13-0.91 (m, 2H);
(LCMS) M$^+$=546.1, RT=2.18 min.

Example 25(9)

5-(4-(3,4-dichlorophenoxy)-3-methoxyphenyl)-7-(3-methoxyphenyl)-6-(piperidin-4-yl)pyrrolo[2,1-f][1,2,4]triazin-4-amine $^1$H NMR (400 MHz, CDCl$_3$) δ 7.83 (d, J=4.4, 1H), 7.42 (t, J=7.9, 1H), 7.38 (d, J=8.8, 1H), 7.10 (t, J=2.6, 1H), 7.09-7.03 (m, 4H), 7.04-6.96 (m, 2H), 6.89 (dd, J=8.8, 2.8, 1H), 3.84 (s, 7H), 3.02 (d, J=12.4, 2H), 2.92-2.68 (m, 1H), 2.50 (t, J=10.9, 2H), 1.76-1.46 (m, 4H);
(LCMS) M$^+$=590.5, RT=2.11 min.

Example 25(10)

5-[4-(3-chlorophenoxy)-3-methoxyphenyl]-7-(3-methoxyphenyl)-6-(4-piperidinyl)pyrrolo[2,1-f][1,2,4]triazin-4-amine $^1$H NMR (400 MHz, CDCl$_3$) δ 7.76 (s, 1H), 7.38 (dd, J=9.0, 7.7 Hz, 1H), 7.21 (t, J=8.5 Hz, 1H), 7.02-6.98 (m, 4H), 6.95 (dd, J=5.7, 3.8 Hz, 3H), 6.91-6.88 (m, 1H), 5.07 (s, 2H), 3.80 (s, 3H), 3.78 (s, 3H), 3.12 (d, J=11.6 Hz, 2H), 2.79 (ddd, f=11.4, 7.1, 3.4 Hz, 1H), 2.55 (t, J=12.0 Hz, 2H), 1.80-1.65 (m, 4H).

Example 25(11)

N-(4-(4-amino-5-(4-(3-chlorophenoxy)-3-methoxyphenyl)-6-(piperidin-4-yl)pyrrolo[2,1-f][1,2,4]triazin-7-yl)phenyl)-N-methylmethanesulfonamide $^1$H NMR (400 MHz, CDCl$_3$) δ 7.83 (s, 1H), 7.58-7.48 (m, 6H), 7.27 (t, J=8.1, 3H), 7.14-6.84 (m, 8H), 4.98 (s, 1H), 3.85 (s, 3H), 3.47-3.34 (m, 3H), 3.02-2.89 (m, 5H), 2.78 (t, J=−12.2, 1H), 2.48 (t, J=12.2, 2H), 1.63 (d, J=11.8, 2H);
(LCMS) M$^+$=632.2, RT=1.93 min.

Example 25(12)

5-(4-(3-chlorophenoxy)-3-methoxyphenyl)-7-(4-methoxyphenyl)-6-(piperidin-4-yl)pyrrolo[2,1-f][1,2,4]triazin-4-amine $^1$H NMR (400 MHz, CDCl$_3$) δ 7.81 (s, 1H), 7.36 (d, J=8.2, 2H), 7.12-7.01 (m, 5H), 6.99 (s, 2H), 3.87 (s, 3H), 3.86 (s, 3H), 3.36-3.17 (m, 2H), 2.93-2.80 (m, 1H), 2.63 (s, 2H), 1.88 (s, 1H), 1.78 (s, 2H);
(LCMS) M$^+$=565.2, RT=1.98 min.

Example 25(13)

N-(4-(4-amino-5-(4-(3,4-dichlorophenoxy)-3-methoxyphenyl)-6-(piperidin-4-yl)pyrrolo[2,1-f][1,2,4]triazin-7-yl)phenyl)-N-methylmethanesulfonamide ¹H NMR (400 MHz, CDCl₃) δ 7.81 (s, 1H), 7.51 (d, J=8.2, 5H), 739 (d, J=8.8, 1H), 7.13-7.00 (m, 4H), 6.89 (dd, J=8.8, 2.8, 1H), 3.84 (s, 3H), 3.46-3.32 (m, 3H), 3.05 (d, J=10.2, 2H), 2.93 (s, 4H), 2.92-2.74 (m, 5H), 2.53 (t, J=12.1, 2H), 1.78-1.46 (m, 5H);
(LCMS) M⁺=667.07, RT=2.07 min.

Example 25(14)

3-(4-(4-amino-7-(4-methoxyphenyl)-6-(piperidin-4-yl)pyrrolo[2,1-f][1,2,4]triazin-5-yl)-2-methoxyphenoxy)benzonitrile ¹H NMR (400 MHz, CD₃OD) δ 7.71 (s, 1H), 7.53 (s, 1H), 7.49 (t, J=8.0, 1H), 7.43-7.34 (m, 3H), 7.33-7.24 (m, 2H), 7.17 (d, J=8.0, 1H), 7.11 (dd, J=16.8, 1.9, 2H), 7.08-7.04 (m, 2H), 3.87 (s, 3H), 3.83 (d, J=4.1, 3H), 3.16 (d, J=10.9, 2H), 2.85 (t, J=11.9, 1H), 2.67 (t, J=12.0, 2H), 1.88-1.68 (m, 4H);
(LCMS) M⁺=546.6, RT=1.82 min.

Example 26

5-(4-(3-chlorophenoxy)-3-methoxyphenyl)-7-(1-(methylsulfonyl)piperidin-4-yl)pyrrolo[2,1-f][1,2,4]triazin-4-amine By the same procedure as Example 14, Example 15 and Example 16 in series using 7-bromopyrrolo[2,1-f][1,2,4]triazine-4-amine (1.71 mg) instead of the compound prepared in Example 5, N-methyl-N-[4-(4,4,5,5-tetramethyl-1,3,2-dioxaborolan-2-yl)phenyl]methanesulfonamide instead of 3-methoxyphenylboronic acid, and 4-(3-chlorophenoxy)-3-methoxyphenylboronic acid instead of the compound prepared in Example 10, the title compound having the following physical data was obtained.
¹H NMR (400 MHz, CDCl₃) δ 7.83-7.69 (m, 1H), 7.24 (dd, J=8.8, 7.5, 1H), 7.08-7.03 (m, 1H), 7.04 (s, 1H), 6.96 (dd, J=4.2, 2.0, 2H), 6.93-6.87 (m, 2H), 4.05-3.89 (m, 2H), 3.81 (s, 3H), 3.36 (d, J=6.5, 1H), 3.07 (t, J=15.2, 2H), 2.98-2.77 (m, 7H), 2.77-2.63 (m, 1H), 2.59 (t, J=11.8, 2H), 1.84-1.58 (m, 6H).

Example 27

6-chloro-5-(4-(3-chlorophenoxy)-3-methoxyphenyl)-7-(1-(methylsulfonyl)piperidin-4-yl)pyrrolo[2,1-f][1,2,4]triazin-4-amine The compound (15.40 mg, 0.029 mmol) prepared in Example 26 and 1,3-dichloro-5,5-dimethylimidazolidine-2,4-dione (2.87 mg, 0.015 mmol) were taken up in 2 mL of DMF and heated to 65° C. for 16 hours. The reaction was cooled to room temperature and the DMF removed under vacuum and the reaction mixture submitted for prep-HPLC purification to obtain the title compound (12.8 mg) having the following physical data.
¹H NMR (400 MHz, CDCl₃) δ 7.91 (s, 1H), 7.28 (t, J=7.9, 1H), 7.15-7.06 (m, 2H), 7.03 (s, 2H), 7.00-6.86 (m, 2H), 4.02 (d, J=11.3, 2H), 3.88 (s, 3H), 3.55 (s, 1H), 2.90-2.75 (m, 5H), 2.57 (s, 2H), 1.90 (s, 2H);
(LCMS) M⁺=562.1, RT=2.87 min.

Example 28 tert-butyl 3-(4-aminopyrrolo[2,1-f][1,2,4]triazin-7-yl)-3-hydroxypiperidine-1-carboxylate To a stirred suspension of 7-bromopyrrolo[2,1-f][1,2,4]triazin-4-amine (3.0 g, 14 mmol) in tetrahydrofuran (75 mL) was added chlorotrimethylsilane (4.5 mL, 35 mmol) dropwise. The reaction mixture was stirred at room temperature for 3 hours and a 2M solution of 2-propylmagnesium chloride in THF (37 mL, 74 mmol) was added dropwise. After 3 hours, tert-butyl 3-oxopiperidine-1-carboxylate (5.6 g, 28 mmol) was added in one portion. The mixture was stirred at room temperature overnight at which time LC/MS indicated the reaction was complete. The reaction was poured over a mixture of ice and saturated aqueous ammonium chloride (500 mL). The mixture was allowed to warm to room temperature and was extracted with ethyl acetate (250 mL) four times. The combined organic layers were washed with saturated brine, dried over sodium sulfate and concentrated under reduced pressure. The crude solid was triturated with a 2:1 mixture of ethyl acetate:heptane to obtain the title compound (2 g) having the following physical data.
¹H NMR (300 MHz, DMSO) δ7.84 (s, 1H), 7.71 (bs, 2H), 6.83 (d, J=4, 1H) 6.60 (d, J=4, 1H), 5.17 (s, 1H), 3.94-3.76 (m, 1H), 3.71-3.44 (m, 2H), 3.18-2.99 (m, 1H), 2.52-2.42 (m, 2H), 1.99-1.74 (m, 2H), 1.46-1.09 (m, 9H),
(LCMS) M⁺=334.2, RT=4.67 min.

Example 29 tert-butyl 3-(4-aminopyrrolo[2,1-f][1,2,4]triazin-7-yl)-5,6-dihydropyridine-1(2H)-carboxylate To a solution of the compound (2.0 g, 6.0 mmol,) prepared in Example 28 in pyridine (40 mL) was added trifluoroacetic anhydride (1.7 mL, 12 mmol) dropwise at 0° C. The ice bath was removed and the mixture was stirred at room temperature overnight. The reaction mixture was concentrated to dryness and the crude solid was triturated with a 2:1 mixture of heptane/ethyl acetate. The solid was filtered and washed with methanol to obtain the title compound (1.3 g) having the following physical data.
¹H NMR (300 MHz, DMSO) δ 7.88 (s, 1H), 7.75, bs, 2H), 7.00 (s, 1H), 6.91 (d, J=5, 1H), 6.65 (d, J=4, 1H), 4.30 (s, 2H), 3.49 (t, J=6, 2H), 2.35-2.26 (m, 2H), 1.43 (s, 9H);
(LCMS) M⁺=316.2, RT=5.61 min.

Example 30 tert-butyl 6-chloro-3-(4-amino-5-(4-(3-chlorophenoxy)-3-methoxyphenyl)pyrrolo[2,1-f][1,2,4]triazin-7-yl)piperidine-1-carboxylate By the same procedure as Example 18, Example 15, Example 16 and Example 27 in series using the compound (1.6 g) prepared in Example 29, and the compound (143.0 mg) prepared in Example 9 instead of the compound prepared in Example 10, the title compound (40.0 mg) having the following physical data was obtained.
¹H NMR (400 MHz, CDCl₃) δ 7.88 (s, 1H), 7.24 (dd, J=8.9, 7.4, 1H), 7.11-7.03 (m, 3H), 7.00 (dd, J=4.5, 2.2, 2H), 6.89 (dd, J=8.3, 2.4, 1H), 4.19 (s, 1H), 3.90 (s, 1H), 3.85 (s, 3H), 3.54 (s, 2H), 2.79 (s, 1H), 2.37 (s, 1H), 1.90 (d, J=13.2, 1H), 1.77 (s, 1H), 1.61 (s, 1H), 1.46 (s, 12H);
(LCMS) M⁺=584.14, RT=3.75 min.

Example 31

6-chloro-5-(4-(3-chlorophenoxy)-3-methoxyphenyl)-7-(piperidin-3-yl)pyrrolo[2,1-f][1,2,4]triazin-4-amine The compound (40 mg, 0.068 mmol) prepared in Example 30 was taken up in DCM and treated with TFA (0.5 mL). The reaction was stirred for 2 hours and monitored by TLC (1:1 ethyl acetate/hexane). The solvent was removed under vacuum and the residue was taken up in ethyl acetate and the organic layer was washed with 1N sodium hydroxide. The aqueous layer was extracted with ethyl acetate and the combined organic layers were washed with water, brine and dried over anhydrous sodium sulfate. The solution was filtered and solvent removed. The product is used in next reaction without further purification.

$^1$H NMR (400 MHz, CDCl$_3$) δ 7.90 (s, 1H), 7.28-7.21 (m, 1H), 7.11-7.03 (m, 3H), 7.01-6.96 (m, 2H), 6.89 (ddd, J=8.3, 2.4, 0.9, 1H), 3.91 (d, J=4.4, 1H), 3.85 (d, J=5.0, 3H), 3.58 (d, J=11.9, 1H), 3.50-3.36 (m, 1H), 3.11 (t, J=13.4, 2H), 2.75 (t, J=11.3, 1H), 2.42 (d, J=12.8, 1H), 2.14 (s, 2H), 1.87 (dd, J=34.7, 12.5, 2H).

Example 32

1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one

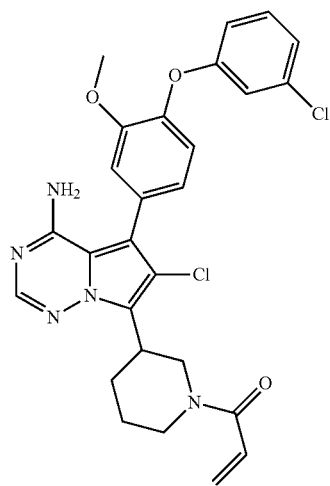 [SMILES: C=CC(=O)N1CCCC(c2c(Cl)c(-c3ccc(Oc4cccc(Cl)c4)c(OC)c3)c3c(N)ncnn23)C1]

The compound (27.6 mg, 0.057 mmol) prepared in Example 31 was taken up in 1 mL DCM (dry) under argon and triethylamine (23.8 μl, 0.171 mmole) was added. The reaction was cooled to −10° C. and the acryloyl chloride (4.17 μl, 0.051 mmole) was added via syringe slowly. The reaction quenched with methanol and solvent removed under vacuum. The title compound (10.5 mg) having the following data was isolated by prep-HPLC.

$^1$H NMR (400 MHz, CDCl$_3$) δ 7.95-7.84 (m, 1H), 6.99 (ddd, J=41.6, 20.8, 6.4, 7H), 6.71-6.50 (m, 1H), 6.40-6.18 (m, 1H), 5.78-5.56 (m, 1H), 4.95-4.47 (m, 1H), 4.21-3.93 (m, 1H), 3.86 (s, 4H), 3.71-3.33 (m, 2H), 2.58-2.36 (m, 1H), 2.04-1.85 (m, 2H), 1.75-1.57 (m, 1H);

(LCMS) M$^+$=538.04, RT=2.91 min.

Example 32(1)

The compound having the following physical data was prepared by using 7-bromopyrrolo[2,1-f][1,2,4]triazine-4-amine, tert-butyl 3-oxopiperidine-1-carboxylate and using 4-(3,4-dichlorophenoxy)-3-methoxyphenylboronic acid (187.0 mg, 1.325 mmol) instead of the compound prepared in Example 9 in the process of Example 28→Example 29→Example 30→Example 31→Example 32.

Example 32(1)

1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one

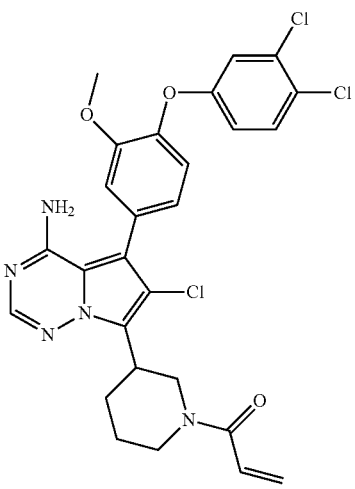 [SMILES: C=CC(=O)N1CCCC(c2c(Cl)c(-c3ccc(Oc4ccc(Cl)c(Cl)c4)c(OC)c3)c3c(N)ncnn23)C1]

$^1$H NMR (400 MHz, CDCl$_3$) δ 7.87 (d, J=20.8, 1H), 7.36 (d, J=8.8, 1H), 7.08 (dd, J=5.4, 2.7, 4H), 6.99 (dd, J=8.1, 1.9, 1H), 6.84 (dd, J=8.8, 2.8, 1H), 6.60 (d, J=10.7, 1H), 6.27 (d, J=13.0, 1H), 5.76-5.61 (m, 1H), 4.76 (s, 1H), 4.06-3.98 (m, 1H), 3.84 (s, 3H), 3.54 (d, J=32.3, 2H), 3.18 (m, 1H), 2.72 (m, 1H), 2.49 (m, 2H), 2.00-1.85 (m, 2H), 1.67 (s, 1H);

(LCMS) M$^+$=573.99, RT=3.16 min.

Example 33

5-(4-(3-chlorophenoxy)-3-methoxyphenyl)-7-cyclopentyl-6-(tetrahydro-2H-pyran-4-yl)pyrrolo[2,1-f][1,2,4]triazin-4-amine By the same procedure as Example 28, Example 29, Example 13, Example 14, Example 15 and Example 16 in series using the compound (6.39 g) prepared in Example 5, tetrahydropyran-4-one (6 g) instead of tert-butyl 3-oxopiperidine-1-carboxylate, cyclopentene pinacol boronate (298 mg) instead of 3-methoxyphenylboronic acid and the compound (200.5 mg) prepared in Example 10, the title compound (5.5 mg) having the following physical data was obtained.

$^1$H NMR (300 MHz, CDCl$_3$) δ 7.88 (s, 1H), 7.25 (m, 1H), 7.08-7.04 (m, 1H), 7.02 (d, J=8, 1H), 6.98 (t, J=2, 1H), 6.94-6.90 (m, 1H), 6.88 (d, J=2, 1H), 6.81 (dd, J=8, 2, 1H), 5.41, bs, 2H), 3.99 (dd, J=12, 4, 2H, 3.82 (s, 3H), 3.44 (t, J=11, 2H), 3.37-3.30 (m, 1H), 3.24-3.13 (m, 1H), 2.31-2.17 (m, 2H), 2.08-1.96 m, 2H), 1.72-1.54 (m, 10H);
(LCMS) M$^+$=519.3, RT=8.01 min.

Example 33(1)-33(6)

The compound having the following physical data was prepared by using the compound prepared in Example 5, a corresponding ketone derivative instead of tert-butyl 3-oxopiperidine-1-carboxylate, cyclopentene pinacol boronate instead of 3-methoxyphenylboronic acid and the compound prepared in Example 10 or the corresponding boronic acid instead thereof in the process of Example 28→Example 29→Example 18→Example 13→Example 14→Example 15→Example 16.

Example 33(1)

5-(4-(3-chlorophenoxy)-3-methoxyphenyl)-7-cyclopentyl-6-(tetrahydro-2H-thiopyran-1,1-dioxide-4-yl)pyrrolo[2,1-f][1,2,4]triazin-4-amine $^1$H NMR (300 MHz, CD$_3$OD) δ 7.79 (s, 1H), 7.28 (t, J=8.1, 1H), 7.10 (d, J=8.0, 1H), 7.05 (d, J=8.0, 1H), 6.97 (s, 1H), 6.95-6.84 (m, 3H), 3.83 (s, 3H), 3.34 (m, 3H), 3.08 (s, 6H), 2.85-2.58 (m, 2H), 2.18-1.94 (m, 4H);
(LCMS) M$^+$=567.3, RT=7.67 min.

Example 33(2)

5-(4-(4-chloro-3-(trifluoromethyl)phenoxy)-3-methoxyphenyl)-7-cyclopentyl-6-(tetrahydro-2H-pyran-4-yl)pyrrolo[2,1-f][1,2,4]triazin-4-amine $^1$H NMR (300 MHz, CDCl$_3$) δ 7.88 (s, 1H), 7.44 (d, J=8.8, 1H), 7.27 (dd, J=2.1, 1.1, 1H), 7.12-7.02 (m, 2H), 6.92-6.80 (m, 2H), 5.42 (s, 2H), 3.98 (dd, J=11.4, 4.1, 2H), 3.80 (s, 3H), 3.49-3.28 (m, 3H), 3.19 (s, 1H), 2.21 (d, 5=11.7, 2H), 2.00 (s, 2H), 1.56 (d, J=10.8, 4H);
(LCMS) M$^+$=587.1, RT=9.04 min, Example 33(3)

3-(4-(4-Amino-7-cyclopentyl-6-(tetrahydro-2H-pyran-4-yl)pyrrolo[2,1-f][1,2,4]triazin-5-yl)-2-methoxyphenoxy)benzonitrile $^1$H NMR (300 MHz, CDCl$_3$) δ 7.89 (s, 1H), 7.47-7.42 (m, 1H), 7.39-7.35 (m, 1H), 7.27-7.25 (m, 1H), 7.21-7.19 (m, 1H), 7.07 (d, J=8, 1H), 6.90-6.84 (m, 1H), 5.53 (bs, 2H), 3.99 (dd, J=8, 4, 1H), 3.80 (s, 3H), 3.44 (t, J=12, 2H), 3.37-3.31 (m, 1H), 3.21-3.16 (m, 1H), 2.32-2.19 (m, 2H), 2.06-1.97 (m, 2H) 1.74-1.67 (m, 7H), 1.57 (d, J=11, 2H);
(LCMS) M$^+$=587.1, RT=9.04 min.

Example 33(4)

7-cyclopentyl-5-[4-(3,4-dichlorophenoxy)-3-methoxyphenyl]-6-(1,1-dioxidotetrahydro-2H-thiopyran-4-yl)pyrrolo[2,1-f][1,2,4]triazin-4-amine (LCMS) M$^+$=601.2, RT=8.2 min.

Example 33(5)

3-{-4-[4-amino-7-cyclopentyl-6-(1,1-dioxidotetrahydro-2H-thiopyran-4-yl)pyrrolo[2,1-f][1,2,4]triazin-5-yl]-2-methoxyphenoxy}benzonitrile (LCMS) M$^+$=558.3, RT=6.7 min.

Example 33(6)

5-{4-[4-chloro-3-(trifluoromethyl)phenoxy]-3-methoxyphenyl}-7-cyclopentyl-6-(1,1-dioxidotetrahydro-2H-thiopyran-4-yl)pyrrolo[2,1-f][1,2,4]triazin-4-amine (LCMS) M$^+$=635.1, RT=8.5 min.

Example 34

5-(4-(3-chlorophenoxy)-3-methoxyphenyl)-7-cyclopentyl-6-(pyrrolidin-3-yl)pyrrolo[2,1-f][1,2,4]triazin-4-amine By the same procedure as Example 28, Example 29, Example 18, Example 13, Example 14, Example 15 and Example 16 in series using the compound (2.30 g) prepared in Example 5, tert-butyl 3-oxopyrrolidine-1-carboxylate (4 g) instead of tert-butyl 3-oxopiperidine-1-carboxylate, 2-cyclopentenyl-4,4,5,5-tetramethyl-1,3,2-dioxaborolane (0.4 g) and the compound (0.17 g) prepared in Example 10, the title compound (35 mg) having the following physical data was obtained.
$^1$H NMR (300 MHz, CDCl$_3$) δ 7.84 (s, 1H), 7.11-6.97 (m, 3H), 6.96-6.75 (m, 3H), 5.43 (s, 2H), 3.85 (d, J=13.8, 3H), 3.48 (dd, J=16.2, 7.8, 2H), 3.39 (s, 4H), 3.02 (t, J=10.5, 1H), 2.95-2.74 (m, 1H), 2.10 (d, J=43.8, 8H);
(LCMS) M$^+$=504.3, RT=6.67 min.

Example 35

(Z) and (E)-6-(2-ethoxyvinyl)pyrrolo[2,1-f][1,2,4]triazin-4-amine

A mixture of compound (213 mg, 1 mmol) prepared in Example 5 and (Z)-tributyl(2-ethoxyvinyl)stannane (361 mg, 1 mmol) in DMF/H$_2$O (10:1, 3 mL) was deoxygenated by passing nitrogen gas through the solution for 3 min, then palladium catalyst was added, then the reaction was sealed, heated to 100° C. overnight. The reaction was filtered through a pad of cotton, and the filtrate was concentrated, and the residue was purified by prep TLC using 8% methanol in DCM as eluent to obtain the mixture of the title compound (87 mg, Z:E=78:22) having the following physical data. The product was used for next step without further purification.
(Z): $^1$H NMR (400 MHz, CDCl$_3$) δ 1.35 (t, 3H, J=7.2 Hz), 3.98 (q, 2H, J=7.2 Hz), 5.31 (d, 1H, J=6.4 Hz), 5.80 (bs, 2H), 6.21 (d, 1H, J=6.4 Hz), 6.70 (d, 1H, J=1.6 Hz), 7.82 (d, 1H, J=1.6 Hz), 7.84 (s, 1H).
(E): $^1$H NMR (400 MHz, CDCl$_3$) δ 1.32 (t, 3H, J=7.2 Hz), 3.87 (q, 2H, J=7.2 Hz), 5.78 (d, 1H, J=12.8 Hz), 5.80 (bs, 2H), 6.46 (d, 1H, J=1.6 Hz), 6.91 (d, 1H, f=12.8 Hz), 7.47 (d, 1H, J=1.6 Hz), 7.82 (s, 1H).

Example 36

6-(2-ethoxyethyl)pyrrolo[2,1-f][1,2,4]triazin-4-amine

To a solution of the mixture of compound prepared in Example 35 in acetic acid (3 mL) was added platinum (IV)

oxide (5 mg), and the suspension was vigorously stirred under the atmosphere of hydrogen (60 psi) overnight. The reaction mixture was filtered through a pad of celite, and the filtrate was concentrated to give a crude residue which was extracted with aqueous solution sodium bicarbonate/DCM. The organic layer was separated, dried, and concentrated to obtain the title compound (55 mg) having the following data.

$^1$H NMR (400 MHz, CDCl$_3$) δ 1.20 (t, 3H, J=7.2 Hz), 1.89 (t, 2H, 6.8 Hz), 3.51 (q, 2H, J=7.2 Hz), 3.64 (t, 2H, J=6.8 Hz), 5.85 (bs, 2H), 6.50 (d, 1H, J=1.6 Hz), 7.47 (d, 1H, 1.6 Hz), 7.84 (s, 1H).

Example 37

5-(4-(3-chlorophenoxy)-3-methoxyphenyl)-7-cyclopentyl-6-(2-ethoxyethyl)pyrrolo[2,1-f][1,2,4]triazin-4-amine The compound having the following physical data was prepared by using cyclopentene pinacol boronate instead of 3-methoxyphenylboronic acid and the compound prepared in Example 10 or the corresponding boronic acid instead thereof in the process of Example 13→Example 14→Example 15→Example 16.

$^1$H NMR (400 MHz, CD$_3$OD) δ 7.71 (s, 1H), 7.53 (s, 1H), 7.49 (t, J=8.0, 1H), 7.43-7.34 (m, 3H), 7.33-7.24 (m, 2H), 7.17 (d, J=8.0, 1H), 7.11 (dd, J=16.8, 1.9, 2H), 7.08-7.04 (m, 2H), 3.87 (s, 3H), 3.83 (d, J=4.1, 3H), 3.16 (d, J=10.9, 2H), 2.85 (t, J=11.9, 1H), 2.67 (t, J=12.0, 2H), 1.88-1.68 (m, 4H); (LCMS) M$^+$=507.2, RT=3.41 min.

Example 38(1)-(6)

The compound having the following physical data was prepared by using the compound prepared in Example 5 or the corresponding pyrrolotriazine compounds instead thereof, and the compound prepared in Example 10 or the corresponding boronic acid instead thereof in the pursuant process of combination of the above described Scheme E and the above described Examples.

Example 38(1)

6-fluoro-7-(3-methoxyphenyl)-5-(4-phenoxyphenyl)pyrrolo[2,1-f][1,2,4]triazin-4-amine TLC: Rf=0.40 (hexane:ethyl actate=2:1); (LCMS) M$^+$=427.

Example 38(2)

(2E)-1-(3-{4-amino-6-chloro-5-[4-(3,4-dichlorophenoxy)-3-methoxyphenyl]pyrrolo[2,1-f][1,2,4]triazin-7-yl}-1-piperidinyl)-4-(dimethylamino)-2-buten-1-one TLC: Rf=0.46 (methyl chloride:methanol:ammonia water=80:10:1); (LCMS) M$^+$=629, RT=4.36 min.

Example 38(3)

1-(3-(4-amino-6-chloro-5-[4-(3-chlorophenoxy)-3-methoxyphenyl]pyrrolo[2,1-f][1,2,4]triazin-7-yl)-1-pyrrolidinyl)-2-propen-1-one TLC: Rf=0.62 (methyl chloride:methanol=9:1); (LCMS) M$^+$=524, RT=4.54 min.

Example 38(4)

1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one TLC: Rf=0.50 (dichloromethane:methanol:ammonia water=80:10:1); (LCMS) M$^+$=540, RT=4.55 min.

Example 38(5)

1-(3-{4-amino-6-chloro-5-[4-(3-chlorophenoxy)-3-hydroxyphenyl]pyrrolo[2,1-f][1,2,4]triazin-7-yl}-1-piperidinyl)-2-propen-1-one TLC: Rf=0.71 (dichloromethane:methanol=9:1); (LCMS) M$^+$=524.

Example 38(6)

1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one TLC: Rf=0.46 (methyl chloride:methanol=9:1); (LCMS) M$^+$=536, RT=4.63 min.

Example 39

1-[4-amino-7-cyclopentyl-5-(4-phenoxyphenyl)pyrrolo[2,1-f][1,2,4]triazin-6-yl]-1,2-ethanediol The compound having the following physical data was prepared by using the compound prepared in Example 5 and (4-phenoxyphenyl)boronic acid instead of the compound prepared in Example 10 in the pursuant process of combination of the above described Scheme B and the above described Examples.

TLC: Rf=0.29 (hexane:ethyl actate=3:2); (LCMS) M$^+$=431.

Example 40(1)-40(74)

The compound having the following physical data was prepared by using the compound prepared in Example 5 or the corresponding pyrrolotriazine compounds instead thereof, and the compound prepared in Example 10 or the corresponding boronic acid instead thereof in the pursuant process of combination of the above described Scheme A and the above described Examples.

Example 40(1)

3-{4-amino-5-[4-(3,4-dichlorophenoxy)-3-methoxyphenyl]-7-(3-methoxyphenyl)pyrrolo[2,1-f][1,2,4]triazin-6-yl}propanoic acid TLC: Rf=0.60 (ethyl actate).

Example 40(2)

{4-amino-7-cyclopentyl-5-[4-(3,4-dichlorophenoxy)-3-methoxyphenyl]pyrrolo[2,1-f][1,2,4]triazin-6-yl}acetic acid TLC: Rf=0.46 (methyl chloride:methanol=9:1).

Example 40(3)

2-{4-amino-7-cyclopentyl-5-[4-(3,4-dichlorophenoxy)-3-methoxyphenyl]pyrrolo[2,1-f][1,2,4]triazin-6-yl}ethanol TLC: Rf=0.55 (hexane:ethyl acetate=1:2);
(LCMS) M$^+$=513.

Example 40(4)

methyl 4-amino-7-(3-methoxyphenyl)-5-(4-phenoxyphenyl)pyrrolo[2,1-f][1,2,4]triazine-6-carboxylate TLC: Rf=0.59 (ethyl actate):

Example 40(5)

4-amino-7-(3-methoxyphenyl)-5-(4-phenoxyphenyl)pyrrolo[2,1-f][1,2,4]triazine-6-carboxylic acid TLC: Rf=0.38 (ethyl actate).

Example 40(6)

ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate TLC: Rf=0.29 (ethyl actate).

Example 40(7)

4-amino-7-cyclopentyl-5-(4-phenoxyphenyl)pyrrolo[2,1-f][1,2,4]triazine-6-carboxylic acid TLC: Rf=0.47 (ethyl actate:hexane=2:1).

Example 40(8)

3-{4-amino-5-[4-(3-chlorophenoxy)-3-methoxyphenyl]-7-(1-propen-2-yl)pyrrolo[2,1-f][1,2,4]triazin-6-yl}propanoic acid TLC: Rf=0.52 (ethyl actate:hexane=2:1).

Example 40(9)

(2E)-3-[4-amino-7-cyclopentyl-5-(4-phenoxyphenyl)pyrrolo[2,1-f][1,2,4]triazin-6-yl]acrylonitrile TLC: Rf=0.47 (ethyl actate:hexane=1:1).

Example 40(10)

methyl ({[4-amino-7-cyclopentyl-5-(4-phenoxyphenyl)pyrrolo[2,1-f][1,2,4]triazin-6-yl]carbonyl}amino)acetate TLC: Rf=0.57 (ethyl actate:hexane=3:2).

Example 40(11)

ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate TLC: Rf=0.31 (methyl chloride:methanol=19:1).

Example 40(12)

3-[4-amino-7-cyclopentyl-5-(4-phenoxyphenyl)pyrrolo[2,1-f][1,2,4]triazin-6-yl]-2-methylacrylic acid
TLC: Rf=0.23 (hexane:ethyl acetate=3:2).

Example 40(13)

(n)-3-{4-amino-7-cyclopentyl-5-[4-(3,4-dichlorophenoxy)-3-methoxyphenyl]pyrrolo[2,1-f][1,2,4]triazin-6-yl}acrylic acid TLC: Rf=0.21 (hexane:ethyl acetate=2:1);
(LCMS) M$^+$=539.

Example 40(14)

(2E)-3-[4-amino-7-cyclopentyl-5-(4-phenoxyphenyl)pyrrolo[2,1-f][1,2,4]triazin-6-yl]acrylamide TLC: Rf=0.61 (ethyl acetate).

Example 40(15)

(2E)-3-[4-amino-7-cyclopentyl-5-(4-phenoxyphenyl)pyrrolo[2,1-f][1,2,4]triazin-6-yl]-2-propen-1-ol TLC: Rf=0.34 (hexane:ethyl acetate=3:2).

Example 40(16)

6-(2-aminoethyl)-7-cyclopentyl-5-(4-phenoxyphenyl)pyrrolo[2,1-f][1,2,4]triazin-4-amine TLC: Rf=0.21 (hexane:ethyl acetate=1:1).

Example 40(17)

(2E)-3-[4-amino-7-cyclopentyl-5-(4-phenoxyphenyl)pyrrolo[2,1-f][1,2,4]triazin-6-yl]acrylohydrazide TLC: Rf=0.34 (ethyl acetate).

Example 40(18)

3-{4-amino-5-[4-(3,4-dichlorophenoxy)-3-methoxyphenyl]-7-(3-methoxyphenyl)pyrrolo[2,1-f][1,2,4]triazin-6-yl}propanamide TLC: Rf=0.45 (ethyl acetate);
$^1$H NMR (300 MHz, CDCl$_3$) δ 2.16 (t, J=7.96 Hz, 2H) 2.99-3.10 (m, 2H) 3.87 (s, 3H) 3.88 (s, 3H) 5.02 (brs, 2H) 5.19 (brs, 2H) 6.88 (dd, J=8.79, 2.75 Hz, 1H) 6.96-7.22 (m, 7H) 7.39 (d, J=8.79 Hz, 1H) 7.45 (t, J=7.80 Hz, 1H) 7.89 (s, 1H).

Example 40(19)

3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid TLC: Rf=0.57 (dichloro methane:methanol=9:1);

¹H NMR (300 MHz, CD₃OD) δ 1.55-1.77 (m, 1H) 1.82-2.02 (m, 2H) 2.27-2.44 (m, 2H) 2.61-2.86 (m, 2H) 2.86-2.97 (m, 2H) 3.17-4.27 (m, 6H) 4.50-4.75 (m, 1H) 5.65-5.79 (m, 1H) 6.13-6.27 (m, 1H) 6.76-6.90 (m, 2H) 6.91-6.95 (m, 1H) 6.97-7.06 (m, 2H) 7.14-7.21 (m, 2H) 7.22-7.31 (m, 1H) 7.73-7.81 (m, 1H).

Example 40(20)

3-{4-amino-5-[4-(3-chlorophenoxy)-3-methoxyphenyl]-7-cyclopentylpyrrolo[2,1-f][1,2,4]triazin-6-yl}propanoic acid TLC: Rf=0.35 (dichloro methane:methanol=19:1);
¹H NMR (300 MHz, CD₃OD) δ 1.66-1.82 (m, 2H) 1.83-2.06 (m, 4H) 2.15-2.39 (m, 4H) 2, 84-2.98 (m, 2H) 3.48-3.64 (m, 1H) 3.80 (s, 3H) 6.81-6.86 (m, 1H) 6.91-6.95 (m, 1H) 6.99-7.06 (m, 2H) 7.14-7.20 (m, 2H) 7.23-7.30 (m, 1H) 7.74 (s, 1H).

Example 40(21)

4-{4-amino-5-[4-(3-chlorophenoxy)-3-methoxyphenyl]-7-(3-methoxyphenyl)pyrrolo[2,1-f][1,2,4]triazin-6-yl}butanoic acid TLC: Rf=0.53 (methyl chloride:methanol=9:1);
(LCMS) M⁺=559, RT=4.32 min.

Example 40(22)

4-{4-amino-5-[4-(3,4-dichlorophenoxy)-3-methoxyphenyl]-7-(3-methoxyphenyl)pyrrolo[2,1-f][1,2,4]triazin-6-yl}butanoic acid TLC: Rf=0.53 (methyl chloride:methanol=9:1);
(LCMS) M⁺=593, RT=4.41 min.

Example 40(23)

3-(4-amino-5-[4-(3-chlorophenoxy)-3-methoxyphenyl]-7-{4-[(methylsulfonyl)amino]phenyl}pyrrolo[2,1-f][1,2,4]triazin-6-yl)propanoic acid TLC: Rf=0.54 (methyl chloride:methanol=9:1);
(LCMS) M⁺=608.

Example 40(24)

(2E)-3-[4-amino-7-(3-methoxyphenyl)-5-(4-phenoxyphenyl)pyrrolo[2,1-f][1,2,4]triazin-6-yl]acrylic acid TLC: Rf=0.56 (ethyl acetate);
¹H NMR (300 MHz, DMSO-d₆) δ 3.79 (s, 3H) 5.41 (d, J=16.21 Hz, 1H) 7.03-7.25 (m, 9H) 7.34-7.53 (m, 7H) 7.86 (s, 1H) 12.05-12.21 (m, 1H).

Example 40(25)

5-[4-(3,4-dichlorophenoxy)-3-methoxyphenyl]-7-(3-methoxyphenyl)-6-[2-(1H-tetrazol-5-yl)ethyl]pyrrolo[2,1-f][1,2,4]triazin-4-amine TLC: Rf=0.59 (ethyl acetate);
(LCMS) M⁺=603.

Example 40(26)

3-{4-amino-5-[4-(3-chlorophenoxy)phenyl]-7-cyclopentylpyrrolo[2,1-f][1,2,4]triazin-6-yl}propanoic acid TLC: Rf=0.40 (ethyl acetate:hexane=1:1);
(LCMS) M⁺=477, RT=4.34 min.

Example 40(27)

3-{4-amino-7-cyclopentyl-5-[4-(3,4-dichlorophenoxy)phenyl]pyrrolo[2,1-f][1,2,4]triazin-6-yl}propanoic acid TLC: Rf=0.45 (ethyl acetate:hexane=1:1);
(LCMS) M⁺=511, RT=4.42 min.

Example 40(28)

3-{4-amino-7-cyclopentyl-5-[4-(3,4-dichlorophenoxy)-3-methoxyphenyl]pyrrolo[2,1-f][1,2,4]triazin-6-yl}propanoic acid TLC: Rf=0.42 (ethyl acetate:hexane=1:1);
(LCMS) M⁺=541, RT=4.40 min.

Example 40(29)

3-(4-amino-7-cyclopentyl-5-{4-[3-(2-propanyl)phenoxy]phenyl}pyrrolo[2,1-f][1,2,4]triazin-6-yl)propanoic acid TLC: Rf=0.19 (ethyl acetate:hexane=2:3);
¹H NMR (300 MHz, CD₃OD) δ 1.24 (d, J=7.0 Hz, 6H) 1.67-1.81 (m, 2H) 1.82-2.05 (m, 4H) 2.14-2.35 (m, 4H) 2.80-2.96 (m, 3H) 3.47-3.63 (m, 1H) 6, 85-6.90 (m, 1H) 6.95-6.98 (m, 1H) 7.02-7.07 (m, 1H) 7.09 (d, J=8.6 Hz, 2H) 7.30 (t, J=7.9 Hz, 1H) 7.37 (d, J=8.6 Hz, 2H) 7.71 (s, 1H).

Example 40(30)

3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid TLC: Rf=0.40 (dichloromethane:methanol=9:1);
¹H NMR (300 MHz, CD₃OD) δ 2.29-2.40 (m, 2H) 2.41-2.55 (m, 2H) 2.91-3.02 (m, 2H) 3.82 (s, 3H) 3.84-3.94 (m, 2H) 4, 50-4.62 (m, 2H) 5.73-5.82 (m, 1H) 6.10-6.18 (m, 1H) 6.20-6.29 (m, 1H) 6.77-6.92 (m, 2H) 6.92-6.96 (m, 1H) 7.00-7.09 (m, 2H) 7.15-7.23 (m, 2H) 7.27 (t, J=82 Hz, 1H) 7.74-7.82 (m, 1H).

Example 40(31)

3-[4-amino-7-cyclopentyl-5-(4-phenoxyphenyl)pyrrolo[2,1-f][1,2,4]triazin-6-yl]propanoic acid TLC: Rf=0.33 (ethyl acetate:hexane=1:1);
$^1$H NMR (300 MHz, CD$_3$OD) δ 1.68-1.82 (m, 2H) 1.82-2.05 (m, 4H) 2.17-2.34 (m, 4H) 2.81-2.90 (m, 2H) 3.50-3.62 (m, 1H) 7.05-7.19 (m, 5H) 7.35-7.43 (m, 4H) 7.72 (s, 1H).

Example 40(32)

3-[4-amino-7-cyclopentyl-5-(3-hydroxyphenyl)pyrrolo[2,1-f][1,2,4]triazin-6-yl]propanoic acid TLC: Rf=0.74 (ethyl acetate);
(LCMS) M$^+$=367.

Example 40(33)

3-{4-amino-5-[4-(3-chlorophenoxy)-3-methoxyphenyl]-7-(3-methoxyphenyl)pyrrolo[2,1-f][1,2,4]triazin-6-yl}propanoic acid TLC: Rf=0.69 (ethyl acetate);
(LCMS) M$^+$=545.

Example 40(34)

3-{4-amino-5-[4-(3-chlorophenoxy)-3-methoxyphenyl]-7-(4-methoxyphenyl)pyrrolo[2,1-f][1,2,4]triazin-6-yl}propanoic acid TLC: Rf=0.53 (ethyl acetate:hexane=2:1);
(LCMS) M$^+$=545.

Example 40(35)

3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid TLC: Rf=0.46 (methanol:dichloromethane=1:9);
(LCMS) M$^+$=610, RT=4.30 min.

Example 40(36)

3-{4-amino-5-[4-(3-chlorophenoxy)-3-methoxyphenyl]-7-phenylpyrrolo[2,1-f][1,2,4]triazin-6-yl}propanoic acid TLC: Rf=0.60 (ethyl acetate);
(LCMS) M$^+$=515.

Example 40(37)

3-{4-amino-5-[4-(3-chlorophenoxy)-3-methoxyphenyl]-7-(2-fluorophenyl)pyrrolo[2,1-f][1,2,4]triazin-6-yl}propanoic acid TLC: Rf=0.21 (ethyl acetate:hexane=3:2);
$^1$H NMR (300 MHz, CD$_3$OD) δ 2.16-2.25 (m, 2H) 2.84-2.93 (m, 2H) 3.83 (s, 3H) 6.83-6.89 (m, 1H) 6.93-6.97 (m, 1H) 7.01-7.07 (m, 1H) 7.09-7.14 (m, 1H) 7.18-7.36 (m, 5H) 7.48-7.56 (m, 2H) 7.73 (s, 1H).

Example 40(38)

3-{4-amino-5-[4-(3-chlorophenoxy)-3-methoxyphenyl]-7-(3-fluorophenyl)pyrrolo[2,1-f][1,2,4]triazin-6-yl}propanoic acid TLC: Rf=0.21 (ethyl acetate:hexane=3:2);
$^1$H NMR (300 MHz, DMSO-d$_6$) δ 2.07-2.17 (m, 2H) 2.80-2.93 (m, 2H) 3.76 (s, 3H) 6.90-6.96 (m, 1H) 7.02-7.08 (m, 2H) 7.08-7.14 (m, 1H) 7.18-7.38 (m, 4H) 7.39-7.48 (m, 2H) 7.50-7.60 (m, 1H) 7.85 (s, 1H) 11.99 (s, 1H).

Example 40(39)

3-{4-amino-5-[4-(3-chlorophenoxy)-3-methoxyphenyl]-7-(4-fluorophenyl)pyrrolo[2,1-f][1,2,4]triazin-6-yl}propanoic acid TLC: Rf=0.21 (ethyl acetate:hexane=3:2);
$^1$H NMR (300 MHz, DMSO-d$_6$) δ 2.04-2.15 (m, 2H) 2.77-2.87 (m, 2H) 3.76 (s, 3H) 6.88-6.95 (m, 1H) 7.01-7.07 (m, 1H) 7.08-7.13 (m, 1H) 7.17-7.27 (m, 2H) 7.29-7.39 (m, 3H) 7.57-7.65 (m, 2H) 7.81 (s, 1H) 11.97 (s, 1H).

Example 40(40)

3-{4-amino-7-cyclopentyl-5-[4-(3,5-difluorophenoxy)-3-methoxyphenyl]pyrrolo[2,1-f][1,2,4]triazin-6-yl}propanoic acid TLC: Rf=0.33 (ethyl acetate:hexane=1:1);
(LCMS) M$^+$=509, RT=3.85 min.

Example 40(41)

3-{4-amino-7-cyclopentyl-5-[4-(3,5-dichlorophenoxy)-3-methoxyphenyl]pyrrolo[2,1-f][1,2,4]triazin-6-yl}propanoic acid TLC: Rf=0.33 (ethyl acetate:hexane=1:1);
(LCMS) M$^+$=541, RT=4.00 min.

Example 40(42)

3-{4-amino-7-(3-carbamoylphenyl)-5-[4-(3-chlorophenoxy)-3-methoxyphenyl]pyrrolo[2,1-f][1,2,4]triazin-6-yl}propanoic acid TLC: Rf=0.50 (ethyl acetate);
(LCMS) M$^+$=558.

Example 40(43)

3-{4-amino-7-cyclopentyl-5-[4-(3,5-difluorophenoxy)phenyl]pyrrolo[2,1-f][1,2,4]triazin-6-yl}propanoic acid TLC: Rf=0.43 (ethyl acetate:hexane=1:1);
(LCMS) M$^+$=479.

Example 40(44)

3-{4-amino-7-cyclopentyl-5-[4-(3,5-dichlorophenoxy)phenyl]pyrrolo[2,1-f][1,2,4]triazin-6-yl}propanoic acid TLC: Rf=0.45 (ethyl acetate:hexane=1:1);
(LCMS) M$^+$=511, RT=4.52 min.

Example 40(45)

(2E)-3-[4-amino-7-cyclopentyl-5-(4-phenoxyphenyl)pyrrolo[2,1-f][1,2,4]triazin-6-yl]acrylic acid TLC: Rf=0.53 (ethyl acetate:hexane=2:1);
$^1$H NMR (300 MHz, DMSO-d$_6$) δ 1.64-1.79 (m, 2H) 1.82-2.00 (m, 4H) 2.05-2.21 (m, 2H) 3.66-3.78 (m, 1H) 5.44 (d, J=15.93 Hz, 1H) 7.09-7.23 (m, 5H) 7.37-7.48 (m, 4H) 7.58 (d, J=15.93 Hz, 1H) 7.87 (s, 1H).

Example 40(46)

3-{4-amino-5-[4-(3-chlorophenoxy)-3-methoxyphenyl]-7-(2-hydroxy-2-propanyl)pyrrolo[2,1-f][1,2,4]triazin-6-yl}propanoic acid TLC: Rf=0.47 (ethyl acetate);
$^1$H NMR (300 MHz, CDCl$_3$) δ 1.79 (s, 6H) 2.40 (t, J=7.78 Hz, 2H) 2.96-3.19 (m, 2H) 3.83 (s, 3H) 4.35-5.65 (m, 3H) 6.84-7.30 (m, 7H) 7.73 (s, 1H).

Example 40(47)

({[4-amino-7-cyclopentyl-5-(4-phenoxyphenyl)pyrrolo[2,1-f][1,2,4]triazin-6-yl]carbonyl}amino)acetic acid TLC: Rf=0.42 (ethyl acetate:methanol=9:1);
$^1$H NMR (300 MHz, DMSO-d$_6$) δ 1.57-1.67 (m, 2H) 1.79-1.97 (m, 4H) 2.08-2.21 (m, 2H) 3.71-3.77 (m, 3H) 6.98-7.21 (m, 5H) 7.37-7.48 (m, 4H) 7.89-7.92 (m, 1H) 8.04-8.12 (m, 1H).

Example 40(48)

3-(4-amino-5-[4-(3-chlorophenoxy)-3-methoxyphenyl]-7-{4-[methyl(methylsulfonyl)amino]phenyl}pyrrolo[2,1-f][1,2,4]triazin-6-yl)propanoic acid TLC: Rf=0.47 (dichloromethane:methanol=9:1);
$^1$H NMR (300 MHz, CD$_3$OD) δ 2.15-2.24 (m, 2H) 2, 89-2.99 (m, 5H) 3.37 (s, 3H) 3.84 (s, 3H) 6.82-6.87 (m, 1H) 6.95-6.98 (m, 1H) 7.01-7.06 (m, 1H) 7.07-7.12 (m, 1H) 7.18 (d, J=7.9 Hz, 1H) 7.22-7.31 (m, 2H) 7.57 (d, J=8.8 Hz, 2H) 7.67 (d, J=8.8 Hz, 2H) 7.72 (s, 1H).

Example 40(49)

3-{4-amino-5-[4-(3-chlorophenoxy)-3-methoxyphenyl]-7-[4-(methylsulfonyl)phenyl]pyrrolo[2,1-f][1,2,4]triazin-6-yl}propanoic acid TLC: Rf=0.49 (dichloromethane:methanol=9:1);
$^1$H NMR (300 MHz, DMSO-d$_6$) δ 2.07-2.18 (m, 2H) 2.83-2.95 (m, 2H) 3.31 (s, 3H) 3.77 (s, 3H) 6.90-6.96 (m, 1H) 7.04-7.14 (m, 3H) 7.22 (d, j=8.1 Hz, 1H) 7.28 (d, J=2.0 Hz, 1H) 7.35 (t, J=8.2 Hz, 1H) 7.86 (s, 1H) 7.88 (d, J=8.6 Hz, 2H) 8.05 (d, J=8.6 Hz, 2H) 11.9 (s, 1H).

Example 40(50)

3-[4-amino-7-{4-[methyl(methylsulfonyl)amino]phenyl}-5-(4-phenoxyphenyl)pyrrolo[2,1-f][1,2,4]triazin-6-yl]propanoic acid TLC: Rf=0.40 (hexane:ethyl acetate=1:9);
$^1$H NMR (300 MHz, CD$_3$OD) δ 2.16-2.24 (m, 2H) 2.89-2.97 (m, 5H) 3.38 (s, 3H) 7.07-7.20 (m, 5H) 7.36-7.50 (m, 4H) 7.58 (d, J=9.0 Hz, 2H) 7.64 (d, J=9.0 Hz, 2H) 7.72 (s, 1H).

Example 40(51)

(2E)-3-[4-amino-7-(2-hydroxy-2-propanyl)-5-(4-phenoxyphenyl)pyrrolo[2,1-f][1,2,4]triazin-6-yl]acrylic acid TLC: Rf=0.33 (hexane:ethyl acetate=1:2);
$^1$H NMR (300 MHz, DMSO-d$_6$) δ 1.72 (s, 6H) 5.10 (d, J=16.48 Hz, 1H) 5.60 (s, 1H) 7.02-7.48 (m, 11H) 7.87 (s, 1H) 8.54 (d, J=16.48 Hz, 1H) 11.81-11.97 (m, 1H)

Example 40(52)

3-(4-amino-7-cyclopentyl-5-{3-methoxy-4-[3-(2-propanyl)phenoxy]phenyl}pyrrolo[2,1-f][1,2,4]triazin-6-yl)propanoic acid TLC: Rf=0.43 (hexane:ethyl acetate=1:1);
(LCMS) M$^+$=515, RT=4.40 min.

Example 40(53)

(2E)-3-[7-(1-acryloyl-3-methoxy-3-azetidinyl)-4-amino-5-(4-phenoxyphenyl)pyrrolo[2,1-f][1,2,4]triazin-6-yl]acrylic acid TLC: Rf=0.38 (chloroform:methanol=9:1);
(LCMS) M$^+$=512, RT=4.24 min.

Example 40(54)

(2E)-3-{4-amino-7-[1-(methylsulfonyl)-4-piperidinyl]-5-(4-phenoxyphenyl)pyrrolo[2,1-f][1,2,4]triazin-6-yl}acrylic acid TLC: Rf=0.23 (hexane:ethyl acetate=3:7);
$^1$H NMR (300 MHz, DMSO-d$_6$) δ 1.70-1.83 (m, 2H) 2.40-2.62 (m, 2H) 2.82-2.97 (m, 5H) 3.23-3.51 (m, 1H) 3.63-3.74 (m, 2H) 5.45 (d, J=16.1 Hz, 1H) 7.10-7.22 (m, 5H) 7.37-7.46 (m, 4H) 7.60 (d, J=16.1 Hz, 1H) 7.90 (s, 1H) 12.21 (s, 1H).

Example 40(55)

(2E)-3-[4-amino-7-cyclopentyl-5-(2-fluoro-4-phenoxyphenyl)pyrrolo[2,1-f][1,2,4]triazin-6-yl]acrylic acid TLC: Rf=0.37 (hexane:ethyl acetate=1:1);
$^1$H NMR (300 MHz, DMSO-d$_6$) δ 1.62-1.81 (m, 2H) 1.81-2.02 (m, 4H) 2.01-2.21 (m, 2H) 3.64-3.78 (m, 1H) 5.40 (d, J=16.3 Hz, 1H) 6.93 (dd, J=8.3, 2.5 Hz, 1H) 7.06 (dd, J=10.8, 2.5 Hz, 1H) 7.17-7.25 (m, 3H) 7.39-7.48 (m, 3H) 7.59 (d, J=16.3 Hz, 1H) 7.90 (s, 1H) 12.20 (s, 1H).

Example 40(56)

3-[4-amino-7-(3-methoxyphenyl)-5-(4-phenoxyphenyl)pyrrolo[2,1-f][1,2,4]triazin-6-yl]propanoic acid TLC: Rf=0.40 (hexane:ethyl acetate=1:2);
$^1$H NMR (300 MHz, CD$_3$OD) δ 2.14-2.23 (m, 2H) 2.86-2.95 (m, 2H) 3.84 (s, 3H) 6.96-7.20 (m, 8H) 7.35-7.49 (m, 5H) 7.71 (s, 1H).

Example 40(57)

(2E)-3-[4-amino-7-cyclohexyl-5-(4-phenoxyphenyl)pyrrolo[2,1-f][1,2,4]triazin-6-yl]acrylic acid TLC: Rf=0.27 (hexane:ethyl acetate=3:2);
1H NMR (300 MHz, DMSO-d$_6$) δ 1.26-1.48 (m, 3H) 1.64-1.91 (m, 5H) 2.07-2.27 (m, 2H) 3.25-3.39 (m, 1H) 5.39 (d, J=16.1 Hz, 1H) 7.09-7.21 (m, 5H) 7.37-7.46 (m, 4H) 7.63 (d, J=16.1 Hz, 1H) 7.88 (s, 1H) 12.17 (s, 1H).

Example 40(58)

(2E)-3-[4-amino-7-(1,1-dioxidotetrahydro-2H-thiopyran-4-yl)-5-(4-phenoxyphenyl)pyrrolo[2,1-f][1,2,4]triazin-6-yl]acrylic acid TLC: Rf=0.20 (hexane:ethyl acetate=3:7);
$^1$H NMR (300 MHz, DMSO-d$_6$) δ 1.90-2.08 (m, 2H) 2.91-3.15 (m, 4H) 3.38-3.54 (m, 2H) 3.67-3.83 (m, 1H) 5.49 (d, J=16.1 Hz, 1H) 7.10-7.22 (m, 5H) 7.36-7.47 (m, 4H) 7.61 (d, J=16.1 Hz, 1H) 7.92 (s, 1H) 12.17 (s, 1H).

Example 40(59)

(2E)-3-(4-amino-7-cyclopentyl-5-{4-[3-(2-propanyl)phenoxy]phenyl}pyrrolo[2,1-f][1,2,4]triazin-6-yl)acrylic acid TLC: Rf=0.32 (hexane:ethyl acetate=2:1);
(LCMS) M$^+$=483.

Example 40(60)

(2E)-3-{4-amino-5-[4-(3-chlorophenoxy)-3-methoxyphenyl]-7-cyclopentylpyrrolo[2,1-f][1,2,4]triazin-6-yl}acrylic acid TLC: Rf=0.18 (hexane:ethyl acetate=2:1);
(LCMS) M$^+$=505.

Example 40(61)

(2E)-3-[4-amino-5-(4-phenoxyphenyl)-7-(tetrahydro-2H-pyran-4-yl)pyrrolo[2,1-f][1,2,4]triazin-6-yl]acrylic acid TLC: Rf=0.20 (hexane:ethyl acetate=2:3);
$^1$H NMR (300 MHz, DMSO-d$_6$) δ 1.50-1.63 (m, 2H) 3.22-3.39 (m, 2) 3.41-3.67 (m, 3H) 3.92-4.03 (m, 2H) 5.42 (d, J=16.1 Hz, 1H) 7.09-7.21 (m, 5H) 736-7.47 (m, 4H) 7.64 (d, J=16.1 Hz, 1H) 7.90 (s, 1H) 12.20 (s, 1H).

Example 40(62)

(2E)-3-[4-amino-7-(3-hydroxy-3-methylbutyl)-5-(4-phenoxyphenyl)pyrrolo[2,1-f][1,2,4]triazin-6-yl]acrylic acid TLC: Rf=0.25 (ethyl acetate:methanol=19:1);
$^1$H NMR (300 MHz, DMSO-d$_6$) δ 1.19 (s, 6H) 1.59-1.69 (m, 2H) 3.03-3.20 (m, 2H) 4.42 (s, 1H) 5.82 (d, J=16.3 Hz, 1H) 7.05-7.25 (m, 5H) 7.32-7.51 (m, 5H) 7.92 (s, 1H) 12.13 (s, 1H).

Example 40(63)

(2E)-3-[4-amino-7-isopropyl-5-(4-phenoxyphenyl)pyrrolo[2,1-f][1,2,4]triazin-6-yl]acrylic acid TLC: Rf=0.26 (hexane:ethyl acetate=1:1);
$^1$H NMR (300 MHz, DMSO-d$_6$) δ 1.45 (d, J=7.1 Hz, 6H) 3.63-3.75 (m, 1H) 5.44 (d, J=16.1 Hz, 1H) 7.09-7.23 (m, 5H) 7.37-7.47 (m, 4H) 7.59 (d, J=16.1 Hz, 1H) 7.88 (s, 1H) 12.17 (s, 1H).

Example 40(64)

N-{2-[4-amino-7-cyclopentyl-5-(4-phenoxyphenyl)pyrrolo[2,1-f][1,2,4]triazin-6-yl]ethyl}acetamide TLC: Rf=0.21 (hexane:ethyl acetate=1:1);
(LCMS) M$^+$=456.

Example 40(65)

4-[4-amino-7-cyclopentyl-5-(4-phenoxyphenyl)pyrrolo[2,1-f][1,2,4]triazin-6-yl]-1-hydroxy-2-butanone TLC: Rf=0.44 (hexane:ethyl acetate=1:2);
(LCMS) M$^+$=457.

Example 40(66)

4-amino-7-cyclopentyl-N-(2-hydroxyethyl)-5-(4-phenoxyphenyl)pyrrolo[2,1-f][1,2,4]triazine-6-carboxamide TLC: Rf=0.53 (ethyl acetate);
(LCMS) M$^+$=458.

Example 40(67)

4-amino-7-cyclopentyl-5-(4-phenoxyphenyl)-N-(1H-pyrazol-4-yl)pyrrolo[2,1-f][1,2,4]triazine-6-carboxamide TLC: Rf=0.50 (ethyl acetate);
(LCMS) M$^+$=480.

Example 40(68)

4-amino-7-cyclopentyl-5-(4-phenoxyphenyl)-N-(1H-pyrazol-3-yl)pyrrolo[2,1-f][1,2,4]triazine-6-carboxamide TLC: Rf=0.48 (ethyl acetate);
(LCMS) M$^+$=480.

Example 40(69)

(2E)-3-[4-amino-7-cyclopentyl-5-(4-phenoxyphenyl)
pyrrolo[2,1-f][1,2,4]triazin-6-yl]acrylamide TLC: Rf=0.61 (ethyl acetate);
(LCMS) M$^+$=440.

Example 40(70)

4-amino-7-cyclopentyl-N-(2-methoxyethyl)-5-(4-
phenoxyphenyl)pyrrolo[2,1-f][1,2,4]triazine-6-carboxamide TLC: Rf=0.53 (ethyl acetate);
(LCMS) M$^+$=472.

Example 40(71)

4-amino-7-cyclopentyl-5-(4-phenoxyphenyl)pyrrolo
[2,1-f][1,2,4]triazine-6-carbohydrazide TLC: Rf=0.45 (ethyl acetate);
(LCMS) M$^+$=429.

Example 40(72)

4-amino-7-cyclopentyl-N-[2-(dimethylamino)ethyl]-
5-(4-phenoxyphenyl)pyrrolo[2,1-f][1,2,4]triazine-6-
carboxamide TLC: Rf=0.49 (ethyl acetate:methanol:triethylamine=17:2:1);
(LCMS) M$^+$=485.

Example 40(73)

(2E)-3-[4-amino-7-cyclopentyl-5-(4-phenoxyphenyl)
pyrrolo[2,1-f][1,2,4]triazin-6-yl]-N-(1H-pyrazol-4-yl)acrylamide TLC: Rf=0.73 (ethyl acetate);
(LCMS) M$^+$=506.

Example 40(74)

4-amino-7-cyclopentyl-5-(4-phenoxyphenyl)pyrrolo
[2,1-f][1,2,4]triazine-6-carboxamide TLC: Rf=0.62 (ethyl acetate);
(LCMS) M$^+$=414.

BIOLOGICAL EXAMPLES

It was proved by the following experiments that the compound of the present invention has selective Btk inhibitory activity. The methods for experiments are shown below, but they are not limited thereto.

Biological Example 1

Btk In Vitro Inhibitory Activity and Selectivity for Btk

Btk tyrosine phosphorylation reaction was carried out using Z'-lyte kinase assay kit—Tyr 1 peptide (Invitrogen) consisting of the following reagent (Tyr 1 peptide, Thy 1 phospho-peptide, 5× kinase buffer, ATP, development regent B, development buffer, and stop reagent) and Btk. Btk activity was determined using fluorescence resonance energy transfer (FRET) method.

The diluted solution (5 µl) of the compound of the present invention in dimethyl sulfoxide (DMSO; Sigma) was added to 96-well assay plates. Additionally, the peptide/kinase solution (10 µl) composed of DL-Dithiothreitol (DTT; 2 mM), Tyr 1 peptide (2 µM), kinase buffer and Btk (5 nM, Invitrogen) was added to the assay plates and the reaction solution was pre-incubated for 20 minutes at 25° C. Then, the ATP solution (5 µl) composed of adenosine triphosphate (ATP; 36 µM) and kinase buffer was added and the reaction solution was incubated for 1 hour at 25° C. After the incubation, the development solution B (10 µl) composed of development reagent B and development buffer was added and the reaction solution was incubated for 1 hour at 25° C. The stop solution (10 µl) was added to each well to arrest the enzyme reaction. The fluorescence emission of each well was measured on a fluorescence plate reader at a wavelength of 445 nm and 520 nm. The phospholyration ratio was determined by the emission rate of the fluorescence at 445 nm to 520 nm according to manufacturer's instruction.

The inhibition rate (%) of the compounds of the present invention was calculated with the following formula:

$$\text{Inhibition rate}(\%)=1-\{(A_X-A_B)/(A_C-A_B)\}\times 100$$

$A_X$: phospholyration ratio at addition of the compound of the present invention
$A_B$: phospholyration ratio at blank
$A_C$: phospholyration ratio at only addition of DMSO The value of 50% inhibition rate (IC50) for the compound of the present invention was determined from inhibition curve based on inhibition rate at each concentration of the compound of the present invention.

Research for inhibitory activity to other kinases (such as Lck, Fyn, LynA) was performed in similar procedure above described.

Biological Example 2

Btk In Vitro Radioassay

The diluted solution (1 µl) of the compound of the present invention in DMSO was added to 96-well assay plates. Additionally, Btk kinase solution (39 µL) composed of Btk (1.3 nM, Invitrogen), Tris (12.5 mM; pH7.5), Triton X-100 (0.01%), glycerol (5%), MgCl$_2$ (10 mM), EGTA (1 mM), glycerol 2-phosphate (5 mM), DTT (2 mM) and sodium orthovanadate (0.5 mM) was added to 96-well assay plate. The solution was pre-incubated for 20 minutes at 30° C. Then ATP/peptide solution (10 µL) composed of Poly (Glu, Tyr) (0.20 mg/mL, Sigma) and $^{33}$P-ATP (47 µM, PerkinElmer) was added. After incubating at 30° C. for 12 minutes, the reaction was stopped by adding 10 µL of 0.6M phosphoric acid to each well. The each reaction from the 96-well assay plate was transferred to 96-well filter plate. The reaction mixture was analyzed on the radioactive survey equipment (TopCount NXT HTS; PerkinElmer) to read count efficiency.

The inhibition rate (%) of the compound of the present invention was calculated with the following formula:

$$\text{Inhibition rate}(\%)=\{1-(\text{counts}-B_{100})/(B_0-B_{100})\}\times 100$$

$B_0$: average counts for 0% inhibition control (i.e., no compound)
$B_{100}$: average counts for 100% inhibition control (i.e., no enzyme)

The value of 50% inhibition rate (IC50) for the compounds of the present invention was determined from inhibition curve based on inhibition rate at each concentration of the compound of the present invention.

As a result, IC50 of Btk inhibition for most of the compounds of the present invention showed below 10 μM. For example, IC50 over Btk of the compound prepared in Example 16(1), 16(2), 16(3), 21, 21(1), 25(1), 32 and 32(1) showed 0.0058 μM, 0.065 μM, 0.012 μM, 0.016 μM, 0.022 μM, 0.062 μM, 0.002 μM and 0.002 μM, respectively.

As a result of Biological Example 1 and 2, the compounds of the present invention possess the potent (preferably more than 10 times) selectivity of Btk inhibitory activity over the other various kinases, especially Lck, additionally, LynA, and Fyn shown below table 1.

TABLE 1

| Example No. | Lck[IC50]/Btk[IC50] | LynA[IC50]/Btk[IC50] | Fyn[IC50]/Btk[IC50] |
|---|---|---|---|
| 16(3) | 40 | 78 | 917 |
| 32 | 161 | 1389 | 7222 |
| 32(1) | 1750 | 10000 | >10000 |

Biological Example 3

B Cell Activation Assay Using Mouse Splenocytes

Splenocytes collected from C57B1/6 or Balb/c mice were suspended in RPMI 1640 (Invitrogen), supplemented with 10% fetal bovine serum (FBS). The diluted solution (1 μl) of the compound of the present invention and the suspension of the mouse splenocytes (49 μl) were added to 96-well plate and incubated at 37° C. for 60 min. Cells were stimulated with 10 μl of anti-mouse IgM (Jackson Immunoresearch). Samples were stimulated at 37° C. for 6 hours, 5% $CO_2$ and treated with 10 μl/well Fc block (BD Biosciences) for 15 min on ice in the dark. The diluted solution (10 μl) of antibody (1:2:2 mix of each, Allphycocyanin (APC)-labeled anti-mouse CD3e, Phycoerythrin (PE)-labeled anti-mouse CD19 and Fluorescein Isothiocyanate (FITC) labeled anti-mouse CD69) was added to 96-well collection plate. Samples were transferred to the 96-well collection plate and incubated for 30 min on ice in the dark. Samples were treated with Lyse/Fix solution (1.6 ml/well, BD biosciences) at 37° C. in collection plates and were incubated for at 37° C. for 15 min. Cells were collected by centrifugation at 2000 rpm for 10 min repeatedly, resuspended in stain buffer (BD Biosciences) and analyzed by FACS to determine mean fluorescence intensity (MFI) of CD69 in the CD19 positive cell population. The inhibition rate (%) of the compound of the present invention was calculated with the following formula:

Inhibition rate(%)={1−(MFI−$C_{100}$)/($C_0$−$C_{100}$)}×100

$C_0$: MFI of 0% inhibition control (i.e., no compound)
$C_{100}$: MFI of 100% inhibition control (i.e., no stimulation)

The value of 50% inhibition rate (IC50) for the compounds of the present invention was determined from inhibition curve based on inhibition rate at each concentration of the compound of the present invention.

As a result, the compounds of the present invention showed potent inhibitory activity for activation of B cell. For example, IC50 of the compound prepared in Example 32 showed 0.13 μM.

Biological Example 4

Pharmacokinetic Profile

Using fasted male Sprague-Dawley rats (250-400 gram; Hilltop Labs), the plasma concentration of the compound of the present invention after intravenous administration at a dose of 1 mg/kg and the plasma concentration after oral gavage administration at a dose of 2 mg/kg were measured. The blood samples (~0.25 mL) was collected from a rat jugular vein under an unanesthetized condition 1, 5, 15, and 30 minutes, and 1, 2, 4, 8, 12 and 24 hours after intravenous administration, and 5, 15 and 30 minutes, and 1, 1.5, 2, 4, 8, 12 and 24 hours after oral administration. Then the blood samples placed into chilled tubes containing sodium heparin and kept on ice until centrifugation. The samples were centrifuged at a temperature of 4° C. at 13,000 rpm for 5 minutes and the supernatant was collected as plasma. The concentration of the compound in plasma was measured with LC/MS/MS (Acquity HPLC coupled with a quattromicro mass spectrometer, Waters Corp.). From the obtained plasma concentration, an area under the curve (AUC, ng·h/ml), a maximum plasma concentration.(Cmax, μg/mL) and a clearance (CL, mL/hr/kg) were calculated. In addition, Bioavailability (B.A.) of the compound of the present invention was calculated from AUC in oral administration and AUC in intravenous administration.

As a result of examination for pharmacokinetics profile of the compound of the present invention, for example, the compound of the present invention prepared in Example 32 showed a superior pharmacokinetics profile (e.g., Cmax: 0.227 μg/mL, AUC: 652 ng·h/ml, CL: 0.74 mL/hr/kg, B.A.: 24%).

Formulation Example 1

The following components are admixed in conventional method and punched out to obtain 10,000 tablets each containing 10 mg of active ingredient.

| | |
|---|---|
| 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine | 100 g |
| carboxymethylcellulose calcium (disintegrating agent) | 20 g |
| magnesium stearate (lubricating agent) | 10 g |
| microcrystalline cellulose | 870 g |

Formulation Example 2

The following components are admixed in conventional method. The solution is sterilized in conventional manner, filtered through dust removal equipment, placed 5 ml portions into ampoules and sterilized by autoclave to obtain 10,000 ampoules each containing 20 mg of the active ingredient.

| | |
|---|---|
| 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine | 200 g |
| mannitol | 20 g |
| distilled water | 50 L |

INDUSTRIAL APPLICABILITY

Since the compound represented by the formula (I), a salt thereof, a solvate thereof, an N-oxide thereof or a prodrug thereof, has a Btk inhibitory activity, and is furthermore safe, it could be useful as a preventive and/or therapeutic agent for, for example, a rheumatoid arthritis of autoimmune disease, a B cell lymphoma of cancer, and the like

The invention claimed is:
1. A compound represented by formula (I)

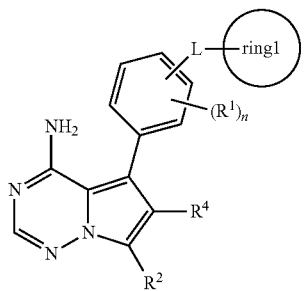

wherein ring1 represents benzene which is optionally substituted with 1-5 substituent(s) selected from the group consisting of halogen, a C1-4 alkyl, $CF_3$, nitrile, $CONH_2$, and $OR^{5-103}$;

$R^1$ represents halogen or a C1-4 alkoxy;

L represents —O— or —S—;

$R^2$ represents (1) a C1-4 alkyl substituted with $OR^{5-103}$, (2) C2-4 alkenyl, or (3) ring2 optionally substituted with one or more —K—$R^3$;

ring2 represents (1) a C4-7 carbocyclic ring or (2) a 4-7 membered heterocyclic ring, any atom of which is optionally substituted with one or more oxo group;

K represents bond, a C1-4 alkylene, —C(O)$CH_2$—, —C(O)$CH_2CH_2$—, —C(O)O—, —$CH_2$C(O)—, —$CH_2$C(O)O—, —C(O)—, —$CH_2$O—, —$CH_2CH_2$O—, —O—, —$OCH_2$—, —$OCH_2$C(O)— or —$SO_2$—, wherein the left bond binds to ring2;

$R^3$ represents (1) hydrogen, (2) $NR^{3-101}R^{3-102}$, (3) a C1-4 alkyl optionally substituted with $NR^{3-101}R^{3-102}$, (4) a C2-4 alkenyl optionally substituted with $NR^{3-101}R^{3-102}$, (5) $CF_3$, (6) nitrile, (7) halogen, or (8) a cyclic ring optionally substituted with 1-5 substituent(s) selected from the group consisting of halogen, a C1-4 alkyl, a C1-4 alkoxy, $CF_3$, nitrile and oxo, wherein the cyclic ring is selected from the group consisting of morpholine, pyrrolidine, benzene, piperazine, tetrahydropyran, piperidine, tetrahydrofuran, oxazole, thiazole, pyrazole and oxadiazole;

$R^4$ represents (1) halogen, (2) $CONR^{4-101}R^{4-102}$, (3) $CO_2R^{4-103}$, (4) ring3, (5) a C1-4 alkyl which is substituted with 1-5 substituent(s) selected from ring4, nitrile, $NR^{4-101}R^{4-102}$, $CONR^{4-101}R^{4-102}$, $COR^{4-103}$, $COR^{4-103}$, $OR^{4-103}$, $SOR^{4-103}$, and $SO_2R^{4-103}$, or (6) a C2-4 alkenyl which is substituted with 1-5 substituent(s) selected from ring4, nitrile, $NR^{4-101}R^{4-102}$, $CONR^{4-101}R^{4-102}$, $CO_2R^{4-103}$, $COR^{4-103}$, $OR^{4-103}$, $SOR^{4-103}$ and $SO_2R^{4-103}$;

$R^{3-101}$ and $R^{3-102}$ each independently represent (1) hydrogen, (2) a C1-4 alkyl, (3) $COR^{3-103}$, (4) $CONR^{3-103}R^{3-104}$ or (5) $SO_2R^{3-103}$, wherein $R^{3-103}$ and $R^{3-104}$ each independently represent a C1-4 alkyl;

$R^{4-101}$, $R^{4-102}$ and $R^{4-103}$ each independently represent (1) hydrogen, (2) $COR^{5-103}$, (3) $NR^{5-101}R^{5-102}$, (4) ring5, or (6) a C1-4 alkyl optionally substituted with $CO_2R^{5-103}$, $OR^{5-103}$, or $NR^{5-101}R^{5-102}$;

$R^{5-101}$, $R^{5-102}$ and $R^{5-103}$ each independently represent hydrogen or a C1-4 alkyl;

ring3, ring4 and ring5 each independently represent a 4-7 membered heterocyclic ring optionally substituted with 1-5 substituent(s) selected from the group consisting of halogen, oxo, a C1-4 alkyl, a C1-4 alkoxy, $CF_3$, $CONR^{5-101}R^{5-102}$, $CO_2R^{5-103}$, $SOR^{5-103}$, $SO_2R^{5-103}$ and nitrile;

n represents 0 or 1;

a salt thereof or a solvate thereof.

2. The compound according to claim 1, wherein the ring2 is selected from the group consisting of cyclopentane, cyclohexane, cycloheptane, benzene, azetidine, pyrrolidine, tetrahydropyridine, piperidine, perhydroazepine, morpholine, piperazine, pyran, thiopyran, pyridine, pyrazole, isoindoline and perhydroisoquinoline.

3. The compound according to claim 1, wherein halogen in $R^4$ is chlorine;

ring3 in $R^4$ is selected from the group consisting of pyrrolidine, piperidine, morpholine, tetrahydrothiopyran and pyridine; or ring4 in $R^4$ is selected from the group consisting of pyrrolidine, piperidine, morpholine, imidazole, tetrazole and pyridine.

4. The compound according to claim 3, wherein $R^4$ is (1) chlorine, (2) piperidine, (3) tetrahydrothiopyran, (4) pyrrolidine, (5) morpholine, (6) a C1-4 alkyl which is substituted with substituent(s) selected from the group consisting of $NR^{4-101}R^{4-102}$, $CO_2R^{4-103}$, $OR^{4-103}$, pyrrolidine, morpholine and pyridine, or (7) a C2-4 alkenyl which is substituted with substituent(s) selected from the group consisting of $NR^{4-101}R^{4-102}$, $CO_2R^{4-103}$, $OR^{4-103}$, pyrrolidine, morpholine and pyridine, wherein all the symbols have the same meanings as described in claim 1.

5. The compound according to claim 1, which is a compound represented by formula (I-1)

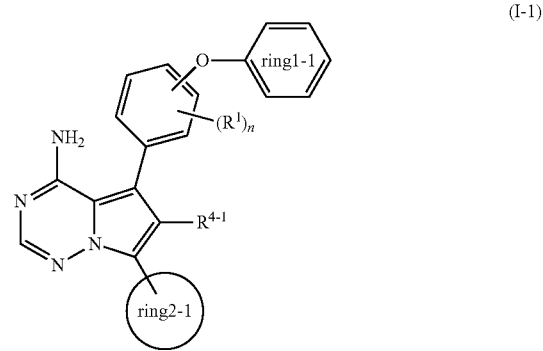

wherein ring1-1 represents benzene which may be optionally substituted with 1-5 substituent(s) selected from the group consisting of halogen, a C1-4 alkyl, $CF_3$, and nitrile;

ring2-1 represents cyclopentane, cycloheptane, benzene, azetidine, tetrahydropyridine, or piperidine optionally substituted with K—$R^3$, $R^{4-1}$ represents (1) chlorine, (2) piperidine, (3) tetrahydrothiopyran, (4) pyrrolidine, (5) morpholine (6) a C1-4 alkyl which is substituted with 1-5 substituent(s) selected from the group consisting of $NR^{4-101}R^{4-102}$, $CO_2R^{4-103}$, $OR^{4-103}$, pyrrolidine, morpholine and pyridine, or (7) a C2-4 alkenyl which is substituted with 1-5 substituent(s) selected from the group consisting of $NR^{4-101}R^{4-102}$, $CO_2R^{4-103}$, $OR^{4-103}$, pyrrolidine, morpholine and pyridine;

the other symbols have the same meanings as claim 1.

6. The compound according to claim 1, which is
(1) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 6-(3-(dimethylamino)propyl)-7-(3-methoxyphenyl)-5-(4-phenoxyphenyl)pyrrolo[2,1-f][1,2,4]triazin-4-amine,
(3) 7-(3-methoxyphenyl)-5-(4-phenoxyphenyl)-6-(3-(pyrrolidin-1-yl)propyl)pyrrolo[2,1-f][1,2,4]triazin-4-amine,
(4) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(5) 5-[4-(3-chlorophenoxy)phenyl]-7-(3-methoxyphenyl)-6-(4-morpholinylmethyl)pyrrolo[2,1-f][1,2,4]triazin-4-amine,
(6) 5-[4-(3-chlorophenoxy)phenyl]-7-cyclopentyl-6-(4-morpholinylmethyl)pyrrolo[2,1-7f][1,2,4]triazin-4-amine,
(7) 1-(4-(4-amino-5-(4-(3,4-dichlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(8) 1-(4-(4-amino-5-(4-(3-chlorophenoxy)-3-methoxyphenyl)-6-(3-(pyrrolidin-1-yl)propyl)pyrrolo[2,1-f][1,2,4]triazin-7-yl)piperidin-1-yl)-2-(diethylamino)ethanone,
(9) 7-cyclopentyl-5-(4-(3,4-dichlorophenoxy)-3-methoxyphenyl)-6-(2-(pyridin-3-yl)ethyl)pyrrolo[2,1-f][1,2,4]triazin-4-amine,
(10) 7-(3-methoxyphenyl)-5-(4-phenoxyphenyl)-6-[2-(3-pyridinyl)ethyl]pyrrolo[2,1-f][1,2,4]triazin-4-amine,
(11) 5-[4-(3,4-dichlorophenoxy)phenyl]-7-(3-methoxyphenyl)-6-[2-(3-pyridinyl)ethyl]pyrrolo[2,1-f][1,2,4]triazin-4-amine,
(12) 7-(3-methoxyphenyl)-5-(4-phenoxyphenyl)-6-(piperidin-4-yl)pyrrolo[2,1-f][1,2,4]triazin-4-amine,
(13) 7-cyclopentyl-5-(4-(3,4-dichlorophenoxy)-3-methoxyphenyl)-6-(piperidin-4-yl)pyrrolo[2,1-f][1,2,4]triazin-4-amine,
(14) 5-(4-(3-chlorophenoxy)-3-methoxyphenyl)-7-cyclopentyl-6-(piperidin-4-yl)pyrrolo[2,1-f][1,2,4]triazin-4-amine,
(15) 3-(4-(4-amino-7-cyclopentyl-6-(piperidin-4-yl)pyrrolo[2,1-f][1,2,4]triazin-5-yl)-2-methoxyphenoxy)benzonitrile,
(16) 5-[4-(3,4-dichlorophenoxy)-3-methoxy-phenyl]-7-(1-methylsulfonyl-4-piperidyl)-6-(4-piperidyl)pyrrolo[2,1-f][1,2,4]triazin-4-amine,
(17) 5-(4-(3-chlorophenoxy)-3-methoxyphenyl)-7-(1-(methylsulfonyl)piperidin-4-yl)-6-(piperidin-4-yl)pyrrolo[2,1-f][1,2,4]triazin-4-amine,
(18) (3-{4-amino-5-[4-(3-chlorophenoxy)-3-methoxyphenyl]-6-(4-pyridinyl)pyrrolo[2,1-f][1,2,4]triazin-7-yl}phenyl)(4-methyl-1-piperazinyl)methanone,
(19) 7-cycloheptyl-5-[4-(3,4-dichlorophenoxy)-3-methoxyphenyl]-6-(4-piperidinyl)pyrrolo[2,1-f][1,2,4]triazin-4-amine,
(20) 5-[4-(3-chlorophenoxy)-3-methoxyphenyl]-7-cycloheptyl-6-(4-piperidinyl)pyrrolo[2,1-f][1,2,4]triazin-4-amine,
(21) 5-[4-(3,4-dichlorophenoxy)-3-methoxyphenyl]-7-(3-methoxyphenyl)-6-(4-piperidinyl)pyrrolo[2,1-f][1,2,4]triazin-4-amine,
(22) 5-[4-(3-chlorophenoxy)-3-methoxyphenyl]-7-(3-methoxyphenyl)-6-(4-piperidinyl)pyrrolo[2,1-f][1,2,4]triazin-4-amine,
(23) N-(4-{4-amino-5-[4-(3-chlorophenoxy)-3-methoxyphenyl]-6-(4-piperidinyl)pyrrolo[2,1-f][1,2,4]triazin-7-yl}phenyl)-N-methylmethanesulfonamide,
(24) 5-[4-(3-chlorophenoxy)-3-methoxyphenyl]-7-(4-methoxyphenyl)-6-(4-piperidinyl)pyrrolo[2,1-f][1,2,4]triazin-4-amine,
(25) N-(4-{4-amino-5-[4-(3,4-dichlorophenoxy)-3-methoxyphenyl]-6-(4-piperidinyl)pyrrolo[2,1-f][1,2,4]triazin-7-yl}phenyl)-N-methylmethanesulfonamide,
(26) 3-{4-[4-amino-7-(4-methoxyphenyl)-6-(4-piperidinyl)pyrrolo[2,1-f][1,2,4]triazin-5-yl]-2-methoxyphenoxy}benzonitrile,
(27) 6-chloro-5-(4-(3-chlorophenoxy)-3-methoxyphenyl)-7-(1-(methylsulfonyl)piperidin-4-yl)pyrrolo[2,1-f][1,2,4]triazin-4-amine,
(28) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(29) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(30) 5-(4-(3-chlorophenoxy)-3-methoxyphenyl)-7-cyclopentyl-6-(pyrrolidin-3-yl)pyrrolo[2,1-f][1,2,4]triazin-4-amine,
(31) 5-[4-(3-chlorophenoxy)phenyl]-7-cyclopentyl-6-(2-ethoxyethyl)pyrrolo[2,1-f][1,2,4]triazin-4-amine,
(32) 3-{4-amino-5-[4-(3,4-dichlorophenoxy)-3-methoxyphenyl]-7-(3-methoxyphenyl)pyrrolo[2,1-f][1,2,4]triazin-6-yl}propanoic acid,
(33) {4-amino-7-cyclopentyl-5-[4-(3,4-dichlorophenoxy)-3-methoxyphenyl]pyrrolo[2,1-f][1,2,4]triazin-6-yl}acetic acid,
(34) 2-{4-amino-7-cyclopentyl-5-[4-(3,4-dichlorophenoxy)-3-methoxyphenyl]pyrrolo[2,1-f][1,2,4]triazin-6-yl}ethanol,
(35) methyl 4-amino-7-(3-methoxyphenyl)-5-(4-phenoxyphenyl)pyrrolo[2,1-f][1,2,4]triazine-6-carboxylate,
(36) 4-amino-7-(3-methoxyphenyl)-5-(4-phenoxyphenyl)pyrrolo[2,1-f][1,2,4]triazine-6-carboxylic acid,
(37) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(38) 4-amino-7-cyclopentyl-5-(4-phenoxyphenyl)pyrrolo[2,1-f][1,2,4]triazine-6-carboxylic acid,
(39) 3-{4-amino-5-[4-(3-chlorophenoxy)-3-methoxyphenyl]-7-(1-propen-2-yl)pyrrolo[2,1-f][1,2,4]triazin-6-yl}propanoic acid,
(40) (2E)-3-[4-amino-7-cyclopentyl-5-(4-phenoxyphenyl)pyrrolo[2,1-f][1,2,4]triazin-6-yl]acrylonitrile,
(41) methyl ({[4-amino-7-cyclopentyl-5-(4-phenoxyphenyl)pyrrolo[2,1-f][1,2,4]triazin-6-yl]carbonyl}amino)acetate,
(42) 6-fluoro-7-(3-methoxyphenyl)-5-(4-phenoxyphenyl)pyrrolo[2,1-f][1,2,4]triazin-4-amine,
(43) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(44) 3-[4-amino-7-cyclopentyl-5-(4-phenoxyphenyl)pyrrolo[2,1-f][1,2,4]triazin-6-yl]-2-methylacrylic acid,
(45) (2E)-3-{4-amino-7-cyclopentyl-5-[4-(3,4-dichlorophenoxy)-3-methoxyphenyl]pyrrolo[2,1-f][1,2,4]triazin-6-yl}acrylic acid,
(46) (2E)-3-[4-amino-7-cyclopentyl-5-(4-phenoxyphenyl)pyrrolo[2,1-f][1,2,4]triazin-6-yl]acrylamide,

(47) (2E)-3-[4-amino-7-cyclopentyl-5-(4-phenoxyphenyl)pyrrolo[2,1-f][1,2,4]triazin-6-yl]-2-propen-1-ol,
(48) 6-(2-aminoethyl)-7-cyclopentyl-5-(4-phenoxyphenyl)pyrrolo[2,1-f][1,2,4]triazin-4-amine,
(49) (2E)-3-[4-amino-7-cyclopentyl-5-(4-phenoxyphenyl)pyrrolo[2,1-f][1,2,4]triazin-6-yl]acrylohydrazide,
(50) 3-{4-amino-5-[4-(3,4-dichlorophenoxy)-3-methoxyphenyl]-7-(3-methoxyphenyl)pyrrolo[2,1-f][1,2,4]triazin-6-yl}propanamide,
(51) (2E)-1-(3-[4-amino-6-chloro-5-[4-(3,4-dichlorophenoxy)-3-methoxyphenyl]pyrrolo[2,1-f][1,2,4]triazin-7-yl]-1-piperidinyl)-4-(dimethylamino)-2-buten-1-one,
(52) 1-(3-{4-amino-6-chloro-5-[4-(3-chlorophenoxy)-3-methoxyphenyl]pyrrolo[2,1-f][1,2,4]triazin-7-yl}-1-pyrrolidinyl)-2-propen-1-one,
(53) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(54) 3-{4-amino-5-[4-(3-chlorophenoxy)-3-methoxyphenyl]-7-cyclopentylpyrrolo[2,1-f][1,2,4]triazin-6-yl}propanoic acid,
(55) 4-{4-amino-5-[4-(3-chlorophenoxy)-3-methoxyphenyl]-7-(3-methoxyphenyl)pyrrolo[2,1-f][1,2,4]triazin-6-yl}butanoic acid,
(56) 4-{4-amino-5-[4-(3,4-dichlorophenoxy)-3-methoxyphenyl]-7-(3-methoxyphenyl)pyrrolo[2,1-f][1,2,4]triazin-6-yl}butanoic acid,
(57) 3-(4-amino-5-[4-(3-chlorophenoxy)-3-methoxyphenyl]-7-{4-[(methylsulfonyl)amino]phenyl}pyrrolo[2,1-f][1,2,4]triazin-6-yl)propanoic acid,
(58) (2E)-3-[4-amino-7-(3-methoxyphenyl)-5-(4-phenoxyphenyl)pyrrolo[2,1-f][1,2,4]triazin-6-yl]acrylic acid,
(59) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(60) 5-[4-(3,4-dichlorophenoxy)-3-methoxyphenyl]-7-(3-methoxyphenyl)-6-[2-(1H-tetrazol-5-yl)ethyl]pyrrolo[2,1-f][1,2,4]triazin-4-amine,
(61) 3-{4-amino-5-[4-(3-chlorophenoxy)phenyl]-7-cyclopentylpyrrolo[2,1-f][1,2,4]triazin-6-yl}propanoic acid,
(62) 3-{4-amino-7-cyclopentyl-5-[4-(3,4-dichlorophenoxy)phenyl]pyrrolo[2,1-f][1,2,4]triazin-6-yl}propanoic acid,
(63) 3-[4-amino-7-cyclopentyl-5-{4-(3,4-dichlorophenoxy)-3-methoxyphenyl]pyrrolo[2,1-f][1,2,4]triazin-6-yl}propanoic acid,
(64) 3-(4-amino-7-cyclopentyl-5-{4-[3-(2-propanyl)phenoxy]phenyl}pyrrolo[2,1-f][1,2,4]triazin-6-yl)propanoic acid,
(65) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,
(66) 3-[4-amino-7-cyclopentyl-5-(4-phenoxyphenyl)pyrrolo[2,1-f][1,2,4]triazin-6-yl]propanoic acid,
(67) 3-[4-amino-7-cyclopentyl-5-(3-hydroxyphenyl)pyrrolo[2,1-f][1,2,4]triazin-6-yl]propanoic acid,
(68) 1-(3-{4-amino-6-chloro-5-[4-(3-chlorophenoxy)-3-hydroxyphenyl]pyrrolo[2,1-f][1,2,4]triazin-7-yl}-1-piperidinyl)-2-propen-1-one,
(69) 3-{4-amino-5-[4-(3-chlorophenoxy)-3-methoxyphenyl]-7-(3-methoxyphenyl)pyrrolo[2,1-f][1,2,4]triazin-6-yl}propanoic acid,
(70) 3-{4-amino-5-[4-(3-chlorophenoxy)-3-methoxyphenyl]-7-(4-methoxyphenyl)pyrrolo[2,1-f][1,2,4]triazin-6-yl}propanoic acid,
(71) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(72) 3-{4-amino-5-[4-(3-chlorophenoxy)-3-methoxyphenyl]-7-phenylpyrrolo[2,1-f][1,2,4]triazin-6-yl}propanoic acid,
(73) 3-{4-amino-5-[4-(3-chlorophenoxy)-3-methoxyphenyl]-7-(2-fluorophenyl)pyrrolo[2,1-f][1,2,4]triazin-6-yl}propanoic acid,
(74) 3-{4-amino-5-[4-(3-chlorophenoxy)-3-methoxyphenyl]-7-(3-fluorophenyl)pyrrolo[2,1-f][1,2,4]triazin-6-yl}propanoic acid,
(75) 3-{4-amino-5-[4-(3-chlorophenoxy)-3-methoxyphenyl]-7-(4-fluorophenyl)pyrrolo[2,1-f][1,2,4]triazin-6-yl}propanoic acid,
(76) 3-{4-amino-7-cyclopentyl-5-[4-(3,5-difluorophenoxy)-3-methoxyphenyl]pyrrolo[2,1-f][1,2,4]triazin-6-yl}propanoic acid,
(77) 3-{4-amino-7-cyclopentyl-5-[4-(3,5-dichlorophenoxy)-3-methoxyphenyl]pyrrolo[2,1-f][1,2,4]triazin-6-yl}propanoic acid,
(78) 3-{4-amino-7-(3-carbamoylphenyl)-5-[4-(3-chlorophenoxy)-3-methoxyphenyl]pyrrolo[2,1-f][1,2,4]triazin-6-yl}propanoic acid,
(79) 3-{4-amino-7-cyclopentyl-5-[4-(3,5-difluorophenoxy)phenyl]pyrrolo[2,1-f][1,2,4]triazin-6-yl}propanoic acid,
(80) 3-{4-amino-7-cyclopentyl-5-[4-(3,5-dichlorophenoxy)phenyl]pyrrolo[2,1-f][1,2,4]triazin-6-yl}propanoic acid,
(81) (2E)-3-[4-amino-7-cyclopentyl-5-(4-phenoxyphenyl)pyrrolo[2,1-f][1,2,4]triazin-6-yl]acrylic acid,
(82) 3-{4-amino-5-[4-(3-chlorophenoxy)-3-methoxyphenyl]-7-(2-hydroxy-2-propanyl)pyrrolo[2,1-f][1,2,4]triazin-6-yl}propanoic acid,
(83) ({[4-amino-7-cyclopentyl-5-(4-phenoxyphenyl)pyrrolo[2,1-f][1,2,4]triazin-6-yl]carbonyl}amino)acetic acid,
(84) 3-(4-amino-5-[4-(3-chlorophenoxy)-3-methoxyphenyl]-7-{4-[methyl(methylsulfonyl)amino]phenyl}pyrrolo[2,1-f][1,2,4]triazin-6-yl)propanoic acid,
(85) 3-{4-amino-5-[4-(3-chlorophenoxy)-3-methoxyphenyl]-7-[4-(methylsulfonyl)phenyl]pyrrolo[2,1-f][1,2,4]triazin-6-yl}propanoic acid,
(86) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one,
(87) 3-[4-amino-7-{4-[methyl(methylsulfonyl)amino]phenyl}-5-(4-phenoxyphenyl)pyrrolo[2,1-f][1,2,4]triazin-6-yl]propanoic acid,
(88) (2E)-3-[4-amino-7-(2-hydroxy-2-propanyl)-5-(4-phenoxyphenyl)pyrrolo[2,1-f][1,2,4]triazin-6-yl]acrylic acid,
(89) 3-(4-amino-7-cyclopentyl-5-{3-methoxy-4-[3-(2-propanyl)phenoxy]phenyl}pyrrolo[2,1-f][1,2,4]triazin-6-yl)propanoic acid,
(90) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid,
(91) (2E)-3-{4-amino-7-[1-(methylsulfonyl)-4-piperidinyl]-5-(4-phenoxyphenyl)pyrrolo[2,1-f][1,2,4]triazin-6-yl}acrylic acid,
(92) (2E)-3-[4-amino-7-cyclopentyl-5-(2-fluoro-4-phenoxyphenyl)pyrrolo[2,1-f][1,2,4]triazin-6-yl]acrylic acid,

(93) 3-[4-amino-7-(3-methoxyphenyl)-5-(4-phenoxyphenyl)pyrrolo[2,1-f][1,2,4]triazin-6-yl]propanoic acid,
(94) (2E)-3-[4-amino-7-cyclohexyl-5-(4-phenoxyphenyl)pyrrolo[2,1-f][1,2,4]triazin-6-yl]acrylic acid,
(95) (2E)-3-[4-amino-7-(1,1-dioxidotetrahydro-2H-thiopyran-4-yl)-5-(4-phenoxyphenyl)pyrrolo[2,1-f][1,2,4]triazin-6-yl]acrylic acid,
(96) (2E)-3-(4-amino-7-cyclopentyl-5-{4-[3-(2-propanyl)phenoxy]phenyl}pyrrolo[2,1-f][1,2,4]triazin-6-yl)acrylic acid,
(97) (2E)-3-{4-amino-5-[4-(3-chlorophenoxy)-3-methoxyphenyl]-7-cyclopentylpyrrolo[2,1-f][1,2,4]triazin-6-yl}acrylic acid,
(98) (2E)-3-[4-amino-5-(4-phenoxyphenyl)-7-(tetrahydro-2H-pyran-4-yl)pyrrolo[2,1-f][1,2,4]triazin-6-yl]acrylic acid,
(99) (2E)-3-[4-amino-7-(3-hydroxy-3-methylbutyl)-5-(4-phenoxyphenyl)pyrrolo[2,1-f][1,2,4]triazin-6-yl]acrylic acid,
(100) (2E)-3-[4-amino-7-isopropyl-5-(4-phenoxyphenyl)pyrrolo[2,1-f][1,2,4]triazin-6-yl]acrylic acid,
(101) N-{2-[4-amino-7-cyclopentyl-5-(4-phenoxyphenyl)pyrrolo[2,1-f][1,2,4]triazin-6-yl]ethyl}acetamide,
(102) 1-[4-amino-7-cyclopentyl-5-(4-phenoxyphenyl)pyrrolo[2,1-f][1,2,4]triazin-6-yl]-1,2-ethanediol,
(103) 4-[4-amino-7-cyclopentyl-5-(4-phenoxyphenyl)pyrrolo[2,1-f][1,2,4]triazin-6-yl]-1-hydroxy-2-butanone,
(104) 4-amino-7-cyclopentyl-N-(2-hydroxyethyl)-5-(4-phenoxyphenyl)pyrrolo[2,1-f][1,2,4]triazine-6-carboxamide,
(105) 4-amino-7-cyclopentyl-5-(4-phenoxyphenyl)-N-(1H-pyrazol-4-yl)pyrrolo[2,1-f][1,2,4]triazine-6-carboxamide,
(106) 4-amino-7-cyclopentyl-5-(4-phenoxyphenyl)-N-(1H-pyrazol-3-yl)pyrrolo[2,1-f][1,2,4]triazine-6-carboxamide,
(107) (2E)-3-[4-amino-7-cyclopentyl-5-(4-phenoxyphenyl)pyrrolo[2,1-f][1,2,4]triazin-6-yl]acrylamide,
(108) 4-amino-7-cyclopentyl-N-(2-methoxyethyl)-5-(4-phenoxyphenyl)pyrrolo[2,1-f][1,2,4]triazine-6-carboxamide,
(109) 4-amino-7-cyclopentyl-5-(4-phenoxyphenyl)pyrrolo[2,1-f][1,2,4]triazine-6-carbohydrazide,
(110) 4-amino-7-cyclopentyl-N-[2-(dimethylamino)ethyl]-5-(4-phenoxyphenyl)pyrrolo[2,1-f][1,2,4]triazine-6-carboxamide,
(111) (2E)-3-[4-amino-7-cyclopentyl-5-(4-phenoxyphenyl)pyrrolo[2,1-f][1,2,4]triazin-6-yl]-N-(1H-pyrazol-4-yl)acrylamide, or
(112) 4-amino-7-cyclopentyl-5-(4-phenoxyphenyl)pyrrolo[2,1-f][1,2,4]triazine-6-carboxamide.

7. The compound according to claim 1, which is
(1) 5-(4-(3,4-dichlorophenoxy)-3-methoxyphenyl)-7-(3-methoxyphenyl)-6-(3-(pyrrolidin-1-yl)propyl)pyrrolo[2,1-f][1,2,4]triazin-4-amine,
(2) 5-(4-(3-chlorophenoxy)-3-methoxyphenyl)-7-(3-methoxyphenyl)-6-(3-(pyrrolidin-1-yl)propyl)pyrrolo[2,1-f][1,2,4]triazin-4-amine,
(3) 7-cycloheptyl-5-(4-(3,4-dichlorophenoxy)-3-methoxyphenyl)-6-(piperidin-4-yl)pyrrolo[2,1-f][1,2,4]triazin-4-amine,
(4) 1-(3-(4-amino-6-chloro-5-(4-(3-chlorophenoxy)-3-methoxyphenyl)pyrrolo[2,1-f][1,2,4]triazin-7-yl)piperidin-1-yl)prop-2-en-1-one,
(5) 1-(3-(4-amino-6-chloro-5-(4-(3,4-dichlorophenoxy)-3-methoxyphenyl)pyrrolo[2,1-f][1,2,4]triazin-7-yl)piperidin-1-yl)prop-2-en-1-one,
(6) ethyl 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoate,
(7) ethyl (2E)-3-[7-(1-acryloyl-3-methoxy-3-azetidinyl)-4-amino-5-(4-phenoxyphenyl)pyrrolo[2,1-f][1,2,4]triazin-6-yl]acrylate,
(8) 1-(3-[4-amino-6-chloro-5-[4-(3-chlorophenoxy)-3-methoxyphenyl]pyrrolo[2,1-f][1,2,4]triazin-7-yl]-1-pyrrolidinyl)-2-propen-1-one,
(9) 3-{7-(1-acryloyl-3-piperidinyl)-4-amino-5-[4-(3-chlorophenoxy)-3-methoxyphenyl]pyrrolo[2,1-f][1,2,4]triazin-6-yl}propanoic acid,
(10) 1-(3-{4-amino-6-chloro-5-[4-(3-chlorophenoxy)-3-methoxyphenyl]pyrrolo[2,1-f][1,2,4]triazin-7-yl}-3-methoxy-1-azetidinyl)-2-propen-1-one,
(11) 3-{7-(1-acryloyl-1,2,5,6-tetrahydro-3-pyridinyl)-4-amino-5-[4-(3-chlorophenoxy)-3-methoxyphenyl]pyrrolo[2,1-f][1,2,4]triazin-6-yl}propanoic acid,
(12) 3-{7-(1-acryloyl-3-piperidinyl)-4-amino-5-[4-(3,4-dichlorophenoxy)-3-methoxyphenyl]pyrrolo[2,1-f][1,2,4]triazin-6-yl}propanoic acid,
(13) 1-[5-{4-amino-6-chloro-5-[4-(3-chlorophenoxy)-3-methoxyphenyl]pyrrolo[2,1-f][1,2,4]triazin-7-yl}-3,6-dihydro-1(2H)-pyridinyl]-2-propen-1-one, or
(14) (2E)-3-[7-(1-acryloyl-3-methoxy-3-azetidinyl)-4-amino-5-(4-phenoxyphenyl)pyrrolo[2,1-f][1,2,4]triazin-6-yl]acrylic acid.

8. A compound of formula (I) of claim 1, a salt thereof or a solvate thereof, for preventing and/or treating a Btk related disease.

9. A pharmaceutical composition comprising the compound represented by formula (I) of claim 1, a salt thereof or a solvate thereof.

* * * * *